(12) United States Patent
Kawakami et al.

(10) Patent No.: US 9,221,811 B2
(45) Date of Patent: Dec. 29, 2015

(54) CHROMONE DERIVATIVE HAVING OSTEOGENESIS PROMOTING EFFECT

(71) Applicant: Daiichi Sankyo Company, Limited, Chuo-ku, Tokyo (JP)

(72) Inventors: Katsuhiro Kawakami, Edogawa-ku (JP); Toshihiro Kiho, Funabashi (JP); Atsushi Tengeiji, Kawasaki (JP); Kentoku Gotanda, Yotsukaido (JP); Kazumasa Aoki, Koto-ku (JP); Kazuki Yano, Minato-ku (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/334,411

(22) Filed: Jul. 17, 2014

(65) Prior Publication Data

US 2014/0349991 A1    Nov. 27, 2014

Related U.S. Application Data

(63) Continuation of application No. PCT/JP2013/051576, filed on Jan. 25, 2013.

(30) Foreign Application Priority Data

Jan. 26, 2012 (JP) ................. 2012-013683

(51) Int. Cl.
```
A61K 31/445    (2006.01)
C07D 417/14    (2006.01)
C07D 405/14    (2006.01)
C07D 405/04    (2006.01)
C07D 413/14    (2006.01)
C07D 311/56    (2006.01)
C07D 311/22    (2006.01)
```

(52) U.S. Cl.
CPC ............ *C07D 417/14* (2013.01); *C07D 311/22* (2013.01); *C07D 311/56* (2013.01); *C07D 405/04* (2013.01); *C07D 405/14* (2013.01); *C07D 413/14* (2013.01)

(58) Field of Classification Search
CPC .. C07D 311/22; C07D 405/13; C07D 413/14; C07D 417/14
USPC ............... 514/210.19, 233.5, 254.11, 255.05, 514/318, 320, 422; 546/196, 194, 193; 544/130, 376, 405; 548/525, 950
See application file for complete search history.

(56) References Cited

U.S. PATENT DOCUMENTS 5,703,075 A * 12/1997 Gammill et al. ........... 514/233.5

FOREIGN PATENT DOCUMENTS

| JP | 2004-75677 A | 3/2004 |
|---|---|---|
| WO | 90/06921 A1 | 6/1990 |
| WO | 91/19707 A2 | 12/1991 |
| WO | 00/17184 A1 | 3/2000 |
| WO | 01/53266 A1 | 7/2001 |
| WO | 2007/099432 A2 | 9/2007 |
| WO | 2009/101959 A1 | 8/2009 |
| WO | 2009/129372 A1 | 10/2009 |

OTHER PUBLICATIONS

Ermili et al. "Chemical and pharmacological . . ." CA87:117750 (1977).*
Gammill et al. "Preparation of 2-morpholino . . ." CA114:42797 (1991).*
Mazzei et al. "Chemical and pharmacological . . ." CA105 :78797 (1986).*
Pouny et al. "Protoflavornoids . . ." Planta Med. v.77 pp. 461-466 (2011).*
Roma et al. "Coumarin, chromone . . ." CA139:320 (2002).*
Improper Markush, Fed. Reg v/76(27)p. 7162-7175. slide 1, 64-67 (2011).*
Morris et al. "Synthesis and biological . . ." J. Med. Chem. 36 pp. 2026-2032 (1993).*
Morris et al. "Synthesis and . . ." CA119:160228 (1993).*
Abbott, B.M., and P.E. Thompson, "Analysis of Anti-PDE3 Activity of 2-Morpholinochromone Derivatives Reveals Multiple Mechanisms of Anti-Platelet Activity," Bioorganic & Medicinal Chemistry Letters 16(4):969-973, Feb. 2006.
International Search Report and Written Opinion mailed Apr. 9, 2013, issued in corresponding International Application No. PCT/JP2013/051576, filed Jan. 25, 2013, 12 pages.
International Preliminary Report on Patentability mailed Jul. 29, 2014, issued in corresponding International Application No. PCT/JP2013/051576, filed Jan. 25, 2013, 9 pages.
Ramu, M., and B. Srinivasulu, "Facile Synthesis of 8-(1H-benzo[d]imidazol-2-yl)-7-methoxyflavones," International Journal of Pharmacy & Technology 3(4):3490-3498, Dec. 2011.

(Continued)

*Primary Examiner* — Celia Chang
(74) *Attorney, Agent, or Firm* — Christensen O'Connor Johnson Kindness PLLC

(57) ABSTRACT

Compounds or pharmacologically acceptable salts thereof for promoting osteogenesis, improving bone metabolism, preventing or treating bone fracture, preventing or treating a disease associated with bone metabolism, or in the field of orthopedics for the promotion of healing of bone fracture, a bone defect, and bone diseases such as osteoarthritis as well as in the field of dentistry for the treatment of periodontal disease and the stabilization of artificial tooth root. The compounds are represented by formula (I) or a pharmacologically acceptable salt thereof:

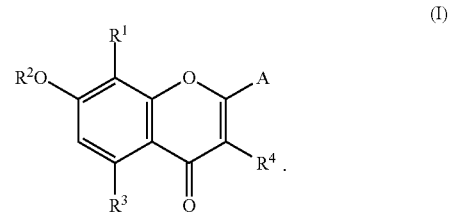

(I)

12 Claims, No Drawings

(56) References Cited

OTHER PUBLICATIONS

Riggs, B.L., and L.J. Melton III, "Involutional Osteoporosis," New England Journal of Medicine 314(26):1676-1686, Jun. 1986.

Roma, G., et al., "Coumarin, Chromone, and 4(3H)-pyrimidinone Novel Bicyclic and Tricyclic Derivatives as Antiplatelet Agents: Synthesis, Biological Evaluation, and Comparative Molecular Field Analysis," Bioorganic & Medicinal Chemistry 11(1):123-138, Jan. 2003.

Venkatesan, P., and T. Maruthavanan, "Synthesis of Substituted Flavone Derivatives as Potent Antimicrobial Agents," Bulletin of the Chemical Society of Ethiopia 25(3):419-425, 2011.

Database Registry RN 1177484-76-2, 1177318-53-4, Retrieved from STN International [online]; retrieved on Mar. 25, 2013, 1 page.

Extended European Search Report mailed Jun. 15, 2015, issued in corresponding European Application No. 13740881, filed Jan. 25, 2013, 9 pages.

\* cited by examiner

CHROMONE DERIVATIVE HAVING OSTEOGENESIS PROMOTING EFFECT

TECHNICAL FIELD

The present invention relates to a cyclic compound or a pharmacologically acceptable salt thereof which is useful for the prevention or treatment of diseases associated with bone metabolism, for example, osteoporosis, osteitis fibrosa (hyperparathyroidism), osteomalacia, and Paget's disease, and bone fracture, and the like.

BACKGROUND ART

Generally in normal bone metabolism, bone resorption by osteoclasts and osteogenesis by osteoblasts are balanced, whereby homeostasis is maintained. It is presumed that diseases associated with bone metabolism develop when the balance between bone resorption and osteogenesis is disrupted. Such diseases include osteoporosis, osteitis fibrosa (hyperparathyroidism), osteomalacia, Paget's disease, and the like. Particularly, osteoporosis often develops in postmenopausal women and elderly people with accompanying symptoms of pain such as lower back pain, bone fracture, etc. For such diseases associated with bone metabolism, hormone replacement therapies with estrogen and therapeutic agents such as bisphosphonates and calcitonins, both of which inhibit the activity of osteoclasts, have been employed.

Although many of these therapeutic agents are reported to have a bone resorption-inhibiting action, etc., none of them has yet been clearly shown to have an osteogenesis promoting effect. Particularly, impaired osteogenic ability due to reduced bone turnover is reported to be the main cause of senile osteoporosis (Non-patent Literature 1), and thus a medicinal agent promoting osteogenesis is considered to be effective. In view of the above, development of a clinically highly effective, orally administrable osteogenesis promoter is demanded.

WO2009/101959 (Patent Literature 1) describes compounds as shown below, which however differ in structural features from the compound of the present invention.

[Chemical formula 1]

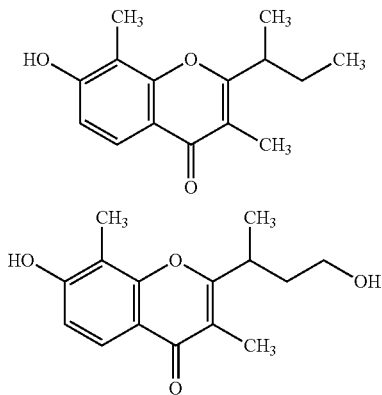

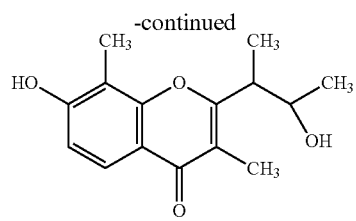

CITATION LIST

Patent Literature

Patent Literature 1: WO2009/101959

Non-Patent Literature

Non-patent Literature 1: New Eng. J. Med. 314, 1976 (1986)

SUMMARY OF INVENTION

Technical Problem

In order to reduce pain and risk of bone fracture in diseases associated with bone metabolism such as osteoporosis, bone mass and bone strength need to be increased. As a means of increasing bone mass and bone strength, it is considered important to promote osteogenesis by osteoblasts as this is definitely considered to be effective. Accordingly, an object of the present invention is to provide a highly safe, orally or locally administrable novel compound or a pharmacologically acceptable salt thereof which exhibits an osteogenesis promoting effect, etc.

Solution to Problem

The present inventors conducted an intensive study in order to develop a therapeutic medication having an osteogenesis promoting effect. As a result, they have found an excellent compound that exhibits a potent osteogenesis promoting effect and is potentially capable of serving as a therapeutic medication for the prevention or treatment of diseases associated with bone metabolism and bone fracture, thereby completing the present invention.

Specifically, the present invention provides (1) a compound represented by the general formula (I) or a pharmacologically acceptable salt thereof:

[Chemical formula 2]

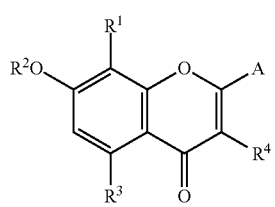

wherein each substituent is defined as follows:
$R^1$ represents
a halogen atom, a cyano group, a vinyl group, an allyl group, a nitro group, an amino group, a C3-C6 cycloalkyl group, a C1-C6 alkyl group optionally substituted by one or two or more groups selected from substituent group a,
a C1-C6 alkoxy group optionally substituted by one or two or more groups selected from substituent group a,
a C1-C6 alkylamino group optionally substituted by one or two or more groups selected from substituent group a,
a di-C1-C6 alkylamino group optionally substituted by one or two or more groups selected from substituent group a, or
a heterocyclic group optionally substituted by one or two or more groups selected from substituent group a, wherein the substituent group a consists of a C3-C6 cycloalkyl group, a hydroxyl group, a halogen atom, an oxo group, and a phenyl group;

$R^2$ represents a hydrogen atom or a protective group for a hydroxyl group;

$R^3$ represents a hydrogen atom, a halogen atom, or a C1-C6 alkyl group;

$R^4$ represents a hydrogen atom or a C1-C6 alkyl group optionally substituted by a C1-C6 alkoxy group; and A represents
a C3-C6 cycloalkyl group substituted by one or two or more groups selected from substituent group c,
a C3-C6 cycloalkenyl group substituted by one or two or more groups selected from substituent group c, or
a heterocyclic group substituted by one or two or more groups selected from substituent group c, wherein the substituent group c consists of
a hydroxyl group, a hydroxy-C1-C6 alkyl group, a C1-C6 alkylsulfonyl group, an aminocarbonyl group, a C1-C6 alkylaminocarbonyl group, a di-C1-C6 alkylaminocarbonyl group,
a C3-C7 cycloalkylaminocarbonyl group, a heterocyclecarbonyl group,
a C1-C6 alkoxy-C1-C6 alkylcarbonyl group, a C1-C6 alkylaminosulfonyl group,
a di-C1-C6 alkylaminosulfonyl group,
a C3-C7 cycloalkylsulfonyl group, a heterocycle-sulfonyl group,
a C1-C6 alkyl group optionally substituted by one or two or more groups selected from substituent group d,
a C1-C6 alkylcarbonyl group optionally substituted by one or two or more groups selected from substituent group d,
a C1-C6 alkoxycarbonyl group optionally substituted by one or two or more groups selected from substituent group d,
a heterocyclic group optionally substituted by one or two or more groups selected from substituent group d,
a benzoyl group optionally substituted by one or two or more groups selected from substituent group d, and
a benzyl group optionally substituted by one or two or more groups selected from substituent group d, wherein the substituent group d consists of a halogen atom, a carboxy group, an oxo group, an aminocarbonyl group, a C1-C6 alkoxy group,
a C1-C6 alkoxycarbonyl group, a C1-C6 alkylaminocarbonyl group,
a di-C1-C6 alkylaminocarbonyl group, a heterocycle-carbonyl group, and
a phenylaminocarbonyl group optionally substituted by one or two or more groups selected from substituent group e, wherein the substituent group e consists of
a heterocycle-carbonyl group and a heterocycle-C1-C6 alkyl group.

Preferred aspects of the present invention are as described below.

(2)
The compound or pharmacologically acceptable salt thereof according to (1), wherein $R^1$ is a group selected from the following substituents:
a halogen atom, an allyl group, a C3-C6 cycloalkyl group, and a C1-C6 alkyl group optionally substituted by group(s) selected from substituent group a.

(3)
The compound or pharmacologically acceptable salt thereof according to (1), wherein $R^2$ is a hydrogen atom.

(4)
The compound or pharmacologically acceptable salt thereof according to (1), wherein $R^3$ is a hydrogen atom.

(5)
The compound or pharmacologically acceptable salt thereof according to (1), wherein $R^4$ is a hydrogen atom or a methyl group.

(6)
The compound or pharmacologically acceptable salt thereof according to (1), wherein A is a group selected from the following substituents:
a piperidine group substituted by group(s) selected from substituent group c.

(7)
The compound or pharmacologically acceptable salt thereof according to (6), wherein the substituent group c is the following substituent group:
a C1-C6 alkylsulfonyl group, an aminocarbonyl group, a di-C1-C6 alkylaminocarbonyl group,
a di-C1-C6 alkylaminosulfonyl group, a C1-C6 alkoxy-C1-C6 alkylcarbonyl group,
a C1-C6 alkylcarbonyl group optionally substituted by group(s) selected from substituent group d,
a C1-C6 alkoxycarbonyl group optionally substituted by group(s) selected from substituent group d,
a heterocyclic group optionally substituted by group(s) selected from substituent group d,
a benzoyl group optionally substituted by group(s) selected from substituent group d, and
a benzyl group optionally substituted by group(s) selected from substituent group d.

(8)
A compound described below or a pharmacologically acceptable salt thereof:
2-(1-acetylpiperidin-4-yl)-7-hydroxy-3,8-dimethyl-4H-chromen-4-one,
ethyl 4-(7-hydroxy-3,8-dimethyl-4-oxo-4H-chromen-2-yl)piperidine-1-carboxylate,
7-hydroxy-3,8-dimethyl-2-[1-(methylsulfonyl)piperidin-4-yl]-4H-chromen-4-one,
N-ethyl-4-(7-hydroxy-3,8-dimethyl-4-oxo-4H-chromen-2-yl)piperidine-1-carboxamide,
4-(7-hydroxy-3,8-dimethyl-4-oxo-4H-chromen-2-yl)-N,N-dimethylpiperidine-1-carboxamide,
7-hydroxy-2-[1-(methoxyacetyl)piperidin-4-yl]-3,8-dimethyl-4H-chromen-4-one,
4-(7-hydroxy-3,8-dimethyl-4-oxo-4H-chromen-2-yl)-N,N-dimethylpiperidine-1-sulfonamide,
2-(1-butanoylpiperidin-4-yl)-7-hydroxy-3,8-dimethyl-4H-chromen-4-one,
2-[1-(ethylsulfonyl)piperidin-4-yl]-7-hydroxy-3,8-dimethyl-4H-chromen-4-one,
7-hydroxy-3,8-dimethyl-2-[1-(3,3,3-trifluoropropanoyl)piperidin-4-yl]-4H-chromen-4-one,
7-hydroxy-3,8-dimethyl-2-(1-propanoylpiperidin-4-yl)-4H-chromen-4-one, 7-hydroxy-3,8-dimethyl-2-[1-(2-methylpropanoyl)piperidin-4-yl]-4H-chromen-4-one, 2-[1-(2,2-dimethylpropanoyl)piperidin-4-yl]-7-hydroxy-3,8-dimethyl-4H-chromen-4-one, 7-hydroxy-3,8-dimethyl-2-[1-(phenylcarbonyl)piperidin-4-yl]-4H-chromen-4-one, 7-hydroxy-3,8-dimethyl-2-[1-(1,3-thiazol-2-yl)piperidin-4-yl]-4H-chromen-4-one, 7-hydroxy-3,8-dimethyl-2-[1-(pyridin-2-yl)piperidin-4-yl]-4H-chromen-4-one, 7-hydroxy-3,8-dimethyl-2-[1-(pyrazin-2-yl)piperidin-4-yl]-4H-chromen-4-one, 8-allyl-7-hydroxy-3-methyl-2-(1-propanoylpiperidin-4-yl)-4H-chromen-4-one, 8-cyclopropyl-7-hydroxy-3-methyl-2-(1-propanoylpiperidin-4-yl)-4H-chromen-4-one, 8-(cyclopropylmethyl)-7-hydroxy-3-methyl-2-(1-propanoylpiperidin-4-yl)-4H-chromen-4-one, and 7-hydroxy-3-methyl-2-(1-propanoylpiperidin-4-yl)-8-(2,2,2-trifluoroethyl)-4H-chromen-4-one.

(9)

A pharmaceutical composition comprising a compound or pharmacologically acceptable salt thereof according to (1).

(10)

The pharmaceutical composition according to (9), wherein the pharmaceutical composition is for use in promoting osteogenesis.

(11)

The pharmaceutical composition according to (9), wherein the pharmaceutical composition is for use in for improving bone metabolism.

(12)

The pharmaceutical composition according to (9), wherein the pharmaceutical composition is for use in for preventing or treating bone fracture.

(13)

The pharmaceutical composition according to (9), wherein the pharmaceutical composition is for use in for preventing or treating a disease associated with bone metabolism.

(14)

The pharmaceutical composition according to (13), wherein the disease associated with bone metabolism is osteoporosis.

(15)

The pharmaceutical composition according to (9), wherein the pharmaceutical composition is for use in the field of orthopedics for the promotion of healing of bone fracture, a bone defect, and bone diseases such as osteoarthritis as well as in the field of dentistry for the treatment of periodontal disease and the stabilization of artificial tooth root.

The present invention also encompasses aspects of the invention as described below.

(16)

A method for improving bone metabolism, comprising administering an effective amount of a pharmaceutical composition according to (9) to a mammal.

(17)

A method for preventing or treating a disease associated with bone metabolism, comprising administering an effective amount of a pharmaceutical composition according to (9) to a mammal.

(18)

A method for preventing or treating osteoporosis or bone fracture, comprising administering an effective amount of a pharmaceutical composition according to (9) to a mammal.

Advantageous Effects of Invention

The compound of the present invention or pharmacologically acceptable salt thereof has low toxicity and an osteogenesis promoting effect, and thus is useful for the prevention or treatment of metabolic bone disease associated with reduced osteogenic ability relative to bone resorption ability. Examples of such metabolic bone disease include osteoporosis, osteitis fibrosa (hyperparathyroidism), osteomalacia, and further, Paget's disease, which affects systemic parameters of bone metabolism. In particular, the compound of the present invention or pharmacologically acceptable salt thereof is useful for senile osteoporosis associated with impaired osteogenic ability. Further, application of the compound of the present invention or pharmacologically acceptable salt thereof in the field of orthopedics for the promotion of healing of bone fracture, a bone defect, and bone diseases such as osteoarthritis as well as in the field of dentistry for the treatment of periodontal disease, the stabilization of artificial tooth root, etc. is anticipated.

DESCRIPTION OF EMBODIMENTS

Hereinafter, the present invention will be described in detail.

Terms such as substituents used in the present specification are as defined below.

A halogen atom:

A fluorine group, a chlorine group, or a bromine group a C3-C6 Cycloalkyl Group:

A cyclic alkyl group having 3 to 6 carbon atoms, preferably a cyclopropyl group, a cyclobutyl group, a cyclopentyl group, or a cyclohexyl group A C3-C6 Cycloalkenyl Group:

A cyclic alkenyl group having 3 to 6 carbon atoms, preferably a cyclopropenyl group, a cyclobutenyl group, a cyclopentenyl group, or a cyclohexenyl group A C1-C6 Alkyl Group:

A linear or branched alkyl group having 1 to 6 carbon atoms, preferably a methyl group, an ethyl group, a propyl group, or an isopropyl group A Hydroxy-C1-C6 Alkyl Group:

A group in which a linear or branched alkyl group having 1 to 6 carbon atoms is substituted by 1 to 3 hydroxyl groups, preferably a hydroxymethyl group, a hydroxyethyl group, a hydroxypropyl group, or a hydroxyisopropyl group A C1-C6 Alkoxy Group:

A group in which an oxygen atom is bound by a C1-C6 alkyl group, preferably a methoxy group, an ethoxy group, a propoxy group, or an isopropoxy group A C1-C6 Alkylamino Group:

A group in which one aforementioned C1-C6 alkyl group is bound to an amino group, preferably a methylamino group, an ethylamino group, a propylamino group, or an isopropylamino group A Di-C1-C6 Alkylamino Group:

A group in which two aforementioned C1-C6 alkyl groups are bound to an amino group, preferably a dimethylamino group, a diethylamino group, a dipropylamino group, or a diisopropylamino group A C1-C6 Alkylaminocarbonyl Group:

A group in which one C1-C6 alkyl group is bound to an aminocarbonyl group, preferably a methylaminocarbonyl group or an ethylaminocarbonyl group A Di-C1-C6 Alkylaminocarbonyl Group:

A group in which two C1-C6 alkyl groups are bound to an aminocarbonyl group, preferably a dimethylaminocarbonyl group or a diethylaminocarbonyl group A C1-C6 Alkylaminosulfonyl Group:
A group in which one C1-C6 alkyl group is bound to an aminosulfonyl group, preferably a methylaminosulfonyl group or an ethylaminosulfonyl group A Di-C1-C6 Alkylaminosulfonyl Group:
A group in which two C1-C6 alkyl groups are bound to an aminosulfonyl group, preferably a dimethylaminosulfonyl group or a diethylaminosulfonyl group A C1-C6 Alkylcarbonyl Group:
A group in which a carbonyl group is bound by a C1-C6 alkyl group, preferably an acetyl group, an ethylcarbonyl group, a propylcarbonyl group, an isopropylcarbonyl group, or a butylcarbonyl group A C1-C6 Alkoxycarbonyl Group:
A group in which a carbonyl group is bound by a C1-C6 alkoxy group, preferably an acetoxy group, an ethylcarbonyloxy group, a propylcarbonyloxy group, an isopropylcarbonyloxy group, or a butylcarbonyloxy group A C1-C6 Alkoxy-C1-C6 Alkylcarbonyl Group:
A group in which a C1-C6 alkoxy group is bound to a C1-C6 alkylcarbonyl group, preferably a methoxyacetyl group, an ethoxyacetyl group, a methoxypropionyl group, an ethoxypropionyl group, or a propoxyacetyl group A C1-C6 Alkylsulfonyl Group:
A group in which a sulfonyl group is bound by a C1-C6 alkyl group, preferably a methylsulfonyl group, an ethylsulfonyl group, a propylsulfonyl group, an isopropylsulfonyl group, or a butylsulfonyl group, more preferably a methylsulfonyl group or an ethylsulfonyl group A C3-C7 Cycloalkylaminocarbonyl Group:
A group in which an aminocarbonyl group is bound by a C3-C7 alkyl group, preferably a cyclopropylaminocarbonyl group, a cyclobutylaminocarbonyl group, a cyclopentylaminocarbonyl group, a cyclohexylaminocarbonyl group, or a cycloheptylaminocarbonyl group, more preferably a cyclopropylaminocarbonyl group, a cyclobutylaminocarbonyl group, or a cyclopentylaminocarbonyl group A C3-C7 Cycloalkylsulfonyl Group:
A group in which a sulfonyl group is bound by a C3-C7 alkyl group, preferably a cyclopropylsulfonyl group, a cyclobutylsulfonyl group, a cyclopentylsulfonyl group, a cyclohexylsulfonyl group, or a cycloheptylsulfonyl group, more preferably a cyclopropylsulfonyl group, a cyclobutylsulfonyl group, or a cyclopentylsulfonyl group A Heterocyclic Group:
A saturated or unsaturated cyclic group containing one or more heteroatoms as atoms constituting the ring(s) in which a plurality of cyclic groups may be condensed.

Specifically, the heterocyclic group includes groups as described below.

A 3-membered saturated heterocyclic group: An aziridinyl group, an oxiranyl group, or a thiiranyl group
A 3-membered unsaturated heterocyclic group: A 1H or 2H azirinyl group, an oxiranyl group, or a thiiranyl group
A 4-membered saturated heterocyclic group: An azetidinyl group, an oxetanyl group, or a thietanyl group
A 5-membered saturated heterocyclic group: A pyrrolidinyl group, a tetrahydrofuranyl group, or a tetrahydrothiophenyl group
A 5-membered unsaturated heterocyclic group: A pyrrolyl group, a furanyl group, or a thienyl group
A 5-membered unsaturated heterocyclic group containing a plurality of heteroatoms: An imidazolyl group, a pyrazolyl group, an oxazolyl group, a thiazolyl group, or an imidazolinyl group
A 6-membered saturated heterocyclic group: A piperidinyl group, a tetrahydropyranyl group, or a tetrahydrothiopyranyl group
A 6-membered saturated heterocyclic group containing a plurality of heteroatoms: A morpholinyl group or a piperazinyl group
A 6-membered unsaturated heterocyclic group: A pyridyl group or a tetrahydropyridyl group
A 6-membered unsaturated heterocyclic group containing a plurality of heteroatoms: A pyrazinyl group, a pyrimidinyl group, or a thiazinyl group
A 7-membered saturated heterocyclic group: An azepanyl group, an oxepanyl group, or a thiepanyl group
A 7-membered unsaturated heterocyclic group containing a plurality of heteroatoms: A 1,4-diazepanyl group
A 7-membered unsaturated heterocyclic group: An azepinyl group, an oxepinyl group, or a thiepinyl group The group having condensed rings includes groups as described below.

An indolyl group, an isoindolyl group, a benzimidazolyl group, a quinolyl group, an isoquinolyl group, a quinoxalyl group, a chromenyl group, an isochromenyl group, a tetrahydroisoquinolyl group, and a decahydroisoquinolyl group The heterocyclic group is preferably a 4- to 7-membered heterocyclic group such as an azetidinyl group, a pyrrolidinyl group, a piperidinyl group, a morpholinyl group, a piperazinyl group, an azepanyl group, a 1,4-diazepanyl group, a pyrrolyl group, a thiazolyl group, a pyridyl group, a tetrahydropyridyl group, a tetrahydropyranyl group, a tetrahydrofuranyl group, a tetrahydroisoquinolyl group, or a decahydroisoquinolyl group.

A Heterocycle-Carbonyl Group:
A group in which a carbonyl group is bound by a heterocyclic group A Heterocycle-C1-C6 Alkyl Group:
A group in which a C1-C6 alkyl group is bound by a heterocyclic group A Heterocycle-Sulfonyl Group:
A group in which a sulfonyl group is bound by a heterocyclic group A Protective Group for a Hydroxyl Group:
It refers to a protective group for a hydroxyl group described in T. W. Greene and P. G. Wuts, "Protective Groups in Organic Synthesis (3rd edition, 1999)" and is preferably the following group:
an acetyl group, a benzoyl group, a trimethylsilyl group, a t-butyldimethylsilyl group, a methoxymethyl group, a methoxyethoxymethyl group, a tetrahydropyranyl group, or a benzyl group.

A Protective Group for an Amino Group:
It refers to a protective group for an amino group described in T. W. Greene and P. G. Wuts, "Protective Groups in Organic Synthesis (3rd edition, 1999)" and is preferably the following group:
a t-butoxycarbonyl group, a benzyloxycarbonyl group, an allyloxycarbonyl group, a benzyl group, or an allyl group.

The preferred combination of substituents in the compound represented by the general formula (I) is as shown below.

$R^1$: a halogen atom, an allyl group, a C3-C6 cycloalkyl group, or a C1-C6 alkyl group optionally substituted by group(s) selected from substituent group a
$R^2$: a hydroxyl group
$R^3$: a hydrogen atom
$R^4$: a C1-C6 alkyl group
A: a heterocyclic group optionally substituted by group(s) selected from substituent group c Substituent Group c:
a C1-C6 alkylsulfonyl group, an aminocarbonyl group, a di-C1-C6 alkylaminocarbonyl group,
a di-C1-C6 alkylaminosulfonyl group, a C1-C6 alkoxy-C1-C6 alkylcarbonyl group,
a C1-C6 alkylcarbonyl group optionally substituted by group(s) selected from substituent group d,
a C1-C6 alkoxycarbonyl group optionally substituted by group(s) selected from substituent group d,
a heterocyclic group optionally substituted by group(s) selected from substituent group d,
a benzoyl group optionally substituted by group(s) selected from substituent group d, or
a benzyl group optionally substituted by group(s) selected from substituent group d
Substituent Group d:
a halogen atom, a C1-C6 alkoxy group, a C1-C6 alkylaminocarbonyl group, or a di-C1-C6 alkylaminocarbonyl group The compound represented by the general formula (I) is preferably any of compounds described in Examples, particularly preferably any of the following compounds:
2-(1-acetylpiperidin-4-yl)-7-hydroxy-3,8-dimethyl-4H-chromen-4-one,
ethyl 4-(7-hydroxy-3,8-dimethyl-4-oxo-4H-chromen-2-yl)piperidine-1-carboxylate,
7-hydroxy-3,8-dimethyl-2-[1-(methylsulfonyl)piperidin-4-yl]-4H-chromen-4-one,
N-ethyl-4-(7-hydroxy-3,8-dimethyl-4-oxo-4H-chromen-2-yl)piperidine-1-carboxamide,
4-(7-hydroxy-3,8-dimethyl-4-oxo-4H-chromen-2-yl)-N,N-dimethylpiperidine-1-carboxamide,
7-hydroxy-2-[1-(methoxyacetyl)piperidin-4-yl]-3,8-dimethyl-4H-chromen-4-one,
4-(7-hydroxy-3,8-dimethyl-4-oxo-4H-chromen-2-yl)-N,N-dimethylpiperidine-1-sulfonamide,
2-(1-butanoylpiperidin-4-yl)-7-hydroxy-3,8-dimethyl-4H-chromen-4-one,
2-[1-(ethylsulfonyl)piperidin-4-yl]-7-hydroxy-3,8-dimethyl-4H-chromen-4-one,
7-hydroxy-3,8-dimethyl-2-[1-(3,3,3-trifluoropropanoyl)piperidin-4-yl]-4H-chromen-4-one,
7-hydroxy-3,8-dimethyl-2-(1-propanoylpiperidin-4-yl)-4H-chromen-4-one,
7-hydroxy-3,8-dimethyl-2-[1-(2-methylpropanoyl)piperidin-4-yl]-4H-chromen-4-one,
2-[1-(2,2-dimethylpropanoyl)piperidin-4-yl]-7-hydroxy-3,8-dimethyl-4H-chromen-4-one,
7-hydroxy-3,8-dimethyl-2-[1-(phenylcarbonyl)piperidin-4-yl]-4H-chromen-4-one,
7-hydroxy-3,8-dimethyl-2-[1-(1,3-thiazol-2-yl)piperidin-4-yl]-4H-chromen-4-one,
7-hydroxy-3,8-dimethyl-2-[1-(pyridin-2-yl)piperidin-4-yl]-4H-chromen-4-one,
7-hydroxy-3,8-dimethyl-2-[1-(pyrazin-2-yl)piperidin-4-yl]-4H-chromen-4-one,
8-allyl-7-hydroxy-3-methyl-2-(1-propanoylpiperidin-4-yl)-4H-chromen-4-one,
8-cyclopropyl-7-hydroxy-3-methyl-2-(1-propanoylpiperidin-4-yl)-4H-chromen-4-one,
8-(cyclopropylmethyl)-7-hydroxy-3-methyl-2-(1-propanoylpiperidin-4-yl)-4H-chromen-4-one,
7-hydroxy-3-methyl-2-(1-propanoylpiperidin-4-yl)-8-(2,2,2-trifluoroethyl)-4H-chromen-4-one,
7-hydroxy-3,8-dimethyl-2-{1-[(propan-2-yloxy)acetyl]piperidin-4-yl}-4H-chromen-4-one,
2-[1-(ethoxyacetyl)piperidin-4-yl]-7-hydroxy-3,8-dimethyl-4H-chromen-4-one,
3-ethyl-7-hydroxy-2-[1-(methoxyacetyl)piperidin-4-yl]-8-methyl-4H-chromen-4-one, and
8-ethyl-7-hydroxy-2-[1-(methoxyacetyl)piperidin-4-yl]-3-methyl-4H-chromen-4-one The phrase "optionally substituted by" refers to either being unsubstituted or being substituted by one to three substituents.

The term "substituted" refers to being substituted by one to three substituents.

The term "treatment" refers to curing diseases or symptoms.

The term "pharmacologically acceptable salt thereof" refers to a salt that can be used as a medicine. A compound having an acidic group or a basic group can be obtained as a basic salt or an acidic salt through reaction with a base or an acid, respectively; therefore, such a salt is referred to as a "pharmacologically acceptable salt thereof".

Preferable examples of a pharmacologically acceptable "basic salt" of the compound include: an alkali metal salt such as a sodium salt, a potassium salt, and a lithium salt; an alkaline earth metal salt such as a magnesium salt and a calcium salt; an organic basic salt such as an N-methylmorpholine salt, a triethylamine salt, a tributylamine salt, a diisopropylethylamine salt, a dicyclohexylamine salt, a N-methylpiperidine salt, a pyridine salt, a 4-pyrrolidinopyridine salt, and a picoline salt; and an amino acid salt such as a glycine salt, a lysine salt, an arginine salt, an ornithine salt, a glutamic acid salt, and an aspartic acid salt, of which an alkali metal salt is preferable.

Preferable examples of a pharmacologically acceptable "acidic salt" of the compound include: an inorganic acid salt such as hydrohalide (e.g., hydrofluoride, hydrochloride, hydrobromide, and hydroiodide), nitrate, perchlorate, sulfate, and phosphate; an organic acid salt such as lower alkanesulfonate (e.g., methanesulfonate, trifluoromethanesulfonate, and ethanesulfonate), arylsulfonate (e.g., benzenesulfonate and p-toluenesulfonate), acetate, malate, fumarate, succinate, citrate, ascorbate, tartrate, oxalate, and maleate; and an amino acid salt such as a glycine salt, a lysine salt, an arginine salt, an ornithine salt, a glutamic acid salt, and an aspartic acid salt, of which hydrohalide, particularly, hydrochloride, is most preferable.

The compound of the present invention or pharmacologically acceptable salt thereof may absorb water, contain hygroscopic water, or form a hydrate, when left in the atmosphere or subjected to recrystallization. The present invention also encompasses compounds in such various forms of hydrates, solvates, and crystal polymorphs.

The compound of the present invention, pharmacologically acceptable salt thereof, or a solvate of the compound or salt may be present as various isomers such as geometric isomers including a cis-form, a trans-form, etc., tautomers, or enantiomers such as a D-form and an L-form, depending on the kind or combination of substituents. Unless otherwise specifically restricted, the compound also encompasses all of these isomers and stereoisomers, and mixtures containing these isomers and stereoisomers in any ratio. A mixture of these isomers can be separated by publicly known means of separation.

The compound of the present invention also encompasses a labeled compound, namely a compound in which one or two or more atoms are substituted by isotopes (e.g., $^2H$, $^3H$, $^{13}C$, $^{14}C$, and $^{35}S$).

Further, the present invention also encompasses so-called prodrugs. Prodrugs refer to compounds having a group that can be converted into an amino group, a hydroxyl group, a carboxyl group, and the like of the compound by hydrolysis or under physiological conditions. Examples of groups forming such a prodrug include ones described in Prog. Med., Vol. 5, p. 2157-2161, 1985. More specifically, examples of prodrugs of the compound having an amino group can include compounds in which the amino group is acylated, alkylated, or phosphorylated (e.g., a compound in which the amino group is converted into eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, or tert-butyl). Examples of prodrugs of the compound having a hydroxyl group can include compounds in which the hydroxyl group is acylated, alkylated, phosphorylated, or borated (e.g., a compound in which the hydroxyl group is converted into acetyl, palmitoyl, propanoyl, pivaloyl, succinyl, fumaryl, alanyl, or dimethylaminomethylcarbonyl). Examples of prodrugs of the compound having a carboxyl group include compounds in which the carboxyl group is esterified or amidated (e.g., a compound in which the carboxyl group is ethyl-esterified, phenyl-esterified, carboxymethyl-esterified, dimethylaminomethyl-esterified, pivaloyloxymethyl-esterified, ethoxycarbonyloxyethyl-esterified, amidated, or methylamidated).

(Production Method)

The compound of the present invention or pharmacologically acceptable salt thereof can be produced by applying various publicly known production methods, while taking advantage of characteristics based on the basic structure of the compound or the kinds of substituents. Examples of publicly known methods include methods described in "ORGANIC FUNCTIONAL GROUP PREPARATIONS", second edition, ACADEMIC PRESS, INC., 1989, and "Comprehensive Organic Transformations", VCH Publishers Inc., 1989, and the like.

Upon production of the compound of the present invention, depending on the kinds of functional groups present in the compound, it may be effective, from a production technique point of view, to protect a functional group of a raw material or intermediate compound with an appropriate protective group or to replace a functional group by a readily-convertible group in advance.

Examples of functional groups include an amino group, a hydroxyl group, and a carboxyl group. Examples of protective groups thereof include ones described in T. W. Greene and P. G. Wuts, "Protective Groups in Organic Synthesis (3rd edition, 1999)".

The protective group or the group readily convertible to the functional group can be appropriately selected for use in accordance with the respective reaction conditions for the methods for producing the compounds.

According to these methods, a desired compound can be obtained by introducing the group and carrying out the reaction, and then removing the protective group or converting the group into a desired group, as needed.

Further, a prodrug of the compound can be produced, similarly to the aforementioned protective groups, by introducing a specific group into a raw material or intermediate compound, or carrying out the reactions using the compound produced. The reaction for producing the prodrug can be carried out by applying a method publicly known to those skilled in the art such as methods normally performed, for example, esterification, amidation, dehydration, and hydrogenation.

Hereinafter, methods for producing the compounds will be described. However, the production method of the present invention is not limited to the methods described below in any way.

Method A involves: step A-I of converting compound 1 to compound 2 through Friedel-Crafts acylation reaction; step A-II of introducing a protective group $R^2$ to the phenolic hydroxyl group to produce compound 3; step A-III of acylating the compound 3 to obtain compound 4; and step A-IV of cyclizing the compound 4 to produce compound 5 or compound 6. The compound 6 can be converted to compound 5 by deprotecting the protective group $R^2$ for the hydroxyl group (step A-V).

[Chemical formula 3]

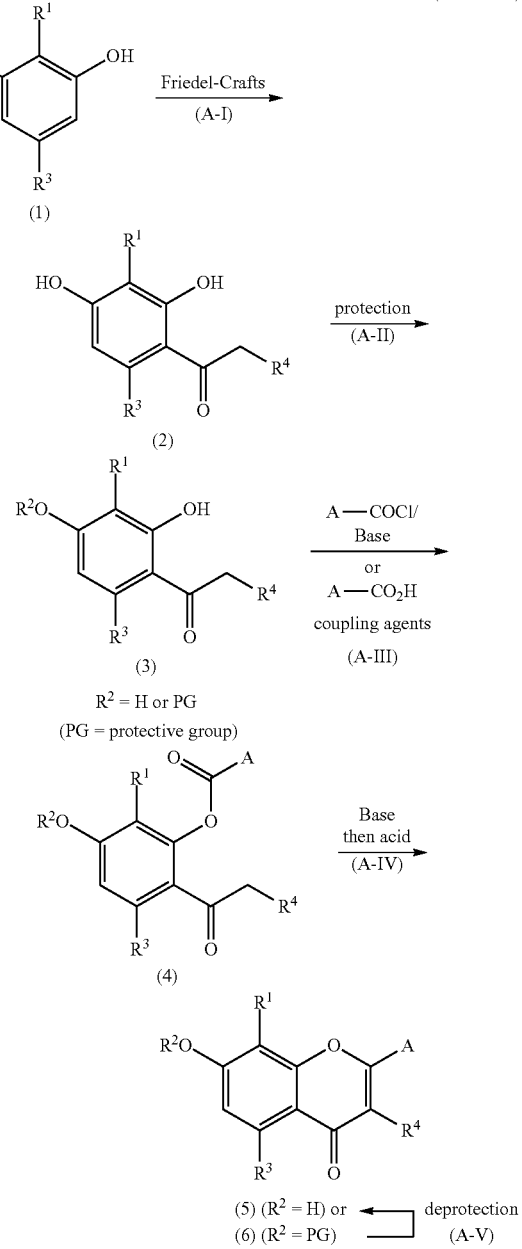

In the reaction scheme of Method A, $R^1$, $R^2$, $R^3$, $R^4$, and A are as defined above;

PG represents a protective group for a hydroxyl group; and

X represents a halogen atom.

The reaction of step A-I (Friedel-Crafts reaction) is carried out under conditions as shown below using an acid catalyst.
Reagent: acid chloride, acid anhydride, etc.
Acid catalyst: boron trifluoride-ethyl ether complex, aluminum chloride, etc.
Solvent: dichloromethane or dichloroethane
Reaction temperature: cooling with ice to 100° C.
Reaction time: 1 to 12 hours
The reaction of step A-II (hydroxyl group protection reaction) is carried out under conditions as shown below.
Preferred protective group: a benzyl group, a methoxymethyl group, etc.
Reagent (protective group used is shown within parentheses): benzyl bromide (benzyl group), chloromethoxymethane (methoxymethyl group), and a base
Solvent: dichloromethane, chloroform, tetrahydrofuran, acetone, N,N-dimethylformamide, etc.
Reaction temperature: cooling with ice to room temperature
Reaction time: 2 to 48 hours Step A-III (Acylation Reaction):
(1) The reaction is carried out under conditions as shown below using acid halide.
Base used: pyridine, 2,6-lutidine, N,N-dimethylaminopyridine, triethylamine, diisopropylethylamine, etc.
Preferred base: N,N-dimethylaminopyridine, triethylamine, etc.
Solvent: dichloromethane, chloroform, tetrahydrofuran, N,N-dimethylformamide, etc.
Reaction temperature: cooling with ice to room temperature
Reaction time: 4 to 48 hours
(2) The reaction is carried out under conditions as shown below using carboxylic acid.
Condensing agent used: N,N'-dicyclohexylcarbodiimide, N,N'-diisopropylcarbodiimide, 1-ethyl-3-(3-dimethylaminopropyl)carbodiimide hydrochloride, etc.
Preferred condensing agent: 1-ethyl-3-(3-dimethylaminopropyl)carbodiimide hydrochloride, etc.
Solvent: dichloromethane, chloroform, tetrahydrofuran, N,N-dimethylformamide, etc.
Reaction temperature: cooling with ice to room temperature
Reaction time: 4 to 72 hours
The reaction of step A-IV (cyclization reaction) is carried out under conditions as shown below.
(1) Base treatment step
Base: sodium hydride, potassium t-butoxide, lithium diisopropylamide, lithium 1,1,1,3,3,3-hexamethyldisilazide, sodium 1,1,1,3,3,3-hexamethyldisilazide, etc.
Solvent: N,N-dimethylformamide, tetrahydrofuran, 1,2-dimethoxyethane, etc.
Reaction temperature: cooling with ice to room temperature
Reaction time: 0.5 to 4 hours
(2) Acid Treatment Step
Acid: sulfuric acid, hydrochloric acid, nitric acid, trifluoroacetic acid, trifluoromethanesulfonic acid, etc.
Solvent: N,N-dimethylformamide, methanol, ethanol, etc.
Reaction temperature: room temperature to 100° C.
Reaction time: 1 to 8 hours
The reaction of step A-V (deprotection) is carried out under conditions as shown below.
Preferred protective group: a benzyl group or a methoxymethyl group
Treatment method for deprotection (which differs depending on the kind of protective group; the kind of protective group is shown within parentheses): hydrogenation (benzyl group) or acid treatment (methoxymethyl group)
Method B involves: step B-I of halogenating compound 7 to obtain compound 8; step B-II of introducing a protective group $R^2$ to the phenolic hydroxyl group to produce compound 9 (as in step A-II); step B-III of producing compound 10; and B-IV step of deprotecting the protective group $R^2$ for the hydroxyl group in the compound 10 (as in step A-V) to produce compound 11.

[Chemical formula 4]

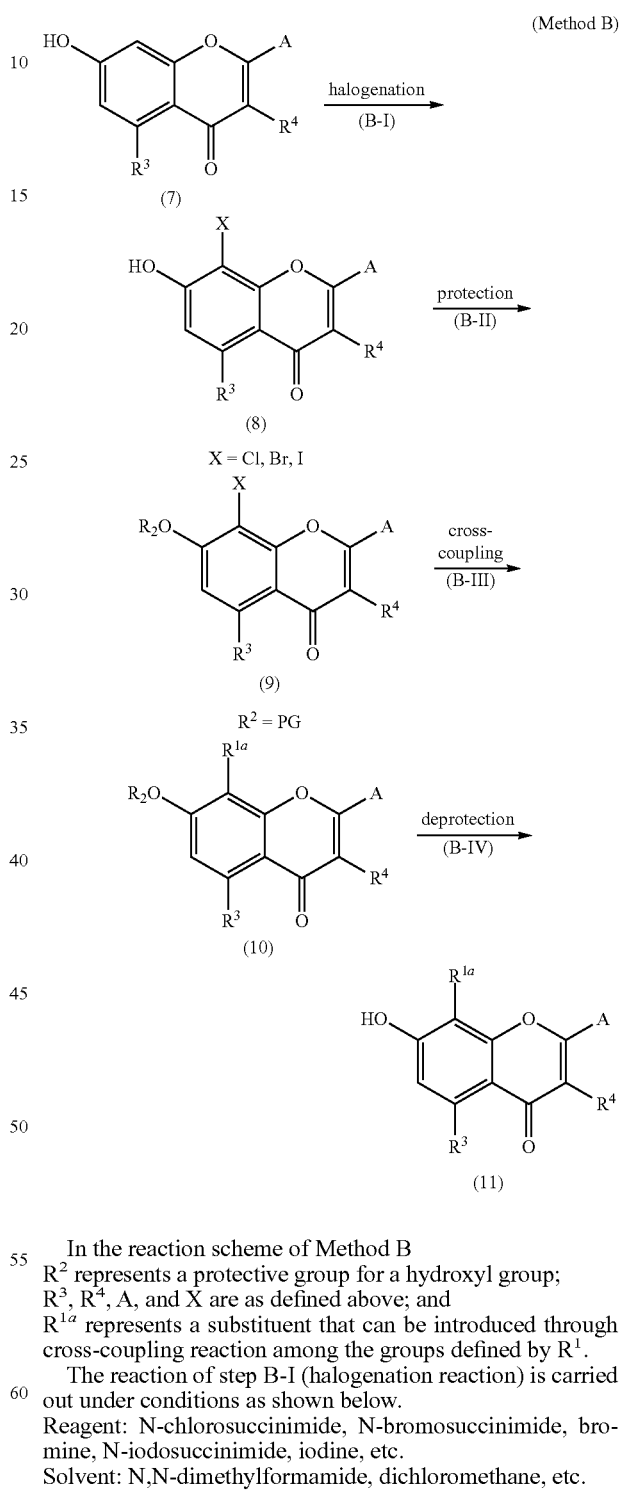

In the reaction scheme of Method B
$R^2$ represents a protective group for a hydroxyl group;
$R^3$, $R^4$, A, and X are as defined above; and
$R^{1a}$ represents a substituent that can be introduced through cross-coupling reaction among the groups defined by $R^1$.
The reaction of step B-I (halogenation reaction) is carried out under conditions as shown below.
Reagent: N-chlorosuccinimide, N-bromosuccinimide, bromine, N-iodosuccinimide, iodine, etc.
Solvent: N,N-dimethylformamide, dichloromethane, etc.
Reaction temperature: cooling with ice to 60° C.
Reaction time: 1 to 12 hours
Step B-II (hydroxyl group protection reaction) can be carried out in the same way as in step A-II.

The reaction of step B-III (cross-coupling reaction; in this context, the cross-coupling reaction refers to Suzuki-Miyaura coupling, Still coupling, Buchwald-Hartwig coupling, or the like) is carried out under conditions as shown below.

Reagent: a boronic acid reagent (Suzuki-Miyaura coupling), a tin reagent (Still coupling), or primary and secondary amines (Buchwald-Hartwig coupling)

Base: sodium bicarbonate, sodium carbonate, potassium carbonate, potassium phosphate, sodium phosphate, or potassium t-butoxide, etc.

Catalyst: a palladium catalyst such as tetrakistriphenylphosphinepalladium or bisdiphenylphosphinoferrocene palladium dichloride, etc.

Solvent: tetrahydrofuran, 1,2-dimethoxyethane, methanol, ethanol, N,N-dimethylformamide, or an aqueous solvent thereof, etc.

Reaction temperature: room temperature to 120° C.
Reaction time: 1 to 24 hours

Step B-IV (deprotection) can be carried out in the same way as in step A-V.

Method C involves: step C-I of introducing a formyl group to a position adjacent to the phenolic hydroxyl group on the benzene ring of compound 7 to produce compound 12; step C-II of protecting the phenolic hydroxyl group of the compound 12 with a protective group $R^2$ to obtain compound 13; step C-III of introducing a $R^{1b}$ group to the formyl group of the compound 13 through nucleophilic addition reaction to produce compound 14; and step C-IV of subjecting the compound 14 to (1) dehydroxylation reaction and (2) deprotection reaction of the protective group for the hydroxyl group to produce compound 15.

[Chemical formula 5]

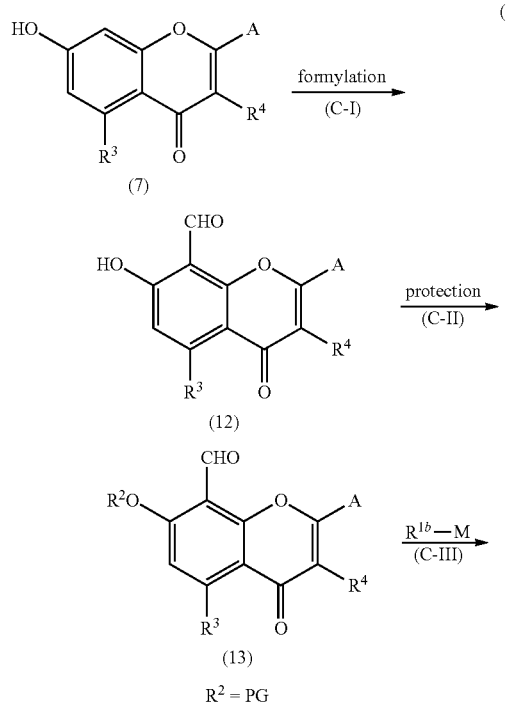

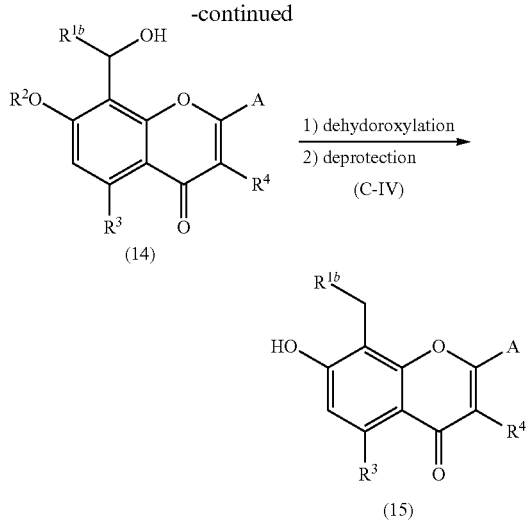

In the reaction scheme of Method C,
$R^2$ represents a protective group for a hydroxyl group;
$R^3$, $R^4$, and A are as defined above;
$R^{1b}$ represents a substituent that can be introduced through nucleophilic addition reaction using an organic metal reagent such as an alkali metal reagent or a Grignard reagent, among the groups defined by $R^1$; and
$R^{1b}$-M represents an organic metal reagent such as an alkali metal reagent or a Grignard reagent.

The reaction of step C-I (formylation reaction) is carried out under conditions as shown below.
Reagent: hexamethylenetetramine, etc.
Solvent: acetic acid, trifluoroacetic acid, etc.
Reaction temperature: 60 to 120° C.
Reaction time: 1 to 24 hours Step C-II (hydroxyl group protection reaction) can be carried out in the same way as in step A-II.

The reaction of step C-III (nucleophilic addition reaction) is carried out under conditions as shown below.
Reagent: a Grignard reagent, an organic lithium reagent, trifluoromethyltrimethylsilane, etc.
Solvent: diethyl ether, tetrahydrofuran, 1,2-dimethoxyethane, dimethyl sulfoxide (for trifluoromethylation), etc.
Reaction temperature: −78° C. to room temperature
Reaction time: 1 to 6 hours Step C-IV:
(1) The dehydroxylation reaction is carried out under conditions as shown below.
Reagent: trifluoroacetic acid and triethylsilane (method 1), or reaction with 1,1-thiocarbonylimidazole followed by treatment with tri-n-butyltin hydride and a catalytic amount of AIBN (method 2)
Solvent: dichloromethane (method 1) or tetrahydrofuran (method 2)
Reaction temperature: cooling with ice to room temperature (method 1) or 50 to 120° C. (method 2)
Reaction time: 1 to 6 hours
(2) The deprotection reaction can be carried out in the same way as in step A-V.

Method D involves: step D-I of oxidizing the formyl group of the compound 13 (produced in step C-II of Method C) to produce compound 16; step D-II of (1) amidating the carboxy group of the compound 16, (2) forming an isoxazoline ring through cyclization reaction, and (3) subjecting the protective group for the hydroxyl group to deprotection reaction to produce compound 17.

[Chemical formula 6]

(Method D)

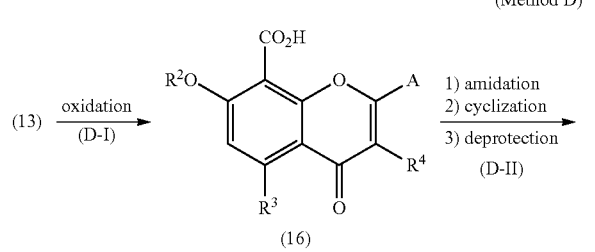

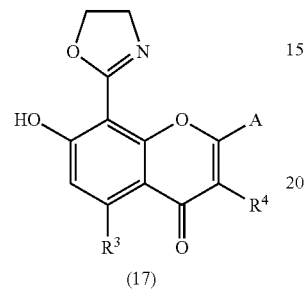

In the reaction scheme of Method D,
$R^2$, $R^3$, $R^4$, and A are as defined above.

The reaction of step D-I (oxidation reaction) is carried out under conditions as shown below.

Reagent: sodium chlorite (chlorous acid) and 2-methyl-2-butene
Solvent: water, t-butyl alcohol, etc.
Reaction temperature: cooling with ice to room temperature
Reaction time: 6 to 24 hours Step D-II:

(1) The amidation reaction is carried out under conditions as shown below.
Reagent: production of acid chloride using thionyl chloride, oxalyl chloride, phosphorus oxychloride, or the like, followed by reaction with amine, or amidation using a condensing agent as in (2) of step A-I.
Solvent: dichloromethane, chloroform, tetrahydrofuran, N,N-dimethylformamide, etc.
Reaction temperature: cooling with ice to room temperature
Reaction time: 1 to 24 hours (2) The cyclization reaction is carried out under conditions as shown below.
Reagent: thionyl chloride, oxalyl chloride, tosyl chloride, or mesyl chloride and a base, or the same condensing agent as in (2) of step A-I
Solvent: dichloromethane, chloroform, 1,2-dichloroethane, tetrahydrofuran, N,N-dimethylformamide, etc.
Reaction temperature: cooling with ice to 100° C.
Reaction time: 6 hours to 5 days (3) The deprotection reaction can be carried out in the same way as in step A-V.

Method E involves step E-I of subjecting compound 7 to (1) allylation reaction of the hydroxyl group and then (2) Claisen rearrangement reaction to produce compound 18.

[Chemical formula 7]

(Method E)

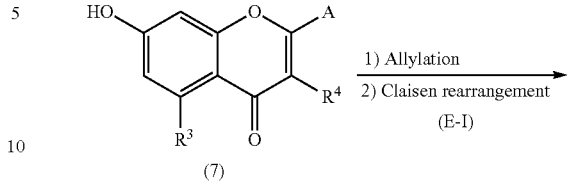

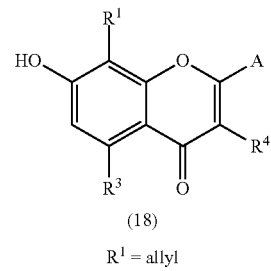

$R^1$ = allyl

In the reaction scheme of Method E,
$R^1$ represents an allyl group; and
$R^3$, $R^4$, and A are as defined above.

Step E-I:

(1) The allylation reaction is carried out under conditions as shown below.
Reagent: allyl halide and a base
Solvent: dichloromethane, acetone, tetrahydrofuran, N,N-dimethylformamide, etc.
Reaction temperature: room temperature to 100° C.
Reaction time: 1 to 48 hours (2) The Claisen rearrangement reaction is carried out under conditions as shown below.
Solvent: dimethylaniline, nitromethane, water, etc.
Reaction temperature: 100 to 250° C.
Reaction time: 1 to 12 hours Method F involves: step F-II of deprotecting a protective group on a nitrogen atom using compound 10, compound 5 or compound 6 obtained from compound 5 by step F-I (hydroxyl group protection) to produce compound 19; and step F-III of introducing a substituent $R^5$ to the nitrogen atom of the compound 19 (e.g., by a method such as acylation, alkylation, reductive amination, or sulfonylation) to produce compound 20 or compound 21. When $R^2$ is a protective group as in compound 21, the protective group for the hydroxyl group can be deprotected in step F-IV to produce the compound 20. In the case of using hydrogenation reaction in the step F-II, unsaturated bonds in $R^1$, $R^{1a}$, $R^3$, and $R^4$ of the compound 10, 5, or 6 can be reduced into saturated bonds simultaneously with the deprotection.

[Chemical formula 8]

(Method F)

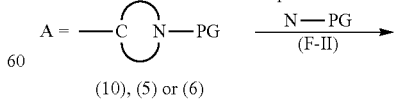

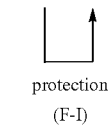

-continued

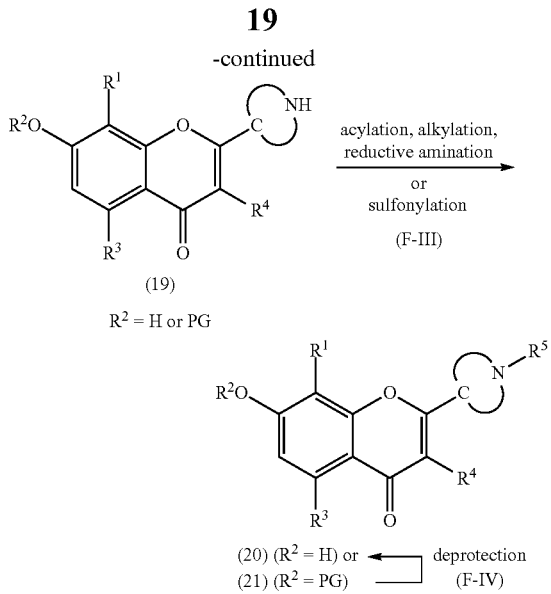

(19)

$R^2 = H$ or PG

(20) ($R^2 = H$) or
(21) ($R^2 = PG$)  ← deprotection (F-IV)

In the reaction scheme of Method F,
$R^1$, $R^3$, and $R^4$ are as defined above;
$R^2$ represents a protective group for a hydroxyl group;
A represents a heterocyclic group containing a nitrogen atom protected with a protective group;
PG represents a protective group for an amino group; and
$R^5$ represents a group selected from the aforementioned substituent group c.

The hydroxyl group protection reaction of step F-I can be carried out in the same way as in step A-II.

The reaction of step F-II (deprotection reaction of the protective group on the nitrogen atom) is carried out under conditions as shown below.
Reagent: palladium-carbon and hydrogen gas
Solvent: methanol or ethanol
Reaction temperature: room temperature
Reaction time: 0.5 to 6 hours Step F-III: Reaction through which a substituent is introduced to the nitrogen atom
(1) The acylation reaction is carried out under conditions as shown below.
Reagent: acid halide or carboxylic acid and the same condensing agent as in (2) of step A-I or isocyanate and a base
Solvent: dichloromethane, chloroform, tetrahydrofuran, N,N-dimethylformamide, etc.
Reaction temperature: cooling with ice to room temperature
Reaction time: 2 to 48 hours
(2) The alkylation reaction is carried out under conditions as shown below.
Reagent: alkyl halide, benzyl halide, or allyl halide and a base
Solvent: dichloromethane, tetrahydrofuran, N,N-dimethylformamide, etc.
Reaction temperature: cooling with ice to room temperature
Reaction time: 2 to 48 hours
(3) The reductive amination reaction is carried out under conditions as shown below.
Reagent: aldehyde and a reducing agent such as sodium cyanoborohydride, or hydrogenation conditions
Solvent: dichloromethane, tetrahydrofuran, N,N-dimethylformamide, acetic acid, methanol, ethanol, etc.
Reaction temperature: cooling with ice to 60° C.
Reaction time: 1 to 6 hours The hydroxyl group deprotection reaction of step F-IV can be carried out in the same way as in step A-V.

Method G involves: step G-I of (1) cyclizing compound 3 and (2) methylating its thiocarbonyl to produce compound 22; step G-II of oxidizing the sulfur atom of the compound 22 to produce compound 23; step G-III of subjecting the compound 23 to substitution reaction with a heterocyclic group containing a nitrogen atom to produce compound 24; and step G-IV of deprotecting the protective group $R^2$ for the hydroxyl group of the compound 24 to produce compound 25.

[Chemical formula 9]

(Method G)

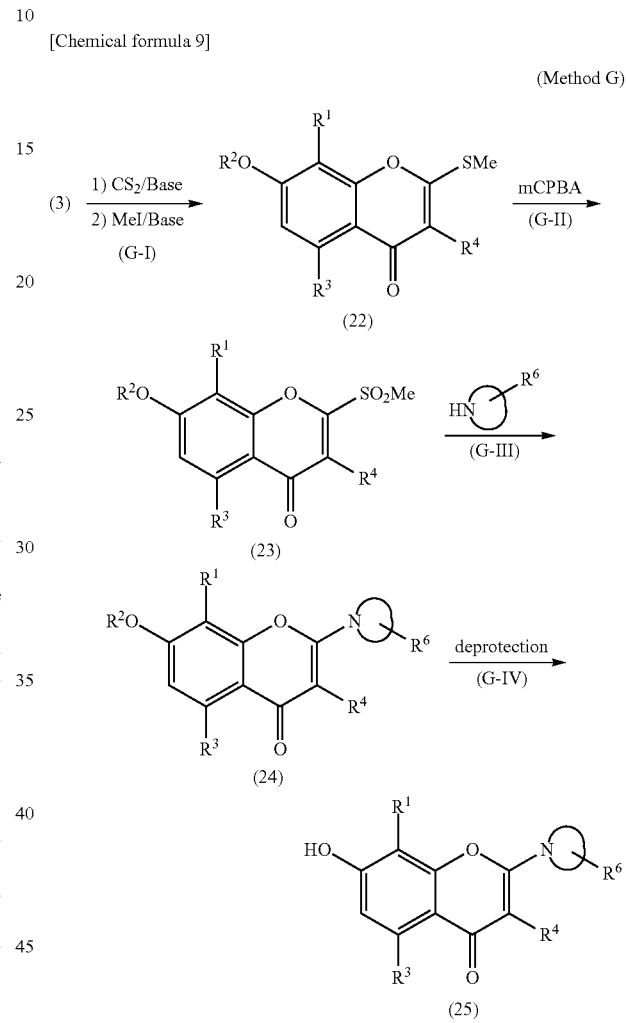

In the reaction scheme of Method G,
$R^1$, $R^3$, and $R^4$ are as defined above;
$R^2$ represents a protective group for a hydroxyl group;
B represents a nitrogen atom-containing heterocyclic group substituted by a substituent $R^6$; and
$R^6$ represents a group selected from the aforementioned substituent group c.

Step G-I: cyclization reaction and methylation reaction of thiocarbonyl
(1) The cyclization reaction is carried out under conditions as shown below.
Reagent: carbon disulfide and potassium t-butoxide or sodium hydride
Solvent: tetrahydrofuran, 1,2-dimethoxyethane, etc.
Reaction temperature: cooling with ice to room temperature
Reaction time: 3 to 24 hours
(2) The methylation reaction of thiocarbonyl is carried out under conditions as shown below.

Reagent: methyl halide, dimethyl sulfate, or methyl sulfonate, and a base
Solvent: acetone, tetrahydrofuran, 1,2-dimethoxyethane, N,N-dimethylformamide, etc.
Reaction temperature: room temperature to 80° C.
Reaction time: 1 to 6 hours Step G-II:

(1) The oxidation reaction of the methylthio group is carried out under conditions as shown below.
Reagent: m-chloroperbenzoic acid
Solvent: dichloromethane, chloroform, etc.
Reaction temperature: cooling with ice to room temperature
Reaction time: 3 to 24 hours The reaction of step G-III (introduction of amine) is carried out under conditions as shown below.
Reagent: primary or secondary linear amine or cyclic amine and a base
Solvent: dichloromethane, tetrahydrofuran, N,N-dimethylformamide, dimethyl sulfoxide, etc.
Reaction temperature: room temperature to 100° C.
Reaction time: 1 to 6 hours The hydroxyl group deprotection reaction of step G-VI can be carried out in the same way as in step A-V.

The compounds produced by these methods can be isolated and purified by publicly known methods, for example, extraction, precipitation, distillation, chromatography, fractional crystallization, and recrystallization.

When the compound or a production intermediate thereof contains an asymmetric carbon(s), enantiomers exist. Each of these enantiomers can be isolated and purified by standard methods such as fractional crystallization (salt fractionation) in which an enantiomer is recrystallized with an appropriate salt, and column chromatography. Examples of reference literature for methods for separating optical isomers from racemates include J. Jacques et al., "Enantiomers, Racemates and Resolution, John Wiley And Sons, Inc."

The compound of the present invention or pharmacologically acceptable salt thereof has low toxicity and an excellent osteogenesis promoting effect. The compound of the present invention or pharmacologically acceptable salt thereof can therefore be used for the prevention or treatment (particularly, treatment) of diseases associated with bone metabolism such as osteoporosis, Paget's disease of bone, and osteoarthritis, and bone fracture and thus is useful.

In the case of administering the compound of the present invention or pharmacologically acceptable salt thereof to a mammal (particularly, a human), it can be administered systemically or locally by the oral or parenteral route.

The dosage form of a pharmaceutical composition of the present invention is appropriately selected depending on the administration method, and can be produced by normally employed methods for preparing various kinds of formulations.

Examples of dosage forms for an oral pharmaceutical composition include a tablet, a pill, a powder, a granule, a capsule, a liquid medicine, a suspension, an emulsion, a syrup, and an elixir. Medicines in these dosage forms can be prepared according to standard methods using any agent appropriately selected as needed from among normally employed additives such as an excipient, a binder, a disintegrant, a lubricant, a swelling agent, a swelling aid, a coating agent, a plasticizer, a stabilizer, an antiseptic, an antioxidant, a colorant, a solubilizing aid, a suspending agent, an emulsifier, a sweetener, a preservative, a buffer, a diluent, and a humectant.

Examples of dosage forms for a parenteral pharmaceutical composition include an injection, an ointment, a gel, a cream, a poultice, a patch, an aerosol, a spray, an eye drop, a nasal drop, a suppository, and an inhalant. Medicines in these dosage forms can be prepared according to standard methods using any agent appropriately selected as needed from among normally employed additives such as a stabilizer, an antiseptic, a solubilizing aid, a humectant, a preservative, an antioxidant, a fragrance, a gelling agent, a neutralizer, a solubilizing aid, a buffer, an isotonic agent, a surfactant, a colorant, a buffer, a viscosity enhancer, a humectant, a filler, an absorption promoter, a suspending agent, and a binder.

The dose, etc. of the compound represented by the general formula (I) or pharmacologically acceptable salt thereof varies depending on the symptoms, age, body weight, and the kind, dose, etc. of the drug to be administered in combination. Normally, the compound represented by the general formula (I) or pharmacologically acceptable salt thereof is preferably administered in a range of 0.001 mg to 1000 mg, in terms of the amount of the compound represented by the general formula (I), per adult (presumed to weigh approximately 60 kg) per dose.

The area to which the compound represented by the general formula (I) or pharmacologically acceptable salt thereof is administered is preferably systemic or local.

The number of doses of the compound represented by the general formula (I) or e pharmacologically acceptable salt thereof is preferably
once to several times a month,
once to several times a week, or
once to several times a day.

The method for administering the compound represented by the general formula (I) or pharmacologically acceptable salt thereof is oral or parenteral administration or preferably continuous administration via the intravenous route for one to 24 hours a day.

Other active ingredients can be used in combination with the pharmaceutical composition of the present invention as needed as long as such active ingredients do not impair the efficacy of the present invention.

The present invention also encompasses a method for preventing and/or treating the aforementioned diseases, comprising administering the compound of the present invention or pharmacologically acceptable salt thereof.

The present invention further encompasses use of the compound of the present invention or pharmacologically acceptable salt thereof for the production of the pharmaceutical composition.

Formulation Example 1

Powder

Five grams of a compound, 895 g of lactose, and 100 g of corn starch are mixed using a blender to give a powder.

Formulation Example 2

Granules

Five grams of a compound, 865 g of lactose, and 100 g of low-substituted hydroxypropylcellulose are mixed, followed by addition of 300 g of a 10% aqueous solution of hydroxypropylcellulose. The resulting mixture is kneaded and granulated using extrusion granulation equipment, and then dried to give granules.

Formulation Example 3

Tablet

Five grams of a compound, 90 g of lactose, 34 g of corn starch, 20 g of crystalline cellulose, and 1 g of magnesium stearate are mixed using a blender, followed by tabletting using a tablet machine to give a tablet.

Test Examples

Test Example 1

Osteoblast Differentiation Test

ST2 cells, murine bone marrow-derived stromal cells, (obtained from RIKEN) were used.

In this test, α-MEM media (obtained from GIBCO BRL Cat. No. 10370-021) containing 10% (v/v) of inactivated fetal bovine serum (FBS, obtained from Hyclone Laboratories, Inc.) and 1% (v/v) of Penicillin-Streptomycin Liquid (obtained from GIBCO BRL Cat. No. 15140-122) (hereinafter, abbreviated as 10%-FBS-αMEM) were used. In this test, all culturing was performed in a CO2 incubator (37° C., 95% humidity, 5% CO2).

The aforementioned cells were detached with 2 mL of a 0.25% trypsin solution (obtained from GIBCO BRL Cat. No. 15050-065) and dispersed by the addition of 10 mL of 10%-FBS-αMEM. Subsequently, the cells were collected by centrifugation (25° C., 800 rpm, five minutes). Then, a cell suspension containing 40000 of the cells/mL of 10%-FBS-αMEM was prepared. The cell suspension was then dispensed into 96-well microplates (the product of Falcon), 100 µL per well, at a density of 4000 cells/well, followed by culturing for 24 hours. To the wells, except for a well containing a control group described below, each compound was dispensed at final concentrations of 0.01, 0.03, 0.1, and 0.3 µg/ml.

To the well of a control group, DMSO was dispensed at a final concentration of 0.1% (v/v). After four days of culturing, the activity of alkaline phosphatase (ALP) was measured in each group.

The measurement of ALP activity was performed as follows: the medium in each well of the culture plates was completely removed. Each well was then washed by dispensing 100 µL of Dulbecco's phosphate buffer (obtained from GIBCO BRL Cat. No. 14190-144) and then removing it. A cell lysate solution containing 10 mM MgCl2 and 2% (v/v) Triton X-100 (Sigma) was prepared and dispensed at 50 µL/well, followed by stirring at room temperature for five minutes. An ALP substrate solution containing 50 mM diethanolamine (Wako Pure Chemical Industries, Ltd., Cat. No. 099-03112) and 20 mM p-nitrophenyl phosphate (Wako Pure Chemical Industries, Ltd., Cat. No. 147-02343) was prepared and dispensed at 50 µL/well, and the plates were left to stand at room temperature for 10 minutes. Subsequently, absorbance was measured using a microplate reader (Bio-Rad Laboratories, Inc.). Setting the measurement value of the control group of each plate at 100%, the increase (%) in alkaline phosphatase activity in the test compound-addition group was calculated, which was assessed as the degree of osteoblast differentiation.

The table below shows compounds that exhibited an increase of 100% or more in alkaline phosphatase activity (2-fold or more increase in alkaline phosphatase activity relative to the control) in this test, and their concentrations (µM).

TABLE 1

| Compound of Example | Concentration(µM) |
|---|---|
| Example 2-4 | 0.043 |
| Example 3-2 | 0.029 |
| Example 4-2 | 0.093 |
| Example 6 | 0.006 |
| Example 7-3 | 0.015 |

TABLE 1-continued

| Compound of Example | Concentration(µM) |
|---|---|
| Example 8 | 0.011 |
| Example 9 | 0.042 |
| Example 10 | 0.012 |
| Example 11 | 0.005 |
| Example 12 | 0.006 |
| Example 13 | 0.009 |
| Example 14 | 0.006 |
| Example 15 | 0.005 |
| Example 16 | 0.0007 |
| Example 17 | 0.017 |
| Example 18 | 0.054 |
| Example 19 | 0.069 |
| Example 20 | 0.004 |
| Example 21 | 0.007 |
| Example 22 | 0.014 |
| Example 23-3 | 0.041 |
| Example 24 | 0.030 |
| Example 25-2 | 0.013 |
| Example 26-4 | 0.066 |
| Example 28 | 0.056 |
| Example 29 | 0.087 |
| Example 30-2 | 0.054 |
| Example 31-4 | 0.031 |
| Example 33-2 | 0.002 |
| Example 34-5 | 0.057 |
| Example 37-5 | 0.032 |
| Example 38 | 0.090 |
| Example 39 | 0.088 |

Test Example 2

Effect on Bone Density

Eight to 12 week old female F344 rats were purchased from Charles River Laboratories Japan, Inc. and used in the following experiment.

This test was conducted at N=8. Rats were anesthetized by the intraperitoneal administration of 40 mg/kg of Somnopentyl (purchased from Kyoritsu Seiyaku Corporation), followed by oophorectomy.

From the day after surgery, a control group received a 0.5% methyl cellulose solution (purchased from Wako Pure Chemical Industries, Ltd., Cat. No. 133-14255) alone, whereas another group received a suspension of the test compound in this solution (0.5% methyl cellulose solution), for the test.

The administration was performed orally once a day, six days a week. Six weeks after administration, the rats were euthanized by removal of whole blood from the lower abdominal aorta under Somnopentyl anesthesia, and the left and right femur was excised.

After removal of soft tissues, the bone density of the femur thus excised was measured (apparatus: DXA apparatus DCS-600R manufactured by Aloka Co., Ltd.). The bone density was assessed in the whole femur as well as in three equal sections of the whole femur, namely the proximal end, the shaft, and the distal end.

The compound of Example 11 significantly increased the bone density at a dose of 25 mg/kg, compared with the control group. The Dunnett's test was used in certification.

EXAMPLES

In Examples, the following symbols were used.

Ac: an acetyl group, Bn: a benzyl group, Et: an ethyl group, and Me: a methyl group

Example 1

7-Hydroxy-3,8-dimethyl-2-(1-methylazetidin-3-yl)-4H-chromen-4-one hydrochloride

Example 1-1

1-Benzyl 3-[3-(benzyloxy)-2-methyl-6-propanoylphenyl]azetidine-1,3-dicarboxylate

[Chemical formula 10]

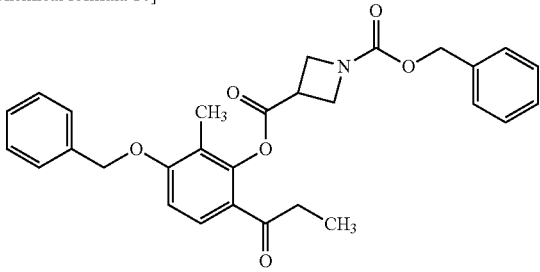

A solution of 1-[4-(benzyloxy)-2-hydroxy-3-methylphenyl]propan-1-one (2.20 g, 8.14 mmol), 1-[(benzyloxy)carbonyl]azetidine-3-carboxylic acid (2.67 g, 9.77 mmol), 1-ethyl-3-(3-dimethylaminopropyl)carbodiimide hydrochloride (12.48 g, 65.1 mmol), and N,N-dimethyl-4-aminopyridine (994 mg, 8.14 mmol) in dichloromethane (100 mL) was stirred at room temperature for 2 days. The reaction solution was washed with water and then dried over sodium sulfate. The desiccant was filtered off, and then the filtrate was concentrated under reduced pressure. The obtained residue was purified by silica gel column chromatography (n-hexane/ethyl acetate=95/5→50/50) to obtain 2.77 g of the title compound (yield: 70%).

$^1$H-NMR (CDCl$_3$) δ: 7.70 (1H, d, J=8.7 Hz), 7.44-7.29 (10H, m), 6.83 (1H, d, J=8.7 Hz), 5.18-5.08 (4H, m), 4.50-4.46 (2H, m), 4.34 (2H, t, J=8.9 Hz), 3.82-3.73 (1H, m), 2.86 (2H, q, J=7.2 Hz), 2.10 (3H, s), 1.13 (3H, t, J=7.2 Hz).

MS; m/z: 488 (M+H)$^+$

Example 1-2

Benzyl 3-[7-(benzyloxy)-3,8-dimethyl-4-oxo-4H-chromen-2-yl]azetidine-1-carboxylate

[Chemical formula 11]

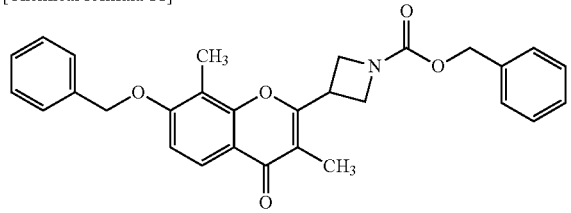

To a solution of 1-benzyl 3-[3-(benzyloxy)-2-methyl-6-propanoylphenyl]azetidine-1,3-dicarboxylate (2.77 g, 5.68 mmol) obtained in Example 1-1 in dimethylformamide (16 mL), 60% sodium hydride (568 mg, 14.2 mmol) was added in small portions under cooling with ice, and then the mixture was brought back to room temperature and stirred for 1 hour. The reaction solution was cooled with ice. Then, acetic acid (1.30 mL, 22.7 mmol) was added dropwise thereto, subsequently methanol (40 mL) and concentrated hydrochloric acid (4 mL) were added thereto, and the mixture was heated with stirring at a bath temperature of 75° C. for 3 hours. The reaction solution was allowed to cool, and then methanol in the mixture was distilled off under reduced pressure. Water was added to the obtained residue, followed by extraction with ethyl acetate. The organic layer was washed with water and then dried over magnesium sulfate. The desiccant was filtered off, and then the filtrate was concentrated under reduced pressure. The obtained residue was purified by silica gel column chromatography (n-hexane/ethyl acetate=80/20→50/50) to obtain 295 mg of the title compound (yield: 11%).

$^1$H-NMR (CDCl$_3$) δ: 8.02 (1H, d, J=8.7 Hz), 7.47-7.31 (10H, m), 7.03 (1H, d, J=8.7 Hz), 5.22 (2H, s), 5.16 (2H, s), 4.39 (4H, d, J=7.3 Hz), 4.15-4.06 (1H, m), 2.34 (3H, s), 2.00 (3H, s).

MS; m/z: 470 (M+H)$^+$

Example 1-3

2-(Azetidin-3-yl)-7-hydroxy-3,8-dimethyl-4H-chromen-4-one

[Chemical formula 12]

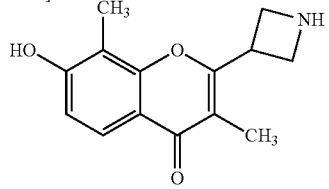

To a solution of benzyl 3-[7-(benzyloxy)-3,8-dimethyl-4-oxo-4H-chromen-2-yl]azetidine-1-carboxylate (625 mg, 1.33 mmol) obtained in Example 1-2 in methanol (12 mL), 10% palladium-carbon (water content: 50%, 200 mg) was added, and the mixture was stirred for 2 hours under a hydrogen atmosphere. Dichloromethane (20 mL) and methanol (20 mL) were added to the reaction solution, and the palladium-carbon was removed by filtration through celite. The filtrate was concentrated under reduced pressure to obtain 297 mg of the title compound (yield: 91%).

$^1$H-NMR (DMSO-d$_6$) δ: 7.70 (1H, d, J=8.7 Hz), 6.93 (1H, d, J=8.7 Hz), 4.27-3.83 (2H, m), 3.68-3.58 (2H, m), 3.42 (1H, t, J=7.6 Hz), 3.27-3.07 (1H, m), 2.28 (3H, s), 1.87 (1.5H, s), 1.84 (1.5H, s).

MS; m/z: 246 (M+H)$^+$

Example 1-4

7-Hydroxy-3,8-dimethyl-2-(1-methylazetidin-3-yl)-4H-chromen-4-one hydrochloride

[Chemical formula 13]

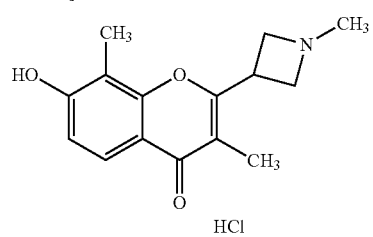

A mixture composed of 2-(azetidin-3-yl)-7-hydroxy-3,8-dimethyl-4H-chromen-4-one (74 mg, 0.30 mmol) obtained in Example 1-3, 90% paraformaldehyde (50 mg, 1.50 mmol), magnesium sulfate (60 mg), and acetic acid (17 μL, 0.30 mmol) was stirred at 50° C. for 10 minutes. Then, sodium cyanoborohydride (44 mg, 0.66 mmol) was added thereto, and the mixture was stirred at 50° C. for 3 hours. Insoluble matter in the reaction solution was filtered off through celite and washed with methanol. The filtrate was concentrated under reduced pressure, and the obtained residue was purified by reverse-phase HPLC. A 1 N aqueous hydrochloric acid solution (4 mL) was added to a fraction containing the compound of interest, and the mixture was concentrated under reduced pressure. Diethyl ether was added to the obtained residue, and the mixture was powdered to obtain 36 mg of the title compound (yield: 39%).

$^1$H-NMR (DMSO-$d_6$) δ: 10.80 (1H, br s), 10.67 (1H, s), 7.73 (1H, d, J=8.7 Hz), 7.00 (1H, d, J=8.7 Hz), 4.67-4.12 (5H, m), 2.93 (3H, br s), 2.33 (3H, s), 1.87 (3H, s).

MS; m/z: 260 (M+H)$^+$

Example 2

7-Hydroxy-3,8-dimethyl-2-[(2R)-1-methylpyrrolidin-2-yl]-4H-chromen-4-one

Example 2-1

1-[2-Hydroxy-4-(methoxymethoxy)-3-methylphenyl]propan-1-one

[Chemical formula 14]

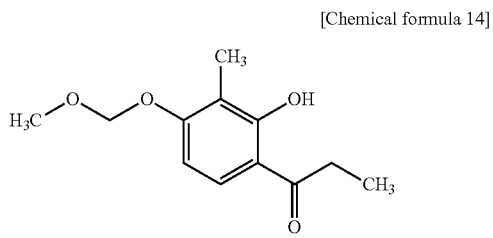 [SMILES: CCC(=O)c1ccc(OCOC)c(C)c1O]

To a mixture composed of 1-(2,4-dihydroxy-3-methylphenyl)propan-1-one (5.00 g, 27.8 mmol) and dichloromethane (80 mL), diisopropylethylamine (5.26 mL, 30.5 mmol) was added under cooling with ice, and then a solution of chloro(methoxy)methane (2.30 mL, 30.5 mmol) in dichloromethane (20 mL) was added dropwise to the mixture over 20 minutes. After the completion of dropwise addition, the mixture was brought back to room temperature and stirred overnight. Dichloromethane was added to the reaction solution. The organic layer was washed with water and then dried over sodium sulfate. The desiccant was filtered off, and then the filtrate was concentrated under reduced pressure. The obtained residue was purified by silica gel column chromatography (n-hexane/ethyl acetate=90/10→70/30) to obtain 5.73 g of the title compound (yield: 92%).

$^1$H-NMR (CDCl$_3$) δ: 7.60 (1H, d, J=9.2 Hz), 6.64 (1H, d, J=9.2 Hz), 5.26 (2H, s), 3.49 (3H, s), 2.98 (2H, q, J=7.3 Hz), 2.14 (3H, s), 1.23 (3H, t, J=7.3 Hz).

Example 2-2

Benzyl (2R)-2-(7-hydroxy-3,8-dimethyl-4-oxo-4H-chromen-2-yl)pyrrolidine-1-carboxylate

[Chemical formula 15]

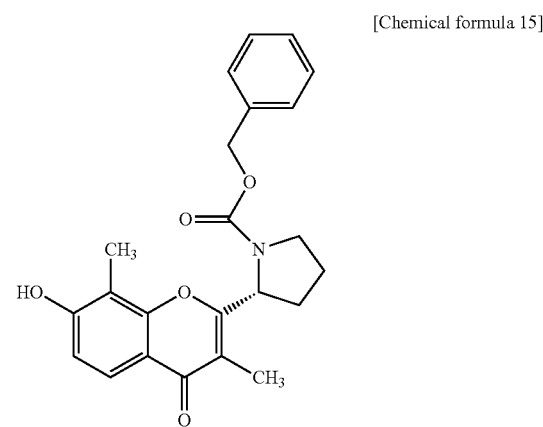 [SMILES: Cc1c([C@H]2CCCN2C(=O)OCc2ccccc2)oc2c(C)c(O)ccc2c1=O]

1-Benzyl 2-[3-(methoxymethoxy)-2-methyl-6-propanoylphenyl](2R)-pyrrolidine-1,2-dicarboxylate (786 mg, yield: 86%) was obtained through the same reaction as in Example 1-1 using 1-[2-hydroxy-4-(methoxymethoxy)-3-methylphenyl]propan-1-one (449 mg, 2.00 mmol) obtained in Example 2-1 and 1-[(benzyloxy)carbonyl]-D-proline (598 mg, 2.40 mmol). Subsequently, the title compound (122 mg, yield: 84%) was obtained through the same reaction as in Example 1-2 using the obtained compound (170 mg, 0.37 mmol).

$^1$H-NMR (CDCl$_3$) δ: 9.29 (1H, br s), 7.93-7.70 (1H, m), 7.41-7.27 (2H, m), 7.09-6.94 (4H, m), 5.22-4.82 (3H, m), 3.85-3.69 (2H, m), 2.45-2.37 (1H, m), 2.24-1.98 (9H, m).

MS; m/z: 394 (M+H)$^+$

Example 2-3

7-Hydroxy-3,8-dimethyl-2-[(2R)-pyrrolidin-2-yl]-4H-chromen-4-one hydrochloride

[Chemical formula 16]

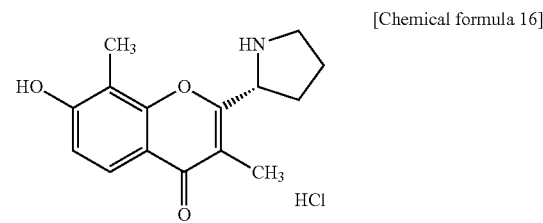 [SMILES: Cc1c([C@H]2CCCN2)oc2c(C)c(O)ccc2c1=O ; Cl]

The title compound (29 mg, yield: 34%) was obtained through the same reaction as in Example 1-3 using benzyl (2R)-2-(7-hydroxy-3,8-dimethyl-4-oxo-4H-chromen-2-yl)pyrrolidine-1-carboxylate (106 mg, 0.27 mmol) obtained in Example 2-2.

$^1$H-NMR (DMSO-$d_6$) δ: 10.74 (1H, s), 10.24-10.15 (1H, br m), 9.38-9.30 (1H, br m), 7.74 (1H, d, J=8.7 Hz), 7.01 (1H, d, J=8.7 Hz), 5.03-4.96 (1H, m), 3.42-3.32 (2H, m), 2.42-2.00 (4H, m), 2.24 (3H, s), 2.04 (3H, s).

MS; m/z: 260 (M+H)$^+$

Example 2-4

7-Hydroxy-3,8-dimethyl-2-[(2R)-1-methylpyrrolidin-2-yl]-4H-chromen-4-one

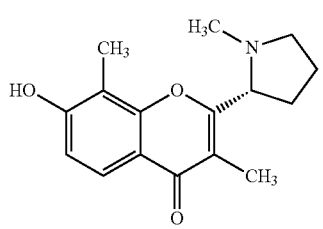

[Chemical formula 17]

A mixture composed of 7-hydroxy-3,8-dimethyl-2-[(2R)-pyrrolidin-2-yl]-4H-chromen-4-one hydrochloride (78 mg, 0.30 mmol) obtained in Example 2-3, 90% paraformaldehyde (50 mg, 1.50 mmol), magnesium sulfate (60 mg), and acetic acid (17 μL, 0.30 mmol) was stirred at 50° C. for 5 minutes. Then, sodium cyanoborohydride (43 mg, 0.66 mmol) was added thereto, and the mixture was stirred at 50° C. for 3 hours. Insoluble matter in the reaction solution was filtered off and then washed with methanol. The filtrate was concentrated under reduced pressure, and the obtained residue was purified by reverse-phase HPLC to obtain 23 mg of the title compound (yield: 27%).

$^1$H-NMR (DMSO-$d_6$) δ: 10.50 (1H, s), 7.71 (1H, d, J=8.7 Hz), 6.92 (1H, d, J=8.7 Hz), 3.70-3.65 (1H, m), 3.13-3.07 (1H, m), 2.43-2.35 (1H, m), 2.25 (3H, s), 2.20 (3H, s), 2.18-1.85 (4H, m), 2.01 (3H, s).

MS; m/z: 274 (M+H)$^+$

Example 3

2-[(2R)-1-Ethylpyrrolidin-2-yl]-7-hydroxy-3,8-dimethyl-4H-chromen-4-one

Example 3-1

2-[(2R)-1-Ethylpyrrolidin-2-yl]-3,8-dimethyl-4-oxo-4H-chromen-7-yl acetate

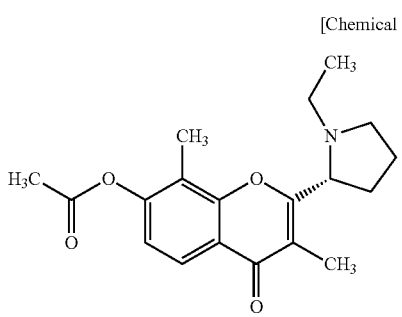

[Chemical formula 18]

To a solution (suspension) of 7-hydroxy-3,8-dimethyl-2-[(2R)-pyrrolidin-2-yl]-4H-chromen-4-one hydrochloride (78 mg, 0.30 mmol) obtained in Example 2-3 and 2,6-lutidine (52 μL, 0.45 mmol) in dimethylformamide (1.5 mL), iodoethane (31 μL, 0.39 mmol) was added dropwise under cooling with ice, and then the mixture was brought back to room temperature and stirred for 6.5 hours. 2,6-Lutidine (105 μL, 0.90 mmol) was added to the reaction solution, and the mixture was cooled with ice again. Then, acetyl chloride (43 μL, 0.60 mmol) was added dropwise thereto, and the mixture was brought back to room temperature and stirred overnight. The reaction solution was concentrated, and then a saturated aqueous solution of sodium bicarbonate was added to the obtained residue, followed by extraction with ethyl acetate. The organic layer was dried over sodium sulfate. The desiccant was filtered off, and then the filtrate was concentrated under reduced pressure. The obtained residue was purified by silica gel column chromatography (chloroform/methanol=100/0→90/10) to obtain 58 mg of the title compound (yield: 59%).

$^1$H-NMR (CDCl$_3$) δ: 8.07 (1H, d, J=8.8 Hz), 7.04 (1H, d, J=8.8 Hz), 3.84-3.80 (1H, m), 3.29-3.24 (1H, m), 2.72-2.62 (1H, m), 2.47-2.33 (2H, m), 2.38 (3H, s), 2.30 (3H, s), 2.22-2.01 (3H, m), 2.14 (3H, s), 1.99-1.88 (1H, m), 1.05 (3H, t, J=7.2 Hz).

MS; m/z: 330 (M+H)$^+$

Example 3-2

2-[(2R)-1-Ethylpyrrolidin-2-yl]-7-hydroxy-3,8-dimethyl-4H-chromen-4-one

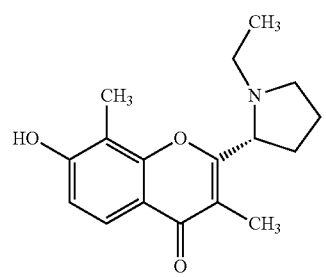

[Chemical formula 19]

Potassium carbonate (97 mg, 0.70 mmol) was added to a solution of 2-[(2R)-1-ethylpyrrolidin-2-yl]-3,8-dimethyl-4-oxo-4H-chromen-7-yl acetate (58 mg, 0.18 mmol) obtained in Example 3-1 in methanol (4 mL), and then the mixture was stirred at room temperature for 2 hours. A 1 N aqueous hydrochloric acid solution (2 mL) was added dropwise thereto, and then methanol in the reaction solution was distilled off under reduced pressure. Water (2 mL) was added to the residue, and then the pH of the mixture was adjusted to around 8 by the dropwise addition of a saturated aqueous solution of sodium bicarbonate, followed by extraction with ethyl acetate. The organic layer was dried over sodium sulfate. The desiccant was filtered off, and then the filtrate was concentrated under reduced pressure. Ethyl acetate and n-hexane were added to the obtained residue, and the mixture was powdered to obtain 40 mg of the title compound (yield: 79%).

$^1$H-NMR (DMSO-$d_6$) δ: 10.49 (1H, s), 7.71 (1H, d, J=8.7 Hz), 6.92 (1H, d, J=8.7 Hz), 3.84-3.79 (1H, m), 3.21-3.15 (1H, m), 2.64-2.55 (1H, m), 2.42-2.32 (2H, m), 2.21 (3H, s), 2.19-2.09 (1H, m), 2.00 (3H, s), 1.99-1.82 (3H, m), 0.98 (3H, t, J=7.3 Hz).

MS; m/z: 288 (M+H)$^+$

Example 4

7-Hydroxy-2-[(2R)-1-(2-hydroxyethyl)pyrrolidin-2-yl]-3,8-dimethyl-4H-chromen-4-one hydrochloride

Example 4-1

7-Hydroxy-3,8-dimethyl-2-{(2R)-1-[2-(tetrahydro-2H-pyran-2-yloxy)ethyl]pyrrolidin-2-yl}-4H-chromen-4-one

[Chemical formula 20]

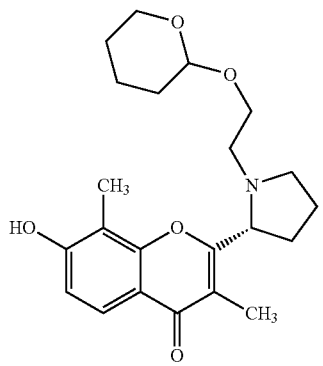

To a solution of 7-hydroxy-3,8-dimethyl-2-[(2R)-pyrrolidin-2-yl]-4H-chromen-4-one hydrochloride (70 mg, 0.27 mmol) obtained in Example 2-3 and triethylamine (56 μL, 0.40 mmol) in dimethylformamide (1.5 mL), 2-(2-bromoethoxy)tetrahydro-2H-pyran (163 μL, 1.08 mmol) was added dropwise, and then the mixture was stirred at room temperature for 20 hours. Triethylamine (38 μL, 0.27 mmol) and 2-(2-bromoethoxy)tetrahydro-2H-pyran (41 μL, 0.27 mmol) were further added dropwise thereto, and then the mixture was stirred at room temperature for 27 hours. The reaction solution was concentrated, and then the obtained residue was purified by silica gel column chromatography (chloroform/methanol=100/0→90/10) to obtain 77 mg of the title compound (yield: 74%).

$^1$H-NMR (CDCl$_3$) δ: 7.82 (1H, d, J=8.7 Hz), 6.86 (1H, d, J=8.7 Hz), 4.57-4.50 (1H, m), 4.04-3.97 (1H, m), 3.87-3.76 (2H, m), 3.56-3.40 (2H, m), 3.38-3.31 (1H, m), 2.96-2.88 (1H, m), 2.75-2.60 (2H, m), 2.29 (3H, s), 2.23-2.07 (6H, m), 2.01-1.93 (1H, m), 1.79-1.59 (2H, m), 1.56-1.41 (4H, m).

MS; m/z: 388 (M+H)$^+$

Example 4

7-Hydroxy-2-[(2R)-1-(2-hydroxyethyl)pyrrolidin-2-yl]-3,8-dimethyl-4H-chromen-4-one hydrochloride

[Chemical formula 21]

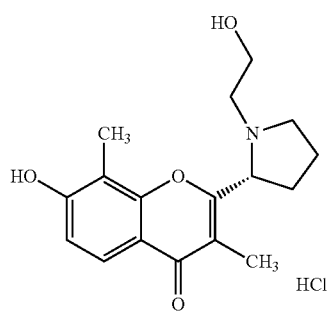

A mixture composed of 7-hydroxy-3,8-dimethyl-2-{(2R)-1-[2-(tetrahydro-2H-pyran-2-yloxy)ethyl]pyrrolidin-2-yl}-4H-chromen-4-one (77 mg, 0.20 mmol) obtained in Example 4-1, methanol (6 mL), concentrated hydrochloric acid (0.5 mL), and water (1 mL) was heated with stirring at a bath temperature of 55° C. for 20 hours. The reaction solution was concentrated under reduced pressure, and the obtained residue was purified by reverse-phase HPLC. A 1 N aqueous hydrochloric acid solution (4 mL) was added to a fraction containing the compound of interest, and then the mixture was concentrated under reduced pressure. Diethyl ether and methanol were added to the obtained residue, and the mixture was powdered. The obtained solid was collected by filtration and then dried in a vacuum pump to obtain 40 mg of the title compound (yield: 53%).

$^1$H-NMR (DMSO-d$_6$) δ: 10.74 (1H, s), 10.25 (1H, br s), 7.74 (1H, d, J=8.7 Hz), 7.02 (1H, d, J=8.7 Hz), 5.18-5.07 (1H, m), 3.91-3.82 (1H, m), 3.77-3.68 (2H, m), 3.42-3.34 (1H, m), 2.57-2.17 (7H, m), 2.31 (3H, s), 2.05 (3H, s).

MS; m/z: 304 (M+H)$^+$

Example 5

7-Hydroxy-3,8-dimethyl-2-[(2S)-1-methylpyrrolidin-2-yl]-4H-chromen-4-one hydrochloride

Example 5-1

Benzyl (2S)-2-[7-(benzyloxy)-3,8-dimethyl-4-oxo-4H-chromen-2-yl]pyrrolidine-1-carboxylate

[Chemical formula 22]

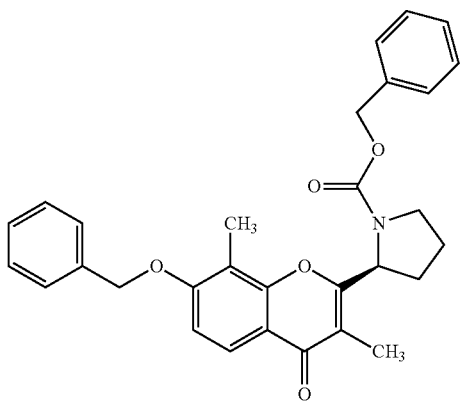

1-Benzyl 2-[3-(benzyloxy)-2-methyl-6-propanoylphenyl] (2S)-pyrrolidine-1,2-dicarboxylate (3.36 g, yield: 91%) was obtained through the same reaction as in Example 1-1 using 1-[4-(benzyloxy)-2-hydroxy-3-methylphenyl]propan-1-one (2.00 g, 7.40 mmol) and 1-[(benzyloxy)carbonyl]-L-proline (2.21 g, 8.88 mmol). Subsequently, the title compound (1.72 g, yield: 53%) was obtained through the same reaction as in Example 1-2 using the obtained compound (3.36 g, 6.70 mmol).

$^1$H-NMR (CDCl$_3$) δ: 8.04-7.97 (1H, m), 7.46-7.31 (7H, m), 7.03-6.97 (4H, m), 5.24-4.83 (5H, m), 3.79-3.70 (2H, m), 2.46-2.31 (1H, m), 2.26-2.12 (5H, m), 2.08-1.98 (1H, m), 1.97 (3H, s).

MS; m/z: 484 (M+H)$^+$

Example 5-2

7-Hydroxy-3,8-dimethyl-2-[(2S)-1-methylpyrrolidin-2-yl]-4H-chromen-4-one hydrochloride

[Chemical formula 23]

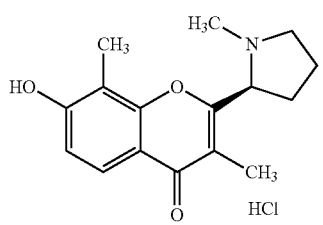

7-Hydroxy-3,8-dimethyl-2-[(2S)-pyrrolidin-2-yl]-4H-chromen-4-one (797 mg, yield: 100%) was obtained through the same reaction as in Example 1-3 using benzyl (2S)-2-[7-(benzyloxy)-3,8-dimethyl-4-oxo-4H-chromen-2-yl]pyrrolidine-1-carboxylate (1.47 g, 3.04 mmol) obtained in Example 5-1. Subsequently, the title compound (74 mg, yield: 55%) was obtained through the same reaction as in Example 1-4 using the obtained compound (113 mg, 0.41 mmol).

$^1$H-NMR (DMSO-$d_6$) δ: 10.79 (1H, br s), 10.73 (1H, s), 7.74 (1H, d, J=8.7 Hz), 7.02 (1H, d, J=8.7 Hz), 5.00-4.93 (1H, m), 3.80-3.71 (1H, m), 3.28-3.19 (1H, m), 2.86 (3H, d, J=5.0 Hz), 2.49-2.32 (2H, m), 2.29 (3H, s), 2.27-2.10 (2H, m), 2.06 (3H, s).

MS; m/z: 274 (M+H)$^+$

Example 6

2-(1-Acetylpiperidin-4-yl)-7-hydroxy-3,8-dimethyl-4H-chromen-4-one

[Chemical formula 24]

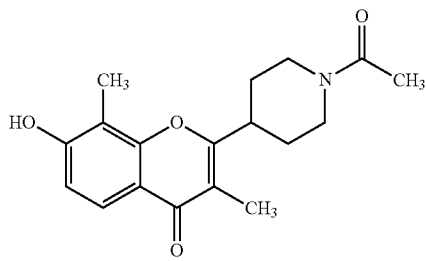

3-(Methoxymethoxy)-2-methyl-6-propanoylphenyl 1-acetylpiperidine-4-carboxylate (633 mg, yield: 100%) was obtained through the same reaction as in Example 1-1 using 1-[2-hydroxy-4-(methoxymethoxy)-3-methylphenyl]propan-1-one (336 mg, 1.50 mmol) obtained in Example 2-1 and 1-acetylpiperidine-4-carboxylic acid (308 mg, 1.80 mmol). Subsequently, the title compound (43 mg, yield: 30%) was obtained through the same reaction as in Example 1-2 using the obtained compound (189 mg, 0.45 mmol).

$^1$H-NMR (DMSO-$d_6$) δ: 10.50 (1H, s), 7.70 (1H, d, J=8.7 Hz), 6.92 (1H, d, J=8.7 Hz), 4.56-4.52 (1H, m), 3.97-3.93 (1H, m), 3.28-3.15 (2H, m), 2.70-2.62 (1H, m), 2.20 (3H, s), 2.05 (3H, s), 1.99 (3H, s), 1.90-1.75 (3H, m), 1.68-1.59 (1H, m).

MS; m/z: 316 (M+H)$^+$

Example 7

Ethyl 4-(7-hydroxy-3,8-dimethyl-4-oxo-4H-chromen-2-yl)piperidine-1-carboxylate

Example 7-1

Benzyl 4-[7-(benzyloxy)-3,8-dimethyl-4-oxo-4H-chromen-2-yl]piperidine-1-carboxylate

[Chemical formula 25]

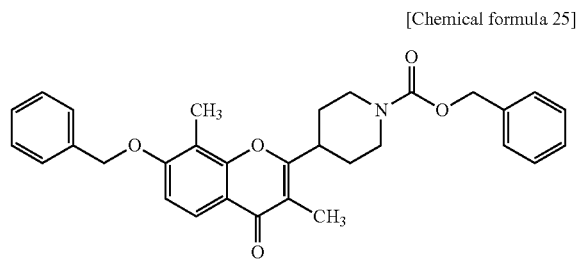 [SMILES: Cc1c(C2CCN(C(=O)OCc3ccccc3)CC2)oc2c(C)c(OCc3ccccc3)ccc2c1=O]

1-Benzyl 4-[3-(benzyloxy)-2-methyl-6-propanoylphenyl] piperidine-1,4-dicarboxylate (6.36 g, yield: 70%) was obtained through the same reaction as in Example 1-1 using 1-[4-(benzyloxy)-2-hydroxy-3-methylphenyl]propan-1-one (4.76 g, 17.61 mmol) and 1-[(benzyloxy)carbonyl]piperidine-4-carboxylic acid (5.56 g, 21.13 mmol). Subsequently, the title compound (5.92 g, yield: 97%) was obtained through the same reaction as in Example 1-2 using the obtained compound (6.36 g, 12.34 mmol).

$^1$H-NMR (CDCl$_3$) δ: 8.02 (1H, d, J=9.2 Hz), 7.46-7.31 (10H, m), 7.00 (1H, d, J=9.2 Hz), 5.21 (2H, s), 5.18 (2H, s), 4.47-4.30 (2H, m), 3.09-2.99 (1H, m), 2.98-2.87 (2H, m), 2.33 (3H, s), 2.08 (3H, s), 2.00-1.81 (4H, m).

MS; m/z: 498 (M+H)$^+$

Example 7-2

7-Hydroxy-3,8-dimethyl-2-(piperidin-4-yl)-4H-chromen-4-one

[Chemical formula 26]

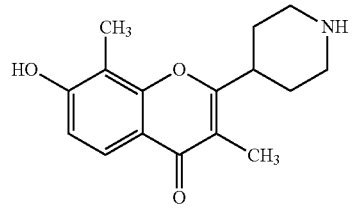

The title compound (3.08 g, yield: 88%) was obtained through the same reaction as in Example 1-3 using benzyl 4-[7-(benzyloxy)-3,8-dimethyl-4-oxo-4H-chromen-2-yl]piperidine-1-carboxylate (5.92 g, 11.9 mmol) obtained in Example 7-1.

$^1$H-NMR (DMSO-$d_6$) δ: 7.69 (1H, d, J=8.7 Hz), 6.90 (1H, d, J=8.7 Hz), 3.07-2.95 (3H, m), 2.65-2.57 (2H, m), 2.23 (3H, s), 1.95 (3H, s), 1.82-1.66 (4H, m).

MS; m/z: 274 (M+H)$^+$

Example 7-3

Ethyl 4-(7-hydroxy-3,8-dimethyl-4-oxo-4H-chromen-2-yl)piperidine-1-carboxylate

[Chemical formula 27]

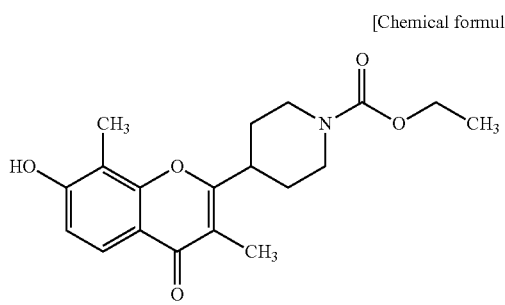

To a solution of 7-hydroxy-3,8-dimethyl-2-(piperidin-4-yl)-4H-chromen-4-one (68 mg, 0.25 mmol) obtained in Example 7-2 and pyridine (22 μL, 0.28 mmol) in dimethylformamide (2 mL), ethyl chlorocarbonate (24 μL, 0.25 mmol) was added dropwise under cooling with ice, and then the mixture was brought back to room temperature and stirred for 2 days. The reaction solution was concentrated, and the obtained residue was purified by reverse-phase HPLC to obtain 60 mg of the title compound (yield: 69%).

$^1$H-NMR (DMSO-$d_6$) δ: 10.51 (1H, s), 7.70 (1H, d, J=8.7 Hz), 6.92 (1H, d, J=8.7 Hz), 4.16-4.09 (2H, m), 4.07 (2H, q, J=7.0 Hz), 3.22-3.13 (1H, m), 3.01-2.86 (2H, m), 2.19 (3H, s), 1.98 (3H, s), 1.85-1.66 (4H, m), 1.21 (3H, t, J=7.0 Hz).

MS; m/z: 346 (M+H)$^+$

Example 8

7-Hydroxy-3,8-dimethyl-2-[1-(methylsulfonyl)piperidin-4-yl]-4H-chromen-4-one

[Chemical formula 28]

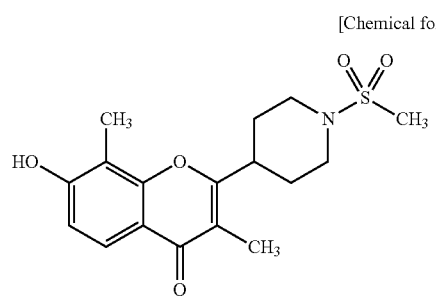

The title compound (31 mg, yield: 35%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and methanesulfonyl chloride (19 μL, 0.25 mmol).

$^1$H-NMR (DMSO-$d_6$) δ: 10.52 (1H, s), 7.71 (1H, d, J=8.7 Hz), 6.93 (1H, d, J=8.7 Hz), 3.73-3.68 (2H, m), 3.15-3.06 (1H, m), 2.92 (3H, s), 2.88 (2H, dd, J=11.2, 3.9 Hz), 2.22 (3H, s), 1.98 (3H, s), 1.95-1.84 (4H, m).

MS; m/z: 352 (M+H)$^+$

Example 9

N-Ethyl-4-(7-hydroxy-3,8-dimethyl-4-oxo-4H-chromen-2-yl)piperidine-1-carboxamide

[Chemical formula 29]

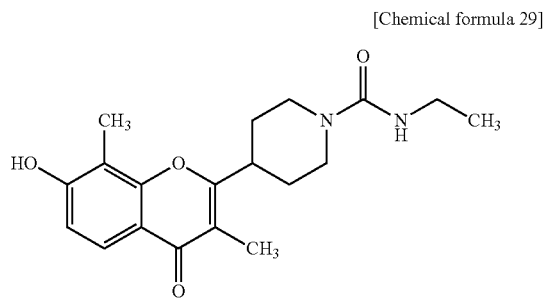 [SMILES: CCNC(=O)N1CCC(c2oc3c(C)c(O)ccc3c(=O)c2C)CC1]

To a solution of 7-hydroxy-3,8-dimethyl-2-(piperidin-4-yl)-4H-chromen-4-one (68 mg, 0.25 mmol) obtained in Example 7-2 in dimethylformamide (2 mL), isocyanatoethane (19 μL, 0.25 mmol) was added dropwise under cooling with ice, and then the mixture was brought back to room temperature and stirred for 2 days. The reaction solution was concentrated, and then the obtained residue was purified by reverse-phase HPLC to obtain 52 mg of the title compound (yield: 59%).

$^1$H-NMR (DMSO-$d_6$) δ: 10.51 (1H, s), 7.70 (1H, d, J=8.7 Hz), 6.92 (1H, d, J=8.7 Hz), 6.52 (1H, t, J=5.3 Hz), 4.09 (2H, m), 3.17-3.03 (3H, m), 2.83-2.75 (2H, m), 2.19 (3H, s), 1.98 (3H, s), 1.79-1.65 (4H, m), 1.03 (3H, t, J=7.1 Hz).

MS; m/z: 345 (M+H)$^+$

Example 10

4-(7-Hydroxy-3,8-dimethyl-4-oxo-4H-chromen-2-yl)-N,N-dimethylpiperidine-1-carboxamide

[Chemical formula 30]

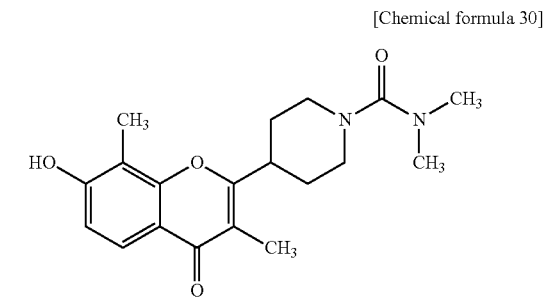 [SMILES: Cc1c(C2CCN(C(=O)N(C)C)CC2)oc2c(C)c(O)ccc2c1=O]

The title compound (34 mg, yield: 40%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and dimethylcarbamic acid chloride (23 μL, 0.25 mmol).

$^1$H-NMR (DMSO-$d_6$) δ: 10.52 (1H, s), 7.70 (1H, d, J=8.7 Hz), 6.92 (1H, d, J=8.7 Hz), 3.67 (2H, d, J=13.3 Hz), 3.19-3.08 (1H, m), 2.90-2.81 (2H, m), 2.76 (6H, s), 2.20 (3H, s), 1.98 (3H, s), 1.88-1.77 (4H, m).

MS; m/z: 345 (M+H)$^+$

Example 11

7-Hydroxy-2-[1-(methoxyacetyl)piperidin-4-yl]-3,8-dimethyl-4H-chromen-4-one

[Chemical formula 31]

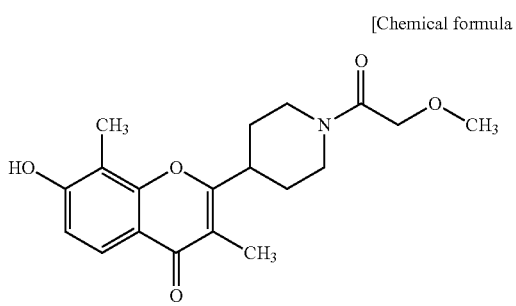

The title compound (40 mg, yield: 47%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and methoxyacetyl chloride (23 μL, 0.25 mmol).

$^1$H-NMR (DMSO-d$_6$) δ: 10.53 (1H, s), 7.70 (1H, d, J=8.7 Hz), 6.92 (1H, d, J=8.7 Hz), 4.50 (1H, d, J=12.8 Hz), 4.20 (1H, d, J=13.8 Hz), 4.07 (1H, d, J=13.8 Hz), 3.90 (1H, d, J=13.8 Hz), 3.31 (3H, s), 3.31-3.10 (2H, m), 2.76-2.68 (1H, m), 2.19 (3H, s), 1.99 (3H, s), 1.86-1.79 (3H, m), 1.71-1.63 (1H, m).

MS; m/z: 346 (M+H)$^+$

Example 12

4-(7-Hydroxy-3,8-dimethyl-4-oxo-4H-chromen-2-yl)-N,N-dimethylpiperidine-1-sulfonamide

[Chemical formula 32]

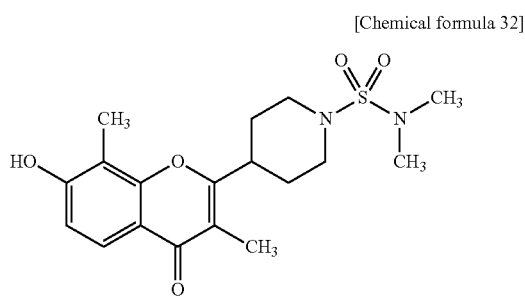 [SMILES: Cc1c(C2CCN(S(=O)(=O)N(C)C)CC2)oc2c(C)c(O)ccc2c1=O]

The title compound (91 mg, yield: 65%) was obtained through the same reaction as in Example 7-3 using 7-hydroxy-3,8-dimethyl-2-(piperidin-4-yl)-4H-chromen-4-one (100 mg, 0.366 mmol) obtained in Example 7-2 and dimethylsulfamyl chloride (55 μL, 0.512 mmol).

$^1$H-NMR (DMSO-d$_6$) δ: 10.50 (1H, s), 7.71 (1H, d, J=8.7 Hz), 6.93 (1H, dd, J=8.7, 2.8 Hz), 3.70 (2H, d, J=12.4 Hz), 3.19-3.11 (1H, m), 3.07-2.99 (2H, m), 2.80 (6H, s), 2.22 (3H, s), 1.97 (3H, s), 1.90-1.83 (4H, m).

MS; m/z: 381 (M+H)$^+$

Example 13

2-(1-Butanoylpiperidin-4-yl)-7-hydroxy-3,8-dimethyl-4H-chromen-4-one

[Chemical formula 33]

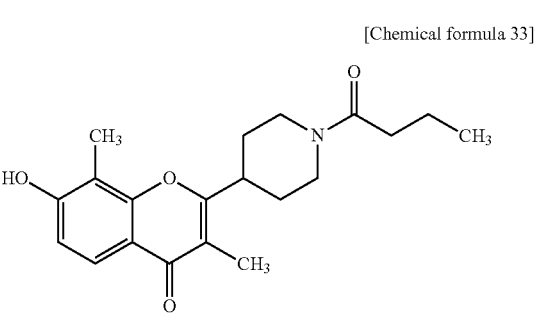 [SMILES: CCCC(=O)N1CCC(c2oc3c(C)c(O)ccc3c(=O)c2C)CC1]

The title compound (50 mg, yield: 23%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and n-butyric acid chloride (28 μL, 0.28 mmol).

$^1$H-NMR (DMSO-d$_6$) δ: 10.53 (1H, s), 7.70 (1H, d, J=8.6 Hz), 6.92 (1H, d, J=8.6 Hz), 4.59-4.55 (1H, m), 4.04-3.99 (1H, m), 3.27-3.13 (2H, m), 2.69-2.62 (1H, m), 2.41-2.27 (2H, m), 2.18 (3H, s), 1.99 (3H, s), 1.88-1.72 (3H, m), 1.68-1.62 (1H, m), 1.59-1.50 (2H, m), 0.91 (3H, t, J=7.4 Hz).

MS; m/z: 344 (M+H)$^+$

Example 14

2-[1-(Ethylsulfonyl)piperidin-4-yl]-7-hydroxy-3,8-dimethyl-4H-chromen-4-one

[Chemical formula 34]

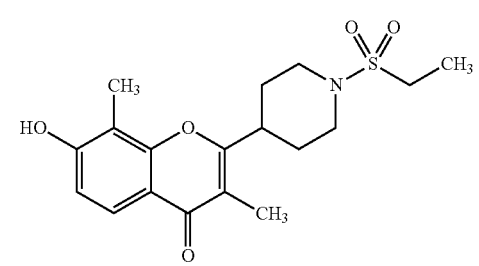

The title compound (28 mg, yield: 30%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and ethanesulfonyl chloride (26 μL, 0.28 mmol).

$^1$H-NMR (DMSO-d$_6$) δ: 10.55 (1H, br s), 7.70 (1H, d, J=8.6 Hz), 6.93 (1H, d, J=8.6 Hz), 3.77-3.72 (2H, m), 3.17-3.08 (3H, m), 3.03-2.96 (2H, m), 2.22 (3H, s), 1.98 (3H, s), 1.93-1.81 (4H, m), 1.25 (3H, t, J=7.4 Hz).

MS; m/z: 366 (M+H)$^+$

Example 15

7-Hydroxy-3,8-dimethyl-2-[1-(3,3,3-trifluoropropanoyl)piperidin-4-yl]-4H-chromen-4-one

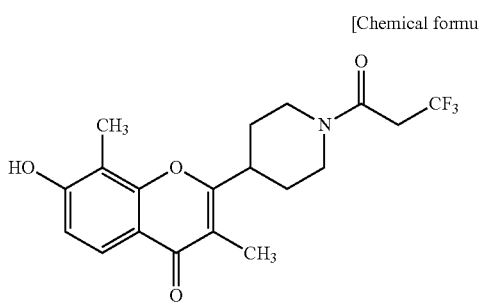

[Chemical formula 35]

A solution of 7-hydroxy-3,8-dimethyl-2-(piperidin-4-yl)-4H-chromen-4-one (68 mg, 0.25 mmol) obtained in Example 7-2, 3,3,3-trifluoropropionic acid (33 μL, 0.30 mmol), 1-ethyl-3-(3-dimethylaminopropyl)carbodiimide hydrochloride (192 mg, 1.00 mmol), and diisopropylethylamine (86 μL, 0.50 mmol) in dimethylformamide (1.5 mL) was stirred at room temperature for 4 hours. The reaction solution was concentrated, and water was added to the obtained residue, followed by extraction with ethyl acetate. The organic layer was dried over sodium sulfate. The desiccant was filtered off, and then the filtrate was concentrated under reduced pressure. The obtained residue was purified by silica gel column chromatography (chloroform/methanol=100/0→95/5) to obtain 13 mg of the title compound (yield: 13%).

$^1$H-NMR (DMSO-$d_6$) δ: 10.53 (1H, br s), 7.70 (1H, d, J=8.7 Hz), 6.92 (1H, d, J=8.7 Hz), 4.57-4.52 (1H, m), 4.02-3.94 (1H, m), 3.84-3.60 (2H, m), 3.31-3.14 (2H, m), 2.78-2.69 (1H, m), 2.19 (3H, s), 1.99 (3H, s), 1.88-1.81 (3H, m), 1.73-1.60 (1H, m).

MS; m/z: 384 (M+H)$^+$

Example 16

7-Hydroxy-3,8-dimethyl-2-(1-propanoylpiperidin-4-yl)-4H-chromen-4-one

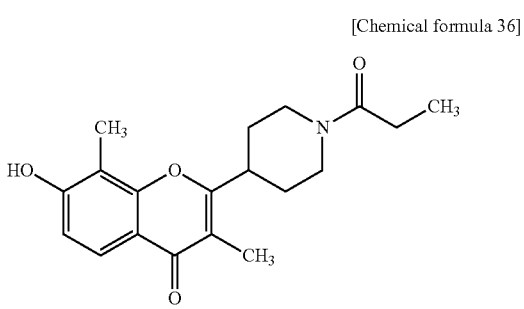 [SMILES: CCC(=O)N1CCC(c2oc3c(C)c(O)ccc3c(=O)c2C)CC1]

[Chemical formula 36]

The title compound (47 mg, yield: 57%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and propionic acid anhydride (35 μL, 0.28 mmol).

$^1$H-NMR (DMSO-$d_6$) δ: 10.52 (1H, br s), 7.70 (1H, d, J=8.7 Hz), 6.92 (1H, d, J=8.7 Hz), 4.60-4.54 (1H, m), 4.03-3.96 (1H, m), 3.27-3.11 (2H, m), 2.71-2.62 (1H, m), 2.42-2.33 (2H, m), 2.19 (3H, s), 1.99 (3H, s), 1.90-1.59 (4H, m), 1.02 (3H, t, J=7.3 Hz).

MS; m/z: 330 (M+H)$^+$

Example 17

7-Hydroxy-3,8-dimethyl-2-[1-(2-methylpropanoyl)piperidin-4-yl]-4H-chromen-4-one

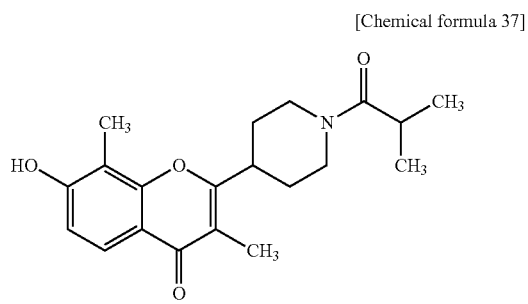 [SMILES: Cc1c(C2CCN(C(=O)C(C)C)CC2)oc2c(C)c(O)ccc2c1=O]

[Chemical formula 37]

The title compound (49 mg, yield: 57%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and 2-methylpropionic acid chloride (46 μL, 0.28 mmol).

$^1$H-NMR (DMSO-$d_6$) δ: 10.51 (1H, br s), 7.70 (1H, d, J=8.7 Hz), 6.92 (1H, d, J=8.7 Hz), 4.61-4.54 (1H, m), 4.13-4.07 (1H, m), 3.30-3.15 (2H, m), 2.99-2.90 (1H, m), 2.71-2.62 (1H, m), 2.17 (3H, s), 1.99 (3H, s), 1.93-1.58 (4H, m), 1.06-0.99 (6H, m).

MS; m/z: 344 (M+H)$^+$

Example 18

2-[1-(2,2-Dimethylpropanoyl)piperidin-4-yl]-7-hydroxy-3,8-dimethyl-4H-chromen-4-one

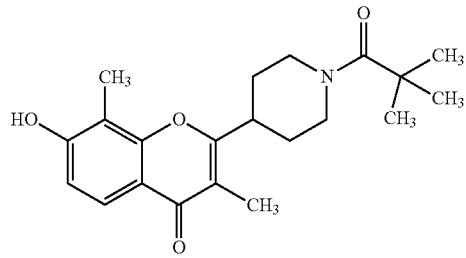

[Chemical formula 38]

The title compound (21 mg, yield: 23%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and pivaloyl chloride (33 μL, 0.28 mmol).

$^1$H-NMR (DMSO-$d_6$) δ: 10.50 (1H, br s), 7.70 (1H, d, J=8.7 Hz), 6.92 (1H, d, J=8.7 Hz), 4.47-4.41 (2H, m), 3.32-3.23 (1H, m), 2.99-2.90 (2H, m), 2.17 (3H, s), 1.99 (3H, s), 1.89-1.82 (2H, m), 1.77-1.66 (2H, m), 1.23 (9H, s).

MS; m/z: 358 (M+H)$^+$

Example 19

7-Hydroxy-3,8-dimethyl-2-[1-(phenylcarbonyl)piperidin-4-yl)-4H-chromen-4-one

[Chemical formula 39]

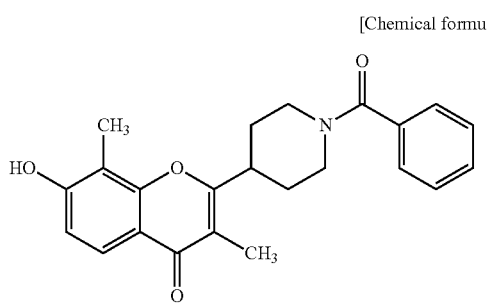

The title compound (50 mg, yield: 52%) was obtained through the same reaction as in Example 7-3 using 7-hydroxy-3,8-dimethyl-2-(piperidin-4-yl)-4H-chromen-4-one (68 mg, 0.25 mmol) obtained in Example 7-2 and benzoyl chloride (32 μL, 0.28 mmol).

$^1$H-NMR (DMSO-d$_6$) δ: 10.50 (1H, s), 7.71 (1H, d, J=8.7 Hz), 7.49-7.41 (5H, m), 6.93 (1H, d, J=8.7 Hz), 4.72-4.60 (1H, m), 3.76-3.63 (1H, m), 3.32-3.24 (2H, m), 3.00-2.90 (1H, m), 2.24 (3H, s), 1.99 (3H, s), 1.95-1.75 (4H, m).

MS; m/z: 378 (M+H)$^+$

Example 20

7-Hydroxy-3,8-dimethyl-2-[1-(1,3-thiazol-2-yl)piperidin-4-yl]-4H-chromen-4-one

[Chemical formula 40]

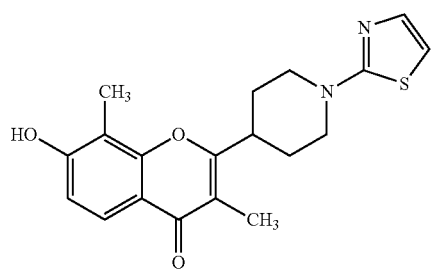

A solution of 7-hydroxy-3,8-dimethyl-2-(piperidin-4-yl)-4H-chromen-4-one (68 mg, 0.25 mmol) obtained in Example 7-2, 2-bromothiazole (45 μL, 0.28 mmol), and 1,8-diazabicyclo[5.4.0]undec-7-ene (56 μL, 0.38 mmol) in N-methylpyrrolidone (0.2 mL) was heated with stirring at 140° C. for 12 hours. The reaction solution was allowed to cool and then purified by silica gel column chromatography (chloroform/methanol=100/0→95/5) to obtain 24 mg of the title compound (yield: 27%).

$^1$H-NMR (DMSO-d$_6$) δ: 10.49 (1H, s), 7.71 (1H, d, J=8.7 Hz), 7.18 (1H, d, J=3.7 Hz), 6.92 (1H, d, J=8.7 Hz), 6.85 (1H, d, J=3.7 Hz), 4.06-4.01 (2H, m), 3.29-3.12 (3H, m), 2.17 (3H, s), 2.00 (3H, s), 1.98-1.90 (4H, m).

MS; m/z: 357 (M+H)$^+$

Example 21

7-Hydroxy-3,8-dimethyl-2-[1-(pyridin-2-yl)piperidin-4-yl]-4H-chromen-4-one

[Chemical formula 41]

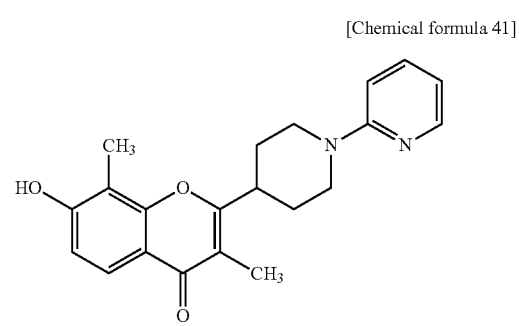 [SMILES: Cc1c(C2CCN(c3ccccn3)CC2)oc2c(C)c(O)ccc2c1=O]

The title compound (53 mg, yield: 61%) was obtained through the same reaction as in Example 20 using 7-hydroxy-3,8-dimethyl-2-(piperidin-4-yl)-4H-chromen-4-one (68 mg, 0.25 mmol) obtained in Example 7-2 and 2-bromopyridine (43 μL, 0.28 mmol).

$^1$H-NMR (DMSO-d$_6$) δ: 10.47 (1H, s), 8.14-8.12 (1H, m), 7.70 (1H, d, J=8.7 Hz), 7.56-7.52 (1H, m), 6.93-6.87 (2H, m), 6.65-6.61 (1H, m), 4.50-4.43 (2H, m), 3.28-3.16 (1H, m), 2.97-2.88 (2H, m), 2.13 (3H, s), 2.01 (3H, s), 1.91-1.80 (4H, m).

MS; m/z: 351 (M+H)$^+$

Example 22

7-Hydroxy-3,8-dimethyl-2-[1-(pyrazin-2-yl)piperidin-4-yl]-4H-chromen-4-one

[Chemical formula 42]

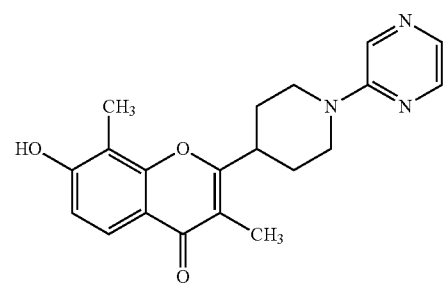

The title compound (29 mg, yield: 33%) was obtained through the same reaction as in Example 20 using 7-hydroxy-3,8-dimethyl-2-(piperidin-4-yl)-4H-chromen-4-one (68 mg, 0.25 mmol) obtained in Example 7-2 and 2-chloropyrazine (32 mg, 0.28 mmol).

$^1$H-NMR (DMSO-d$_6$) δ: 10.47 (1H, br s), 8.40 (1H, s), 8.11-8.09 (1H, m), 7.84-7.83 (1H, m), 7.70 (1H, d, J=8.7 Hz), 6.92 (1H, d, J=8.7 Hz), 4.54-4.49 (2H, m), 3.34-3.26 (1H, m), 3.06-2.98 (2H, m), 2.13 (3H, s), 2.01 (3H, s), 1.95-1.81 (4H, m).

MS; m/z: 352 (M+H)$^+$

Example 23

4-{[4-(7-Hydroxy-3,8-dimethyl-4-oxo-4H-chromen-2-yl)piperidin-1-yl]methyl}-N-methylbenzamide

Example 23-1

Methyl 4-{[4-(7-hydroxy-3,8-dimethyl-4-oxo-4H-chromen-2-yl)piperidin-1-yl]methyl}benzoate

[Chemical formula 43]

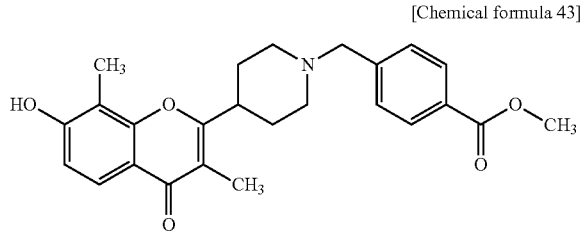 [SMILES: COC(=O)c1ccc(CN2CCC(c3oc4c(C)c(O)ccc4c(=O)c3C)CC2)cc1]

The title compound (145 mg, yield: 38%) was obtained as an oil through the same reaction as in Example 4-1 using 7-hydroxy-3,8-dimethyl-2-(piperidin-4-yl)-4H-chromen-4-one (250 mg, 0.91 mmol) obtained in Example 7-2 and methyl 4-(bromomethyl)benzoate (251 mg, 1.10 mmol).

$^1$H-NMR (CDCl$_3$) δ: 8.02 (2H, d, J=8.3 Hz), 7.92 (1H, d, J=8.7 Hz), 7.45 (2H, d, J=8.3 Hz), 6.89 (1H, d, J=8.7 Hz), 3.92 (3H, s), 3.63 (2H, s), 3.09-3.03 (2H, m), 2.93-2.85 (1H, m), 2.34 (3H, s), 2.20-2.05 (7H, m), 1.95-1.78 (2H, m).

MS; m/z: 422 (M+H)$^+$

Example 23-2

4-{[4-(7-Hydroxy-3,8-dimethyl-4-oxo-4H-chromen-2-yl)piperidin-1-yl]methyl}benzoic acid

[Chemical formula 44]

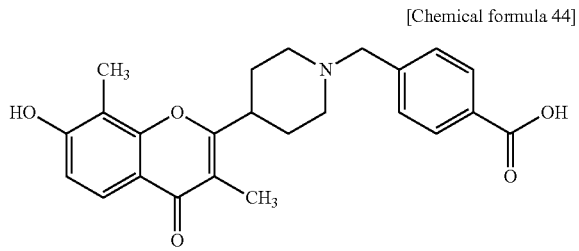 [SMILES: Cc1c(C2CCN(Cc3ccc(C(=O)O)cc3)CC2)oc2c(C)c(O)ccc2c1=O]

A 1 N aqueous sodium hydroxide solution (4 mL) was added to a solution of methyl 4-{[4-(7-hydroxy-3,8-dimethyl-4-oxo-4H-chromen-2-yl)piperidin-1-yl]methyl}benzoate (140 mg, 0.33 mmol) obtained in Example 23-1 in methanol (4 mL), and the mixture was heated with stirring at a bath temperature of 50° C. for 4 hours. Methanol in the reaction solution was distilled off under reduced pressure. Then, a 1 N aqueous hydrochloric acid solution (4 mL) and water (10 mL) were added to the residue, and insoluble matter was collected by filtration to obtain 125 mg of the title compound (yield: 89%).

MS; m/z: 408 (M+H)$^+$

Example 23-3

4-{[4-(7-Hydroxy-3,8-dimethyl-4-oxo-4H-chromen-2-yl)piperidin-1-yl]methyl}-N-methylbenzamide

[Chemical formula 45]

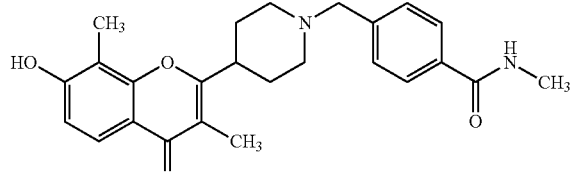

The title compound (42 mg, yield: 64%) was obtained through the same reaction as in Example 15 using 4-[[4-(7-hydroxy-3,8-dimethyl-4-oxo-4H-chromen-2-yl)piperidin-1-yl]methyl]benzoic acid (62 mg, 0.15 mmol) obtained in Example 23-2, methylamine hydrochloride (54 mg, 0.76 mmol), and diisopropylethylamine (157 μL, 0.91 mmol).

$^1$H-NMR (DMSO-d$_6$) δ: 10.49 (1H, s), 8.41-8.37 (1H, m), 7.80 (2H, d, J=7.8 Hz), 7.70 (1H, d, J=8.7 Hz), 7.41 (2H, d, J=7.8 Hz), 6.92 (1H, d, J=8.7 Hz), 3.56 (2H, s), 2.97-2.89 (3H, m), 2.78 (3H, d, J=4.1 Hz), 2.23 (3H, s), 2.14-2.06 (2H, m), 1.95 (3H, s), 1.94-1.85 (2H, m), 1.80-1.76 (2H, m).

MS; m/z: 421 (M+H)$^+$

Example 24

4-[[4-(7-Hydroxy-3,8-dimethyl-4-oxo-4H-chromen-2-yl)piperidin-1-yl]methyl]-N,N-dimethylbenzamide

[Chemical formula 46]

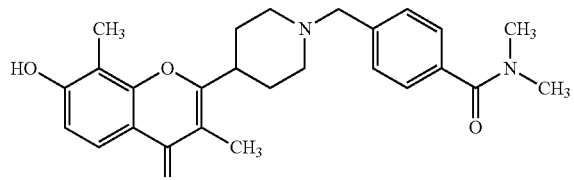

The title compound (33 mg, yield: 55%) was obtained through the same reaction as in Example 15 using 4-{[4-(7-hydroxy-3,8-dimethyl-4-oxo-4H-chromen-2-yl)piperidin-1-yl]methyl}benzoic acid (62 mg, 0.15 mmol) obtained in Example 23-2, dimethylamine hydrochloride (65 mg, 0.76 mmol), and diisopropylethylamine (157 μL, 0.91 mmol).

$^1$H-NMR (DMSO-d$_6$) δ: 10.49 (1H, s), 7.70 (1H, d, J=8.7 Hz), 7.41-7.35 (4H, m), 6.92 (1H, d, J=8.7 Hz), 3.55 (2H, s), 3.01-2.88 (9H, m), 2.23 (3H, s), 2.14-2.08 (2H, m), 1.95 (3H, s), 1.94-1.86 (2H, m), 1.81-1.76 (2H, m).

MS; m/z: 435 (M+H)$^+$

Example 25

2-(1-Acetylpiperidin-3-yl)-7-hydroxy-3,8-dimethyl-4H-chromen-4-one

Example 25-1

Benzyl 3-[7-(benzyloxy)-3,8-dimethyl-4-oxo-4H-chromen-2-yl]piperidine-1-carboxylate

[Chemical formula 47]

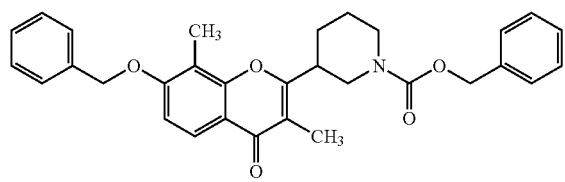

1-Benzyl 3-[3-(benzyloxy)-2-methyl-6-propanoylphenyl]piperidine-1,3-dicarboxylate (5.42 g, yield: 91%) was obtained through the same reaction as in Example 1-1 using 1-[4-(benzyloxy)-2-hydroxy-3-methylphenyl]propan-1-one (3.20 g, 11.84 mmol) and 1-[(benzyloxy)carbonyl]piperidine-3-carboxylic acid (4.05 g, 21.13 mmol). Subsequently, the title compound (2.75 g, yield: 53%) was obtained through the same reaction as in Example 1-2 using the obtained compound (5.42 g, 10.5 mmol).

$^1$H-NMR (CDCl$_3$) δ: 8.02 (1H, d, J=8.7 Hz), 7.47-7.31 (10H, m), 7.01 (1H, d, J=8.7 Hz), 5.22-5.12 (4H, m), 4.48-4.22 (2H, m), 3.19-2.82 (3H, m), 2.34 (3H, s), 2.13-1.56 (7H, m).

MS; m/z: 498 (M+H)$^+$

Example 25-2

2-(1-Acetylpiperidin-3-yl)-7-hydroxy-3,8-dimethyl-4H-chromen-4-one

[Chemical formula 48]

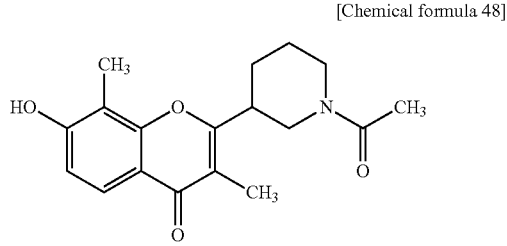 [SMILES: CC(=O)N1CCCC(c2oc3c(C)c(O)ccc3c(=O)c2C)C1]

7-Hydroxy-3,8-dimethyl-2-(piperidin-3-yl)-4H-chromen-4-one (1.24 g, yield: 82%) was obtained through the same reaction as in Example 1-3 using benzyl 3-[7-(benzyloxy)-3,8-dimethyl-4-oxo-4H-chromen-2-yl]piperidine-1-carboxylate (2.75 g, 5.53 mmol) obtained in Example 25-1. Subsequently, the title compound (50 mg, yield: 61%) was obtained through the same reaction as in Example 7-3 using the obtained compound (68 mg, 0.25 mmol) and acetic anhydride (26 µL, 0.28 mmol).

$^1$H-NMR (DMSO-d$_6$) δ: 10.51-10.51 (1H, m), 7.71 (1H, d, J=8.7 Hz), 6.93 (1H, d, J=8.7 Hz), 4.55-4.41 (1H, m), 4.01-3.85 (1H, m), 3.40-2.56 (6H, m), 2.24-2.22 (3H, m), 2.06-1.72 (6H, m), 1.65-1.41 (1H, m).

MS; m/z: 316 (M+H)$^+$

Example 26

7-Hydroxy-3,8-dimethyl-2-{1-[4-(morpholin-4-yl-carbonyl)benzyl]piperidin-3-yl}-4H-chromen-4-one

Example 26-1

Benzyl 3-[7-hydroxy-3,8-dimethyl-4-oxo-4H-chromen-2-yl]piperidine-1-carboxylate

[Chemical formula 49]

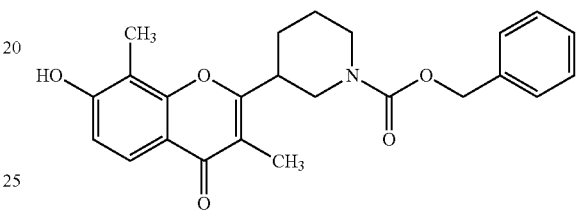

Benzyl 3-[3-(methoxymethoxy)-2-methyl-6-propanoylphenyl]piperidine-1,3-dicarboxylate (55.4 g, yield: 100%) was obtained through the same reaction as in Example 1-1 using 1-[2-hydroxy-4-(methoxymethoxy)-3-methylphenyl]propan-1-one (26.4 g, 118.98 mmol) obtained in Example 2-1 and 1-[(benzyloxy)carbonyl]piperidine-3-carboxylic acid (37.3 g, 141.58 mmol). Subsequently, the title compound (19.7 g, yield: 43%) was obtained through the same reaction as in Example 1-2 using the obtained compound (52.8 g, 112.44 mmol).

$^1$H-NMR (CDCl$_3$) δ: 7.91 (1H, d, J=8.7 Hz), 7.49 (1H, br s), 7.37-7.35 (5H, br m), 6.93 (1H, d, J=8.7 Hz), 5.19 (1H, d, J=12.4 Hz), 5.14 (1H, d, J=12.4 Hz), 4.47-4.21 (2H, m), 3.20-2.98 (2H, m), 2.95-2.81 (1H, m), 2.32 (3H, s), 2.13-2.01 (4H, m), 1.99-1.81 (2H, m), 1.71-1.57 (1H, m).

Example 26-2

7-(Methoxymethoxy)-3,8-dimethyl-2-piperidin-3-yl-4H-chromen-4-one

[Chemical formula 50]

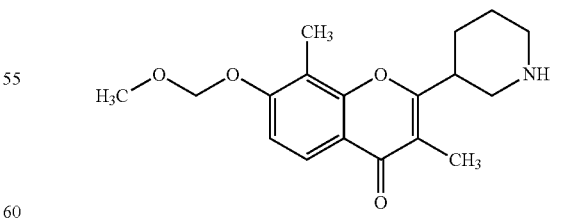

The title compound (22.7 g, yield: 100%) was obtained through the same reaction as in Example 2-1 using benzyl 3-[7-hydroxy-3,8-dimethyl-4-oxo-4H-chromen-2-yl]piperidine-1-carboxylate (28.5 g, 70.00 mmol) obtained in Example 26-1 and chloro(methoxy)methane (6.32 mL, 84.0 mmol) and subsequently the same reaction as in 1-3.

¹H-NMR (CDCl₃) δ: 8.01 (1H, d, J=8.7 Hz), 7.13 (1H, d, J=8.7 Hz), 5.30 (2H, s), 3.51 (3H, s), 3.24-3.19 (1H, m), 3.17-3.12 (1H, m), 3.09-2.96 (2H, m), 2.71 (1H, td, J=12.4, 2.8 Hz), 2.35 (3H, s), 2.09 (3H, s), 2.05-1.98 (1H, m), 1.96-1.80 (2H, m), 1.71-1.55 (2H, m).

Example 26-3

Methyl 4-({3-[7-(methoxymethoxy)-3,8-dimethyl-4-oxo-4H-chromen-2-yl]piperidin-1-yl}methyl)benzoate

[Chemical formula 51]

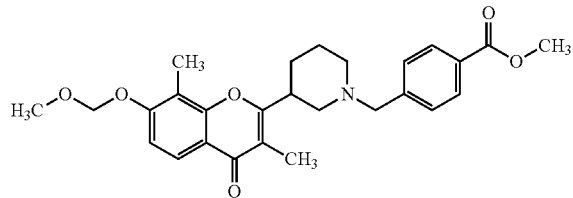

The title compound (450 mg, yield: 82%) was obtained through the same reaction as in Example 4-1 using 7-(methoxymethoxy)-3,8-dimethyl-2-(piperidin-3-yl)-4H-chromen-4-one (376 mg, 1.18 mmol) obtained in Example 26-2 and methyl 3-(bromomethyl)benzoate (378 mg, 1.65 mmol).

¹H-NMR (CDCl₃) δ: 8.00 (3H, d, J=8.7 Hz), 7.42 (2H, d, J=8.3 Hz), 7.12 (1H, d, J=8.7 Hz), 5.29 (2H, s), 3.91 (3H, s), 3.62 (2H, s), 3.50 (3H, s), 3.25-3.17 (1H, m), 3.02-2.92 (2H, m), 2.35 (1H, t, J=11.0 Hz), 2.33 (3H, s), 2.10-2.03 (1H, m), 2.05 (3H, s), 1.98-1.91 (1H, m), 1.85-1.66 (3H, m).

Example 26-4

7-Hydroxy-3,8-dimethyl-2-{1-[4-(morpholin-4-ylcarbonyl)benzyl]piperidin-3-yl}-4H-chromen-4-one

[Chemical formula 52]

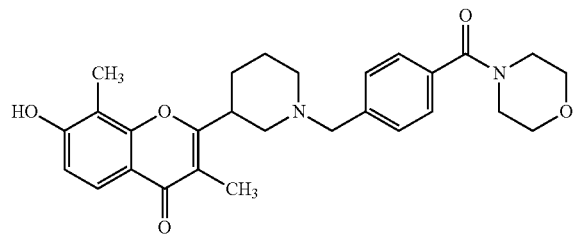

4-({3-[7-(Methoxymethoxy)-3,8-dimethyl-4-oxo-4H-chromen-2-yl]piperidin-1-yl}methyl)benzoic acid (412 mg, yield: 94%) was obtained through the same ester hydrolysis reaction as in Example 23-2 using methyl 4-({3-[7-(methoxymethoxy)-3,8-dimethyl-4-oxo-4H-chromen-2-yl]piperidin-1-yl}methyl)benzoate (450 mg, 0.97 mmol) obtained in Example 26-3. Subsequently, 7-(methoxymethoxy)-3,8-dimethyl-2-{1-[4-(morpholin-4-ylcarbonyl)benzyl]piperidin-3-yl}-4H-chromen-4-one (89 mg, yield: 78%) was obtained through the same reaction as in Example 15 using the obtained carboxylic acid compound (99 mg, 0.22 mmol) and morpholine (38 mg, 0.44 mmol). Further, the title compound (68 mg, yield: 83%) was obtained through the same reaction as in Example 37-5 using the obtained amide compound (89 mg, 0.17 mmol).

¹H-NMR (DMSO-d₆) δ: 10.50 (1H, s), 7.69 (1H, d, J=8.6 Hz), 7.39 (2H, d, J=8.0 Hz), 7.36 (2H, d, J=8.0 Hz), 6.92 (1H, d, J=8.6 Hz), 3.68-3.50 (8H, m), 3.35-3.30 (2H, m), 3.18-3.11 (1H, m), 3.00-2.95 (1H, m), 2.90-2.84 (1H, m), 2.31 (1H, t, J=10.9 Hz), 2.20 (3H, s), 2.04-1.97 (1H, m), 1.94-1.86 (1H, m), 1.92 (3H, s), 1.78-1.60 (3H, m).

MS; m/z: 477 (M+H)⁺

Example 27

4-{[3-(7-Hydroxy-3,8-dimethyl-4-oxo-4H-chromen-2-yl)piperidin-1-yl]methyl}benzamide

[Chemical formula 53]

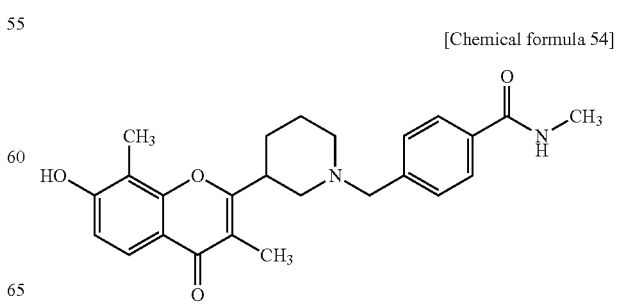

4-({3-[7-(Methoxymethoxy)-3,8-dimethyl-4-oxo-4H-chromen-2-yl]piperidin-1-yl}methyl)benzamide (66 mg, yield: 60%) was obtained through the same reaction as in Example 15 using 4-({3-[7-(methoxymethoxy)-3,8-dimethyl-4-oxo-4H-chromen-2-yl]piperidin-1-yl}methyl)benzoic acid (110 mg, 0.25 mmol) obtained through ester hydrolysis reaction in Example 26-3, ammonium chloride (67 mg, 1.25 mmol), and diisopropylethylamine (259 μL, 1.50 mmol). Subsequently, the title compound (18 mg, yield: 30%) was obtained through the same reaction as in Example 37-5 using the obtained compound (66 mg, 0.15 mmol).

¹H-NMR (DMSO-d₆) δ: 8.16 (1H, s), 7.92 (1H, br s), 7.83 (2H, d, J=8.0 Hz), 7.69 (1H, d, J=8.6 Hz), 7.39 (2H, d, J=8.0 Hz), 7.30 (1H, s), 6.92 (1H, d, J=8.6 Hz), 3.62 (1H, d, J=13.7 Hz), 3.58 (1H, d, J=13.7 Hz), 3.18-3.11 (1H, m), 2.99-2.95 (1H, m), 2.88-2.83 (1H, m), 2.54-2.45 (1H, m), 2.31 (1H, t, J=10.9 Hz), 2.21 (3H, s), 2.04-1.98 (1H, m), 1.94-1.87 (1H, m), 1.92 (3H, s), 1.68-1.62 (2H, m).

MS; m/z: 407 (M+H)⁺

Example 28

4-{[3-(7-Hydroxy-3,8-dimethyl-4-oxo-4H-chromen-2-yl)piperidin-1-yl]methyl}-N-methylbenzamide

[Chemical formula 54]

4-({3-[7-(Methoxymethoxy)-3,8-dimethyl-4-oxo-4H-chromen-2-yl]piperidin-1-yl}methyl)-N-methylbenzamide (81 mg, yield: 70%) was obtained through the same reaction as in Example 15 using 4-({3-[7-(methoxymethoxy)-3,8-dimethyl-4-oxo-4H-chromen-2-yl]piperidin-1-yl}methyl) benzoic acid (110 mg, 0.25 mmol) obtained through hydrolysis reaction in Example 26-4, methylamine hydrochloride (84 mg, 1.25 mmol), and diisopropylethylamine (259 μL, 1.50 mmol). Subsequently, the title compound (36 mg, yield: 50%) was obtained through the same reaction as in Example 37-5 using the obtained compound (81 mg, 0.17 mmol).

$^1$H-NMR (DMSO-d$_6$) δ: 10.52 (1H, br s), 8.39 (1H, br s), 7.78 (2H, d, J=6.9 Hz), 7.69 (1H, d, J=8.6 Hz), 7.40 (2H, d, J=6.9 Hz), 6.93 (1H, d, J=8.6 Hz), 3.35-3.30 (2H, m), 3.18-3.10 (1H, m), 3.00-2.93 (1H, m), 2.89-2.83 (1H, m), 2.77 (3H, d, J=3.4 Hz), 2.34-2.26 (1H, m), 2.21 (3H, br s), 2.04-1.88 (6H, m), 1.68-1.60 (2H, m).

MS; m/z: 421 (M+H)$^+$

Example 29

4-[[3-(7-Hydroxy-3,8-dimethyl-4-oxo-4H-chromen-2-yl)piperidin-1-yl]methyl]-N,N-dimethylbenzamide

[Chemical formula 55]

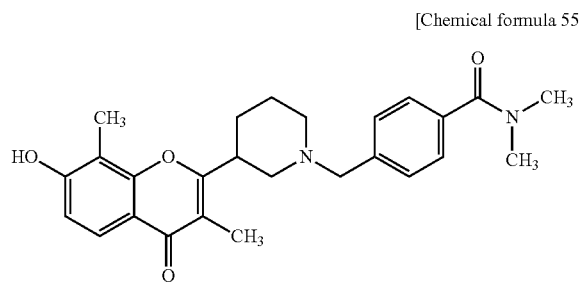

Methyl 4-{[3-(7-hydroxy-3,8-dimethyl-4-oxo-4H-chromen-2-yl)piperidin-1-yl]methyl}benzoate (281 mg, yield: 98%) was obtained through the same reaction as in Example 37-5 using methyl 4-({3-[7-(methoxymethoxy)-3,8-dimethyl-4-oxo-4H-chromen-2-yl]piperidin-1-yl}methyl) benzoate (317 mg, 0.68 mmol) obtained in Example 26-3.

Subsequently, 4-{[3-(7-hydroxy-3,8-dimethyl-4-oxo-4H-chromen-2-yl)piperidin-1-yl]methyl}benzoic acid (204 mg, yield: 88%) was obtained through the same reaction as in Example 23-2 using the obtained ester compound (240 mg, 0.57 mmol). Further, the title compound (18 mg, yield: 24%) was obtained through the same reaction as in Example 15 using the obtained carboxylic acid compound (69 mg, 0.17 mmol), dimethylamine hydrochloride (69 mg, 0.85 mmol), and diisopropylethylamine (178 μL, 1.02 mmol).

$^1$H-NMR (DMSO-d$_6$) δ: 10.52 (1H, s), 7.69 (1H, d, J=8.7 Hz), 7.38 (2H, d, J=8.3 Hz), 7.35 (2H, d, J=8.3 Hz), 6.92 (1H, d, J=8.7 Hz), 3.61 (1H, d, J=13.8 Hz), 3.56 (1H, d, J=13.8 Hz), 3.18-3.10 (1H, m), 3.01-2.84 (8H, m), 2.31 (1H, t, J=11.0 Hz), 2.20 (3H, s), 2.05-1.97 (1H, m), 1.93-1.87 (1H, m), 1.92 (3H, s), 1.79-1.61 (3H, m).

MS; m/z: 435 (M+H)$^+$

Example 30

2-[3-(7-Hydroxy-3,8-dimethyl-4-oxo-4H-chromen-2-yl)piperidin-1-yl]-N-[4-(morpholin-4-ylmethyl)phenyl]acetamide Example 30-1

Ethyl {3-[7-(methoxymethoxy)-3,8-dimethyl-4-oxo-4H-chromen-2-yl]piperidin-1-yl}acetate

[Chemical formula 56]

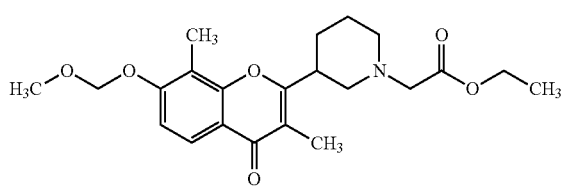

The title compound (445 mg, yield: 87%) was obtained through the same reaction as in Example 4-1 using 7-(methoxymethoxy)-3,8-dimethyl-2-(piperidin-3-yl)-4H-chromen-4-one (401 mg, 1.26 mmol) obtained in Example 26-2 and ethyl bromoacetate (316 mg, 1.89 mmol).

$^1$H-NMR (CDCl$_3$) δ: 8.01 (1H, d, J=8.7 Hz), 7.13 (1H, d, J=8.7 Hz), 5.29 (2H, s), 4.20 (2H, q, J=7.2 Hz), 3.50 (3H, s), 3.32-3.24 (3H, m), 3.09-3.00 (2H, m), 2.57 (1H, t, J=11.0 Hz), 2.34 (3H, s), 2.33-2.25 (1H, m), 2.09 (3H, s), 1.99-1.92 (1H, m), 1.87-1.68 (3H, m), 1.28 (3H, t, J=7.1 Hz).

Example 30-2

2-[3-(7-Hydroxy-3,8-dimethyl-4-oxo-4H-chromen-2-yl)piperidin-1-yl]-N-[4-(morpholin-4-ylmethyl)phenyl]acetamide

[Chemical formula 57]

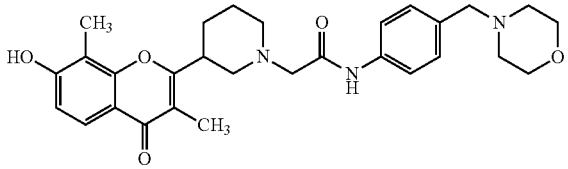

The title compound (48 mg, overall yield: 9%) was obtained through the use of the same reaction as in Example 26-4 using ethyl {3-[7-(methoxymethoxy)-3,8-dimethyl-4-oxo-4H-chromen-2-yl]piperidin-1-yl}acetate (440 mg, 1.09 mmol) obtained in Example 30-1 and 4-(morpholin-4-ylmethyl)aniline (124 mg, 1.26 mmol).

$^1$H-NMR (DMSO-d$_6$) δ: 10.54 (1H, s), 9.71 (1H, s), 7.70 (1H, d, J=8.6 Hz), 7.60-7.57 (2H, m), 7.23 (2H, d, J=8.6 Hz), 6.92 (1H, d, J=8.6 Hz), 3.55 (4H, t, J=4.6 Hz), 3.39 (2H, s), 3.34-3.26 (2H, m), 3.22 (1H, d, J=15.5 Hz), 3.17 (1H, d, J=15.5 Hz), 3.05-3.01 (1H, m), 2.95-2.90 (1H, m), 2.32 (4H, br s), 2.27-2.19 (1H, m), 2.21 (3H, s), 1.98 (3H, s), 1.94-1.89 (1H, m), 1.80-1.74 (2H, m), 1.71-1.62 (1H, m).

MS; m/z: 506 (M+H)$^+$

Example 31

8-Allyl-7-hydroxy-3-methyl-2-(1-propanoylpiperidin-4-yl)-4H-chromen-4-one

Example 31-1

Benzyl 4-(7-hydroxy-3-methyl-4-oxo-4H-chromen-2-yl)piperidine-1-carboxylate

[Chemical formula 58]

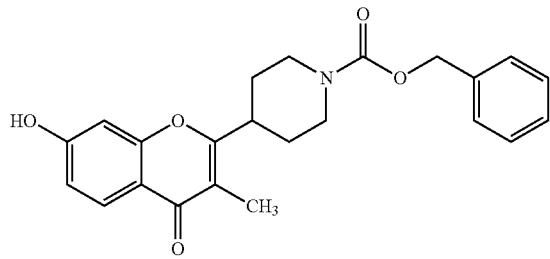

1-Benzyl 4-[5-(methoxymethoxy)-2-propanoylphenyl]piperidine-1,4-dicarboxylate (18.67 g, yield: 100%) was obtained through the same reaction as in Example 1-1 using 1-[2-hydroxy-4-(methoxymethoxy)phenyl]propan-1-one (8.62 g, 41.0 mmol) and 1-[(benzyloxy)carbonyl]piperidine-4-carboxylic acid (12.95 g, 49.2 mmol). Subsequently, the title compound (7.06 g, yield: 44%) was obtained through the same reaction as in Example 1-2 using the obtained compound (18.67 g, 41.0 mmol).

$^1$H-NMR (CDCl$_3$) δ: 8.17-8.15 (1H, m), 8.08 (1H, d, J=8.7 Hz), 7.40-7.30 (5H, m), 6.85 (1H, d, J=2.3 Hz), 6.81 (1H, dd, J=8.7, 2.3 Hz), 5.20 (2H, s), 4.41-4.36 (2H, m), 3.07-2.98 (1H, m), 2.95-2.89 (2H, m), 2.08 (3H, s), 1.93-1.84 (2H, m), 1.81-1.76 (2H, m).

MS; m/z: 394 (M+H)$^+$

Example 31-2

7-Hydroxy-3-methyl-2-(1-propanoylpiperidin-4-yl)-4H-chromen-4-one

[Chemical formula 59]

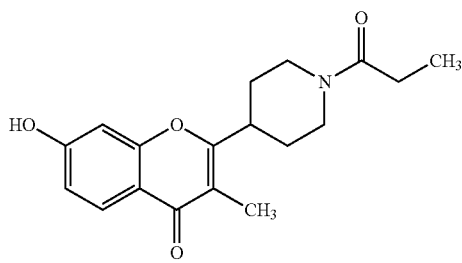

The title compound (2.55 g, yield: 63%) was obtained by sequentially performing the same reactions as in Example 1-3 and Example 7-3 using benzyl 4-(7-hydroxy-3-methyl-4-oxo-4H-chromen-2-yl)piperidine-1-carboxylate (5.07 g, 12.9 mmol) obtained in Example 31-1 and propionic acid anhydride (1.74 mL, 13.5 mmol).

$^1$H-NMR (DMSO-d$_6$) δ: 10.65 (1H, s), 7.84 (1H, d, J=8.7 Hz), 6.86 (1H, dd, J=8.7, 2.3 Hz), 6.77 (1H, d, J=2.3 Hz), 4.56-4.53 (1H, m), 4.00-3.95 (1H, m), 3.24-3.10 (2H, m), 2.69-2.62 (1H, m), 2.40-2.34 (2H, m), 1.98 (3H, s), 1.83-1.70 (3H, m), 1.68-1.58 (1H, m), 1.01 (3H, t, J=7.4 Hz).

MS; m/z: 316 (M+H)$^+$

Example 31-3

7-(Allyloxy)-3-methyl-2-(1-propanoylpiperidin-4-yl)-4H-chromen-4-one

[Chemical formula 60]

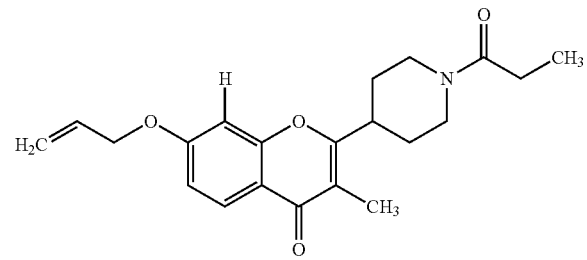

A solution of 7-hydroxy-3-methyl-2-(1-propanoylpiperidin-4-yl)-4H-chromen-4-one (1.00 g, 3.17 mmol) obtained in Example 31-2, allyl bromide (560 µL, 6.34 mmol), and potassium carbonate (613 mg, 4.44 mmol) in acetone (20 mL) was heated with stirring at a bath temperature of 55° C. for 20 hours. Water was added to the reaction solution, followed by extraction with ethyl acetate. The organic layer was dried over magnesium sulfate. The desiccant was filtered off, and then the filtrate was concentrated under reduced pressure to obtain 947 mg of the title compound (yield: 84%).

$^1$H-NMR (CDCl$_3$) δ: 8.09 (1H, d, J=9.2 Hz), 6.95 (1H, dd, J=9.2, 2.3 Hz), 6.78 (1H, d, J=2.3 Hz), 6.12-6.01 (1H, m), 5.46 (1H, d, J=17.4 Hz), 5.35 (1H, d, J=10.5 Hz), 4.89-4.82 (1H, m), 4.62 (2H, d, J=5.0 Hz), 4.06-4.00 (1H, m), 3.21-3.05 (2H, m), 2.70-2.62 (1H, m), 2.42 (2H, q, J=7.5 Hz), 2.09 (3H, s), 1.99-1.81 (4H, m), 1.20 (3H, t, J=7.5 Hz).

MS; m/z: 356 (M+H)$^+$

Example 31-4

8-Allyl-7-hydroxy-3-methyl-2-(1-propanoylpiperidin-4-yl)-4H-chromen-4-one

[Chemical formula 61]

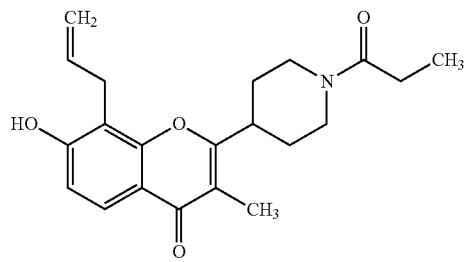

A solution of 7-(allyloxy)-3-methyl-2-(1-propanoylpiperidin-4-yl)-4H-chromen-4-one (920 mg, 2.59 mmol) obtained in Example 31-3 in dimethylaniline (4 mL) was heated with stirring at 200° C. for 6 hours. A 1 N aqueous hydrochloric acid solution (100 mL) was added to the reaction solution, followed by extraction with ethyl acetate. The organic layer was dried over magnesium sulfate. The desiccant was filtered off, and then the filtrate was concentrated under reduced pressure. The obtained residue was purified by silica gel column chromatography (chloroform/methanol=100/0→95/5) to obtain 798 mg of the title compound (yield: 87%).

$^1$H-NMR (CDCl$_3$) δ: 8.37 (1H, s), 7.97 (1H, d, J=8.7 Hz), 7.02 (1H, d, J=8.7 Hz), 6.02-5.91 (1H, m), 5.05-5.04 (1H, m), 5.02-5.00 (1H, m), 4.89-4.84 (1H, m), 4.08-4.02 (1H, m), 3.61 (2H, d, J=5.5 Hz), 3.22-3.08 (2H, m), 2.72-2.63 (1H, m), 2.48-2.41 (2H, m), 2.11 (3H, s), 1.93-1.87 (4H, m), 1.21 (3H, t, J=7.3 Hz).

MS; m/z: 356 (M+H)$^+$

Example 32

8-Bromo-7-hydroxy-3-methyl-2-(1-propanoylpiperidin-4-yl)-4H-chromen-4-one

[Chemical formula 62]

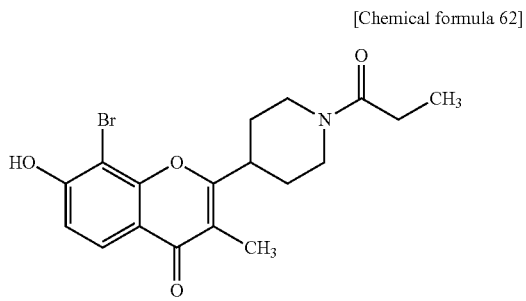

N-Bromosuccinimide (171 mg, 0.96 mmol) was added to a solution of 7-hydroxy-3-methyl-2-(1-propanoylpiperidin-4-yl)-4H-chromen-4-one (304 mg, 0.96 mmol) obtained in Example 31-3 in N,N-dimethylformamide (5 mL), and the mixture was stirred at room temperature for 5 hours. Water was added to the reaction solution, followed by extraction with ethyl acetate. The organic layer was washed with water and saturated brine and dried over anhydrous sodium sulfate, and then the solvent was distilled off under reduced pressure. The obtained residue was purified by silica gel column chromatography (dichloromethane/methanol=98/2→67/33) to obtain 204 mg of the title compound (yield: 54%).

$^1$H-NMR (CD$_3$OD) δ: 7.87 (1H, dd, J=8.7, 1.6 Hz), 6.95 (1H, d, J=8.7 Hz), 5.48 (1H, s), 4.74-4.67 (1H, br m), 4.16-4.09 (1H, br m), 3.35-3.22 (2H, m), 2.82-2.74 (1H, m), 2.53-2.41 (2H, m), 2.07 (3H, s), 2.03-1.89 (4H, m), 1.15 (3H, t, J=7.6 Hz).

MS; m/z: 394 (M+H)$^+$

Example 33

8-Cyclopropyl-7-hydroxy-3-methyl-2-(1-propanoylpiperidin-4-yl)-4H-chromen-4-one

Example 33-1

8-Cyclopropyl-7-(methoxymethoxy)-3-methyl-2-(1-propanoylpiperidin-4-yl)-4H-chromen-4-one

[Chemical formula 63]

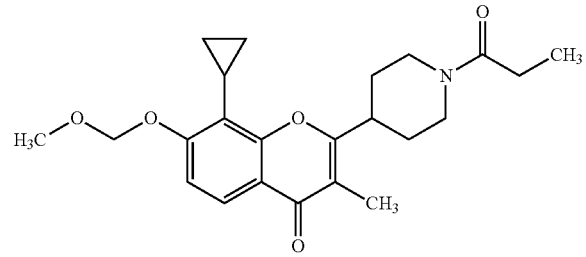

To a solution of 8-bromo-7-hydroxy-3-methyl-2-(1-propanoylpiperidin-4-yl)-4H-chromen-4-one (3.82 mol) obtained in Example 32 in dichloromethane (25 mL), diisopropylethylamine (1.32 mL, 7.66 mmol) and chloro(methoxy)methane (345 μL, 4.59 mmol) were added under cooling with ice, and the mixture was stirred for 1 hour under cooling with ice and then at room temperature for 2 hours. Water was added to the reaction solution, followed by extraction with dichloromethane. The organic layer was washed with saturated brine and dried over anhydrous sodium sulfate, and then the solvent was distilled off under reduced pressure. The obtained residue was purified by silica gel column chromatography (dichloromethane/methanol=98/2) to obtain 847 mg of 8-bromo-7-(methoxymethoxy)-3-methyl-2-(1-propanoylpiperidin-4-yl)-4H-chromen-4-one (yield: 51%). Subsequently, 2-cyclopropyl-4,4,5,5-tetramethyl-1,3,2-dioxaborolane (181 μL, 0.953 mmol), potassium carbonate (167 mg, 1.21 mmol), and a palladium chloride-dppf complex (40.7 mg) were added to a mixed solution of the obtained compound (104 mg, 0.24 mmol) in N,N-dimethylformamide (2 mL) and water (0.2 mL), and the mixture was stirred at 90° C. for 14 hours under the nitrogen atmosphere. Water was added to the reaction solution, followed by extraction with ethyl acetate. The organic layer was washed with water and saturated brine and dried over anhydrous sodium sulfate, and then the solvent was distilled off under reduced pressure. The obtained residue was purified by silica gel column chromatography (n-hexane/ethyl acetate=50/50→0/100) and then further purified by HPLC to obtain 38 mg of the title compound (yield: 40%) as an oil.

$^1$H-NMR (CDCl$_3$) δ: 8.11 (1H, s), 8.02 (1H, d, J=8.7 Hz), 7.12 (1H, d, J=8.7 Hz), 5.29 (2H, s), 4.91-4.84 (1H, br m), 4.09-4.03 (1H, br m), 3.52 (3H, s), 3.23-3.09 (2H, m), 2.67 (1H, td, J=12.8, 3.5 Hz), 2.44 (2H, ddd, J=15.0, 7.5, 2.2 Hz), 2.10 (3H, s), 2.03-1.81 (4H, m), 1.21 (3H, t, J=7.6 Hz), 1.06-0.97 (2H, m), 0.89-0.81 (2H, m).

Example 33-2

8-Cyclopropyl-7-hydroxy-3-methyl-2-(1-propanoylpiperidin-4-yl)-4H-chromen-4-one

[Chemical formula 64]

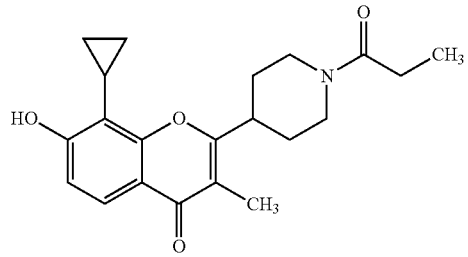

The title compound (27 mg, yield: 79%) was obtained through the same reaction as in Example 37-5 using 8-cyclopropyl-7-(methoxymethoxy)-3-methyl-2-(1-propanoylpiperidin-4-yl)-4H-chromen-4-one (38 mg, 0.10 mol) obtained in Example 33-1.

$^1$H-NMR (DMSO-d$_6$) δ: 10.34 (1H, s), 7.70 (1H, d, J=8.7 Hz), 6.89 (1H, d, J=8.7 Hz), 4.59-4.53 (1H, br m), 4.04-3.97 (1H, br m), 3.29-3.12 (2H, m), 2.66 (1H, td, J=12.7, 2.1 Hz), 2.43-2.30 (2H, m), 1.98 (3H, s), 1.90-1.76 (4H, m), 1.76-1.62 (1H, m), 1.02 (3H, t, J=7.6 Hz), 0.94-0.79 (4H, m).

MS; m/z: 356 (M+H)$^+$

Example 34

8-(Cyclopropylmethyl)-7-hydroxy-3-methyl-2-(1-propanoylpiperidin-4-yl)-4H-chromen-4-one

Example 34-1

7-Hydroxy-3-methyl-4-oxo-2-(1-propanoylpiperidin-4-yl)-4H-chromene-8-carbaldehyde

[Chemical formula 65]

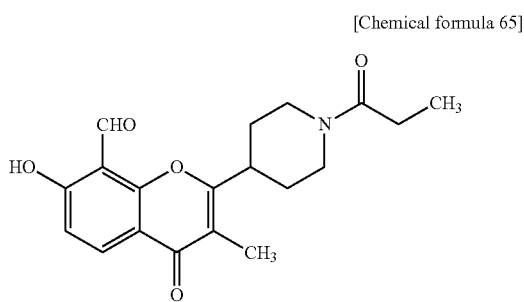 [SMILES: CCC(=O)N1CCC(c2oc3c(C=O)c(O)ccc3c(=O)c2C)CC1]

A solution of 7-hydroxy-3-methyl-2-(1-propanoylpiperidin-4-yl)-4H-chromen-4-one (1.07 g, 3.39 mmol) obtained in Example 31-2 and hexamethylenetetramine (3.33 g, 23.75 mmol) in acetic acid (20 mL) was heated with stirring at 100° C. for 3 hours. The reaction solution was concentrated under reduced pressure. Water (16 mL) and concentrated hydrochloric acid (8 mL) were added to the obtained residue, and the mixture was heated with stirring at a bath temperature of 80° C. for 1 hour. The reaction solution was allowed to cool, and then water was added thereto, followed by extraction with ethyl acetate. The organic layer was dried over magnesium sulfate. The desiccant was filtered off, and then the filtrate was concentrated under reduced pressure. The obtained residue was purified by silica gel column chromatography (n-hexane/ethyl acetate=40/60→0/100) to obtain 584 mg of the title compound (yield: 50%).

$^1$H-NMR (CDCl$_3$) δ: 12.38 (1H, s), 10.51 (1H, s), 8.32 (1H, d, J=9.2 Hz), 6.96 (1H, d, J=9.2 Hz), 4.94-4.87 (1H, m), 4.11-4.03 (1H, m), 3.22-3.09 (2H, m), 2.70-2.61 (1H, m), 2.42 (2H, q, J=7.5 Hz), 2.12 (3H, s), 1.98-1.78 (4H, m), 1.20 (3H, t, J=7.5 Hz).

MS; m/z: 344 (M+H)$^+$

Example 34-2

7-(Benzyloxy)-3-methyl-4-oxo-2-(1-propanoylpiperidin-4-yl)-4H-chromene-8-carbaldehyde

[Chemical formula 66]

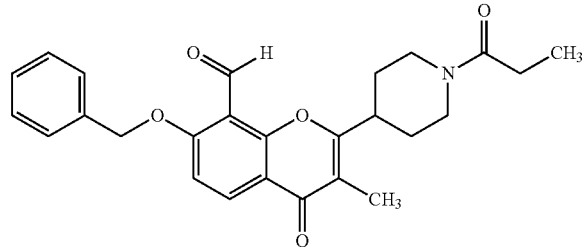

A solution of 7-hydroxy-3-methyl-4-oxo-2-(1-propanoylpiperidin-4-yl)-4H-chromene-8-carbaldehyde (250 mg, 0.73 mmol) obtained in Example 34-1, benzyl bromide (260 μL, 3.64 mmol), and potassium carbonate (503 mg, 3.64 mmol) in dimethylformamide (4 mL) was stirred at room temperature for 26 hours. Water was added to the reaction solution, followed by extraction with ethyl acetate. The organic layer was washed with water and then dried over sodium sulfate. The desiccant was filtered off, and then the filtrate was concentrated under reduced pressure. Diethyl ether and n-hexane were added to the obtained residue. Then, the supernatant was removed by decantation to obtain 305 mg of the title compound (yield: 97%).

$^1$H-NMR (CDCl$_3$) δ: 10.65 (1H, s), 8.37 (1H, d, J=8.7 Hz), 7.47-7.35 (5H, m), 7.11 (1H, d, J=8.7 Hz), 5.32 (2H, s), 4.89-4.82 (1H, m), 4.11-4.05 (1H, m), 3.18-3.03 (2H, m), 2.69-2.61 (1H, m), 2.54-2.34 (2H, m), 2.28-2.16 (1H, m), 2.10 (3H, s), 2.01-1.80 (3H, m), 1.21 (3H, t, J=7.6 Hz).

MS; m/z: 444 (M+H)$^+$

Example 34-3

7-(Benzyloxy)-8-[cyclopropyl(hydroxy)methyl]-3-methyl-2-(1-propanoylpiperidin-4-yl)-4H-chromen-4-one

[Chemical formula 67]

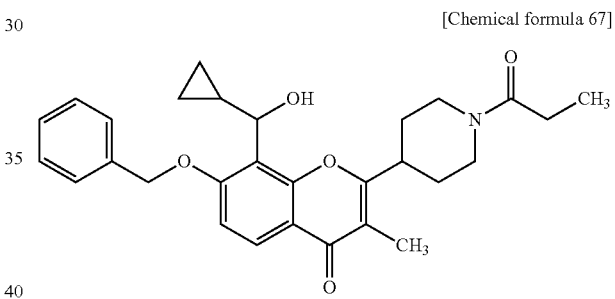

To a solution of 7-(benzyloxy)-3-methyl-4-oxo-2-(1-propanoylpiperidin-4-yl)-4H-chromene-8-carbaldehyde (200 mg, 0.46 mmol) obtained in Example 34-2 in tetrahydrofuran (6 mL), a 1 N solution of cyclopropyl magnesium bromide in tetrahydrofuran (1.5 mL, 1.50 mmol) was added dropwise at −30° C., and the mixture was gradually heated to 0° C. over 45 minutes and then stirred at 0° C. for 2 hours. A 1 N aqueous hydrochloric acid solution (5 mL) was added dropwise to the reaction solution, and then water was added to the mixture, followed by extraction with ethyl acetate. The organic layer was dried over sodium sulfate. The desiccant was filtered off, and then the filtrate was concentrated under reduced pressure. The obtained residue was purified by silica gel column chromatography (n-hexane/ethyl acetate=60/40→0/100) to obtain 159 mg of the title compound (yield: 68%) as an oil.

$^1$H-NMR (CDCl$_3$) δ: 8.13 (1H, d, J=8.7 Hz), 7.45-7.37 (5H, m), 7.11-7.07 (1H, m), 5.27-5.25 (2H, m), 4.91-4.82 (1H, m), 4.64-4.56 (1H, m), 4.07-4.00 (1H, m), 3.52-3.32 (1H, m), 3.21-3.06 (2H, m), 2.66-2.60 (1H, m), 2.46-2.37 (2H, m), 2.10 (3H, s), 1.93-1.73 (4H, m), 1.54-1.50 (1H, m), 1.20 (3H, t, J=7.6 Hz), 0.67-0.61 (1H, m), 0.48-0.38 (2H, m), 0.28-0.22 (1H, m).

Example 34-4

7-(Benzyloxy)-8-(cyclopropylmethyl)-3-methyl-2-(1-propanoylpiperidin-4-yl)-4H-chromen-4-one

[Chemical formula 68]

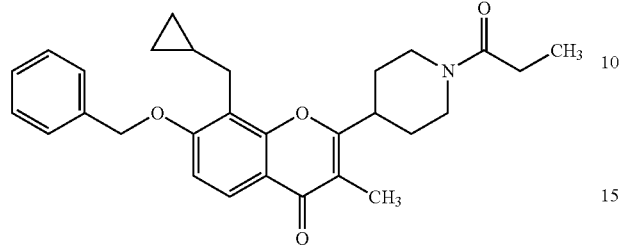

To a solution of 7-(benzyloxy)-8-[cyclopropyl(hydroxy)methyl]-3-methyl-2-(1-propanoylpiperidin-4-yl)-4H-chromen-4-one (100 mg, 0.21 mmol) obtained in Example 34-3 in dichloromethane (2 mL), triethylsilane (336 µL, 2.10 mmol) was added dropwise under cooling with ice. Then, trifluoroacetic acid (79 µL, 1.05 mmol) was added dropwise thereto, and the mixture was stirred for 15 minutes under cooling with ice and then at room temperature for 1 hour. Trifluoroacetic acid (79 µL, 1.05 mmol) was added dropwise to the reaction solution, and the mixture was further stirred at room temperature for 2 hours. The reaction solution was cooled with ice, and then a saturated aqueous solution of sodium bicarbonate (30 mL) was added dropwise thereto, followed by extraction with dichloromethane. The organic layer was dried over sodium sulfate. The desiccant was filtered off, and then the filtrate was concentrated under reduced pressure. The obtained residue was purified by NH silica gel column chromatography (n-hexane/ethyl acetate=98/2→0/100). The title compound (62 mg, yield: 64%) was obtained as an oil.

$^1$H-NMR (CDCl$_3$) δ: 8.05 (1H, d, J=8.7 Hz), 7.45-7.33 (5H, m), 7.02 (1H, d, J=8.7 Hz), 5.20 (2H, s), 4.89-4.85 (1H, m), 4.07-4.02 (1H, m), 3.21-3.07 (2H, m), 2.87-2.78 (2H, m), 2.70-2.61 (1H, m), 2.47-2.38 (2H, m), 2.10 (3H, s), 1.95-1.84 (4H, m), 1.21 (3H, t, J=7.6 Hz), 1.09-1.02 (1H, m), 0.42-0.37 (2H, m), 0.20-0.18 (2H, m).

MS; m/z: 460 (M+H)$^+$

Example 34-5

8-(Cyclopropylmethyl)-7-hydroxy-3-methyl-2-(1-propanoylpiperidin-4-yl)-4H-chromen-4-one

[Chemical formula 69]

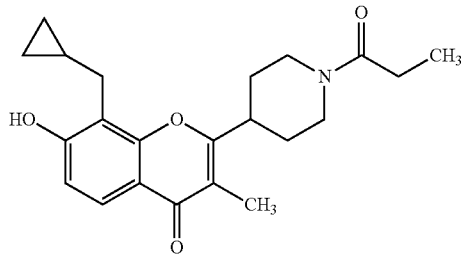

The title compound (32 mg, yield: 64%) was obtained through the same reaction as in Example 1-3 using 7-(benzyloxy)-8-(cyclopropylmethyl)-3-methyl-2-(1-propanoylpiperidin-4-yl)-4H-chromen-4-one (62 mg, 0.13 mmol) obtained in Example 34-4.

$^1$H-NMR (DMSO-d$_6$) δ: 10.50 (1H, s), 7.72 (1H, d, J=8.7 Hz), 6.93 (1H, d, J=8.7 Hz), 4.57-4.52 (1H, m), 4.02-3.97 (1H, m), 3.29-3.13 (2H, m), 2.70-2.63 (3H, m), 2.42-2.29 (2H, m), 1.99 (3H, s), 1.89-1.54 (4H, m), 1.06-1.01 (4H, m), 0.38-0.33 (2H, m), 0.17-0.13 (2H, m).

MS; m/z: 370 (M+H)$^+$

Example 35

8-(4,5-Dihydro-1,3-oxazol-2-yl)-7-hydroxy-3-methyl-2-(1-propanoylpiperidin-4-yl)-4H-chromen-4-one

Example 35-1

7-(Benzyloxy)-3-methyl-4-oxo-2-(1-propanoylpiperidin-4-yl)-4H-chromene-8-carboxylic acid

[Chemical formula 70]

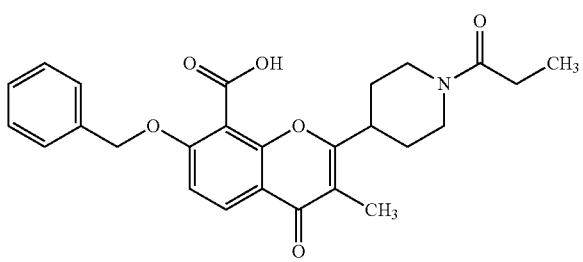

To a mixture composed of 7-(benzyloxy)-3-methyl-4-oxo-2-(1-propanoylpiperidin-4-yl)-4H-chromene-8-carbaldehyde (400 mg, 0.92 mmol) obtained in Example 34-2, tert-butyl alcohol (8 mL), water (8 mL), 2-methyl-2-butene (8 mL), and sodium dihydrogen phosphate dihydrate (864 mg, 5.54 mmol), 80% sodium chlorite (313 mg, 2.77 mmol) was added under cooling with ice, and then the mixture was brought back to room temperature and stirred for 19 hours. A 0.2 N aqueous hydrochloric acid solution (20 mL) was added to the reaction solution, and then the organic solvent was distilled off under reduced pressure. The resulting solid was collected by filtration to obtain 407 mg of the title compound (yield: 95%).

MS; m/z: 450 (M+H)$^+$

Example 35-2

7-(Benzyloxy)-N-(2-hydroxyethyl)-3-methyl-4-oxo-2-(1-propanoylpiperidin-4-yl)-4H-chromene-8-carboxamide

[Chemical formula 71]

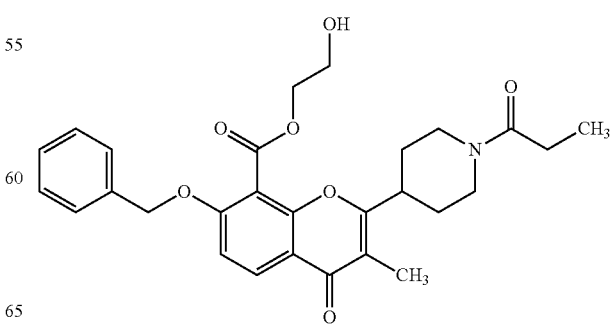

To a solution of 7-(benzyloxy)-3-methyl-4-oxo-2-(1-propanoylpiperidin-4-yl)-4H-chromene-8-carboxylic acid (200 mg, 0.44 mmol) obtained in Example 35-1 in dichloromethane (4 mL), thionyl chloride (97 µL, 1.33 mmol) was added dropwise under cooling with ice. Then, a catalytic amount of dimethylformamide was added dropwise thereto, and the mixture was brought back to room temperature and stirred for 15 hours. The reaction solution was concentrated under reduced pressure, and then the residue was subjected to azeotropy with toluene (2 mL). Dichloromethane (4 mL) was added to the obtained residue. Triethylamine (93 µL, 0.67 mmol) and 2-aminoethanol (53 µL, 0.89 mmol) were added dropwise thereto under cooling with ice, and then the mixture was brought back to room temperature and stirred for 8 hours. Water was added to the reaction solution, followed by extraction with dichloromethane. Then, the organic layer was dried over sodium sulfate. The desiccant was filtered off, and then the filtrate was concentrated under reduced pressure. The obtained residue was purified by silica gel column chromatography (chloroform/methanol=100/0→95/5) to obtain 144 mg of the title compound (yield: 66%).

MS; m/z: 493 (M+H)$^+$

Example 35-3

7-(Benzyloxy)-8-(4,5-dihydro-1,3-oxazol-2-yl)-3-methyl-2-(1-propanoylpiperidin-4-yl)-4H-chromen-4-one

[Chemical formula 72]

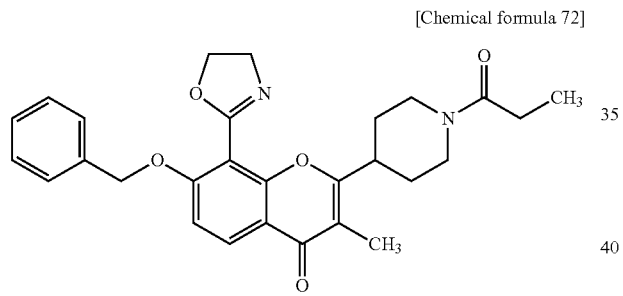

To a solution of 7-(benzyloxy)-N-(2-hydroxyethyl)-3-methyl-4-oxo-2-(1-propanoylpiperidin-4-yl)-4H-chromene-8-carboxamide (140 mg, 0.28 mmol) obtained in Example 35-2 in dichloromethane (4 mL), thionyl chloride (62 µL, 0.85 mmol) was added dropwise, and then the mixture was stirred at room temperature for 10 hours. The reaction solution was concentrated under reduced pressure, and then the residue was subjected to azeotropy with toluene (6 mL). 1,2-Dichloroethane (4 mL) and 1,8-diazabicyclo[5.4.0]undec-7-ene (950 µL, 5.68 mmol) were added to the obtained residue, and then the mixture was heated to reflux for 4 days. A 0.2 N aqueous hydrochloric acid solution (50 mL) was added to the reaction solution, followed by extraction with dichloromethane. The organic layer was dried over sodium sulfate. The desiccant was filtered off, and then the filtrate was concentrated under reduced pressure. The obtained residue was purified by NH silica gel column chromatography (n-hexane/ethyl acetate=90/10→60/40) to obtain 37 mg of the title compound (yield: 27%) as an oil.

$^1$H-NMR (CDCl$_3$) δ: 8.18 (1H, d, J=9.2 Hz), 7.42-7.30 (5H, m), 7.01 (1H, d, J=9.2 Hz), 5.27 (2H, s), 4.78-4.72 (1H, m), 4.49-4.38 (2H, m), 4.17-4.05 (2H, m), 4.01-3.96 (1H, m), 3.21-3.06 (2H, m), 2.74-2.66 (1H, m), 2.41 (2H, q, J=7.4 Hz), 2.07 (3H, s), 1.91-1.65 (4H, m), 1.20 (3H, t, J=7.4 Hz).

MS; m/z: 475 (M+H)$^+$

Example 35-4

8-(4,5-Dihydro-1,3-oxazol-2-yl)-7-hydroxy-3-methyl-2-(1-propanoylpiperidin-4-yl)-4H-chromen-4-one

[Chemical formula 73]

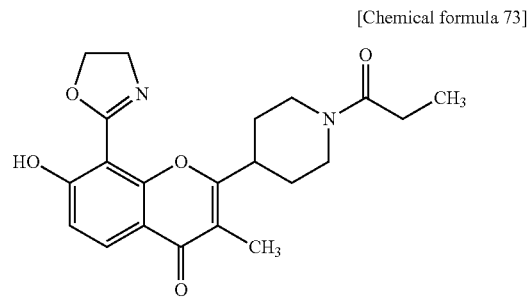 [SMILES: CCC(=O)N1CCC(c2oc3c(C4=NCCO4)c(O)ccc3c(=O)c2C)CC1]

The title compound (49 mg, yield: 53%) was obtained through the same reaction as in Example 1-3 using 7-(benzyloxy)-8-(4,5-dihydro-1,3-oxazol-2-yl)-3-methyl-2-(1-propanoylpiperidin-4-yl)-4H-chromen-4-one obtained in Example 35-3.

$^1$H-NMR (DMSO-d$_6$) δ: 7.98 (1H, d, J=8.7 Hz), 6.96 (1H, d, J=8.7 Hz), 4.56-4.50 (3H, m), 4.07-3.96 (3H, m), 3.30-3.13 (2H, m), 2.70-2.62 (1H, m), 2.39 (2H, q, J=7.4 Hz), 2.00 (3H, s), 1.92-1.71 (4H, m), 1.06 (3H, t, J=7.4 Hz).

MS; m/z: 385 (M+H)$^+$

Example 36

7-Hydroxy-3-methyl-2-(1-propanoylpiperidin-4-yl)-8-(2,2,2-trifluoroethyl)-4H-chromen-4-one Example 36-1

Benzyl 4-[7-(benzyloxy)-8-formyl-3-methyl-4-oxo-4H-chromen-2-yl]piperidine-1-carboxylate

[Chemical formula 74]

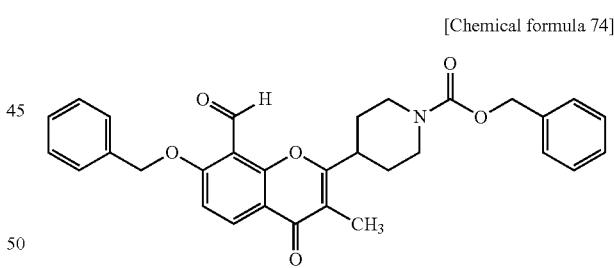

Benzyl 4-(8-formyl-7-hydroxy-3-methyl-4-oxo-4H-chromen-2-yl)piperidine-1-carboxylate (2.01 g, 27%) was obtained through the same reaction as in Example 34-1 using benzyl 4-(7-hydroxy-3-methyl-4-oxo-4H-chromen-2-yl)piperidine-1-carboxylate (7.06 g, 17.94 mmol) obtained in Example 31-1, hexamethylenetetramine (17.6 g, 125.6 mmol), and acetic acid (180 mL). Subsequently, the title compound (966 mg, yield: 100%) was obtained through the same reaction as in 34-2 using the obtained compound (800 mg, 1.90 mmol) and benzyl bromide (677 µL, 5.69 mmol).

$^1$H-NMR (CDCl$_3$) δ: 10.67 (1H, s), 8.37 (1H, d, J=8.9 Hz), 7.47-7.30 (10H, m), 7.11 (1H, d, J=8.9 Hz), 5.32 (2H, s), 5.18 (2H, s), 4.48-4.35 (2H, m), 3.05-2.96 (1H, m), 2.94-2.85 (2H, m), 2.17-2.07 (2H, m), 2.09 (3H, s), 1.84-1.78 (2H, m).

MS; m/z: 512 (M+H)$^+$

Example 36-2

Benzyl 4-[7-(benzyloxy)-3-methyl-4-oxo-8-(2,2,2-trifluoro-1-hydroxyethyl)-4H-chromen-2-yl]piperidine-1-carboxylate

[Chemical formula 75]

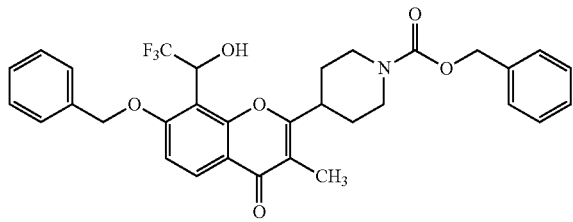

To a solution of benzyl 4-[7-(benzyloxy)-8-formyl-3-methyl-4-oxo-4H-chromen-2-yl]piperidine-1-carboxylate (378 mg, 0.74 mmol) obtained in Example 36-1 in dimethyl sulfoxide (10 mL), molecular sieves 4A (1.0 g) and trimethyl (trifluoromethyl)silane (1.09 mL, 7.39 mmol) were added, and then the mixture was stirred at room temperature for 3 hours. Ethyl acetate (80 mL) was added to the reaction solution, and insoluble matter was removed by filtration through celite. The filtrate was washed with water and then dried over sodium sulfate. The desiccant was filtered off, and then the filtrate was concentrated under reduced pressure. A 1 N aqueous hydrochloric acid solution (3 mL) and methanol (12 mL) were added to the obtained residue, and the mixture was stirred at room temperature for 2 hours. The reaction solution was concentrated under reduced pressure, and ethyl acetate was added to the obtained residue. The organic layer was washed with water and then dried over sodium sulfate. The desiccant was filtered off, and then the filtrate was concentrated under reduced pressure. The obtained residue was purified by silica gel column chromatography (n-hexane/ethyl acetate=80/20→40/60) to obtain 392 mg of the title compound (yield: 91%).

$^1$H-NMR (CDCl$_3$) δ: 8.24 (1H, d, J=9.2 Hz), 7.47-7.30 (10H, m), 7.12 (1H, d, J=9.2 Hz), 5.70-5.60 (1H, m), 5.27 (2H, s), 5.18 (2H, s), 4.81-4.70 (1H, br m), 4.49-4.32 (2H, m), 3.07-2.98 (1H, m), 2.96-2.83 (2H, m), 2.09 (3H, s), 1.90-1.78 (4H, m).

MS; m/z: 582 (M+H)$^+$

Example 36-3

Benzyl 4-[7-(benzyloxy)-3-methyl-4-oxo-8-{2,2,2-trifluoro-1-[(1H-imidazol-1-ylcarbonothioyl)oxy]ethyl}-4H-chromen-2-yl]piperidine-1-carboxylate

[Chemical formula 76]

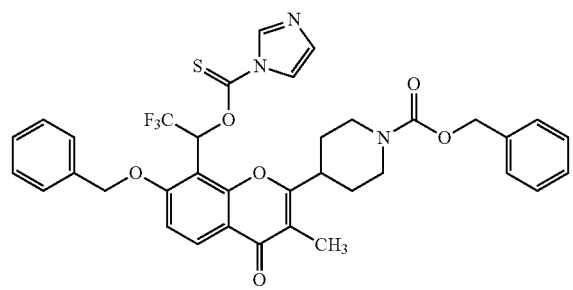

A solution of benzyl 4-[7-(benzyloxy)-3-methyl-4-oxo-8-(2,2,2-trifluoro-1-hydroxyethyl)-4H-chromen-2-yl]piperidine-1-carboxylate (128 mg, 0.22 mmol) obtained in Example 36-2, 1,1'-thiocarbonylimidazole (137 mg, 0.77 mmol), and N,N-dimethyl-4-aminopyridine (3 mg, 0.02 mmol) in tetrahydrofuran (3 mL) was heated to reflux for 24 hours. Water was added to the reaction solution, followed by extraction with ethyl acetate. Then, the organic layer was dried over sodium sulfate. The desiccant was filtered off, and then the filtrate was concentrated under reduced pressure. The obtained residue was purified by silica gel column chromatography (n-hexane/ethyl acetate=60/40→40/60) to obtain 137 mg of the title compound (yield: 90%).

MS; m/z: 692 (M+H)$^+$

Example 36-4

Benzyl 4-[7-(benzyloxy)-3-methyl-4-oxo-8-(2,2,2-trifluoroethyl)-4H-chromen-2-yl]piperidine-1-carboxylate

[Chemical formula 77]

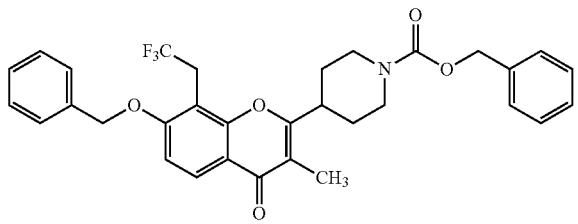

Tri-n-butyltin hydride (104 μL, 0.39 mmol) and a catalytic amount of azobisisobutyronitrile were added to a solution of benzyl 4-[7-(benzyloxy)-3-methyl-4-oxo-8-{2,2,2-trifluoro-1-[(1H-imidazol-1-ylcarbonothioyl)oxy]ethyl}-4H-chromen-2-yl]piperidine-1-carboxylate (135 mg, 0.20 mmol) obtained in Example 36-3 in tetrahydrofuran (1.5 mL), and the mixture was heated to reflux for 1 hour. The reaction solution was concentrated under reduced pressure. The obtained residue was purified by silica gel column chromatography (n-hexane/ethyl acetate=80/20→40/60) to obtain 105 mg of the title compound (yield: 95%).

$^1$H-NMR (CDCl$_3$) δ: 8.17 (1H, d, J=8.7 Hz), 7.43-7.30 (10H, m), 7.05 (1H, d, J=8.7 Hz), 5.23 (2H, s), 5.18 (2H, s), 4.48-4.33 (2H, m), 3.73 (2H, q, J=10.5 Hz), 3.08-2.99 (1H, m), 2.97-2.85 (2H, m), 2.09 (3H, s), 1.94-1.81 (4H, m).

MS; m/z: 566 (M+H)$^+$

Example 36-5

7-Hydroxy-3-methyl-2-(1-propanoylpiperidin-4-yl)-8-(2,2,2-trifluoroethyl)-4H-chromen-4-one

[Chemical formula 78]

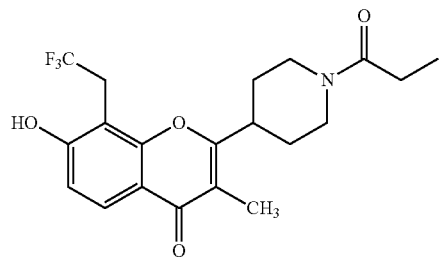

The title compound (46 mg, yield: 62%) was obtained through the use of the same reaction as in Example 31-2 using benzyl 4-[7-(benzyloxy)-3-methyl-4-oxo-8-(2,2,2-trifluoroethyl)-4H-chromen-2-yl]piperidine-1-carboxylate (105 mg, 0.21 mmol) obtained in Example 36-4 and propionic acid anhydride (72 μL, 0.56 mmol).

$^1$H-NMR (DMSO-d$_6$) δ: 11.09 (1H, s), 7.88 (1H, d, J=8.7 Hz), 7.00 (1H, d, J=8.7 Hz), 4.58-4.52 (1H, m), 4.01-3.96 (1H, m), 3.71 (2H, q, J=11.2 Hz), 3.28-3.11 (2H, m), 2.69-2.61 (1H, m), 2.44-2.28 (2H, m), 1.99 (3H, s), 1.87-1.57 (4H, m), 1.02 (3H, t, J=7.3 Hz).

MS; m/z: 398 (M+H)$^+$

Example 37

2-(4-Acetylpiperazin-1-yl)-7-hydroxy-3,8-dimethyl-4H-chromen-4-one hydrochloride

Example 37-1

4-Hydroxy-7-(methoxymethoxy)-3,8-dimethyl-2H-chromene-2-thione

[Chemical formula 79]

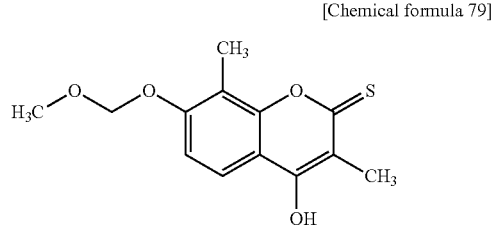 [SMILES: COCOc1ccc2c(O)c(C)c(=S)oc2c1C]

According to the method described in Eur. J. Med. Chem. 36 (2001) 697, a solution of 1-[2-hydroxy-4-(methoxymethoxy)-3-methylphenyl]propan-1-one (3.99 g, 17.8 mmol) obtained in Example 2-1 and carbon disulfide (1.07 mL, 17.8 mmol) in tetrahydrofuran (30 mL) was added to a solution of potassium t-butoxide (5.99 g, 53.4 mmol) in tetrahydrofuran (20 mL), and the mixture was stirred overnight at room temperature. Water (50 mL) was added to the reaction solution, and then the pH of the mixture was adjusted to 5 with 2 M hydrochloric acid, followed by extraction with ethyl acetate. The pH of the aqueous layer was adjusted to 5 again with 2 M hydrochloric acid, followed by extraction with ethyl acetate. The organic layer was washed with saturated brine and then dried over magnesium sulfate. The solvent was concentrated under reduced pressure to obtain 3.80 g of the title compound (yield: 80%).

$^1$H-NMR (DMSO-d$_6$) δ: 7.86 (1H, d, J=9.2 Hz), 7.23 (1H, d, J=9.2 Hz), 5.37 (2H, s), 3.42 (3H, s), 2.31 (3H, s), 2.25 (3H, s).

MS; m/z: 267 (M+H)$^+$.

Example 37-2

7-(Methoxymethoxy)-3,8-dimethyl-2-(methylsulfanyl)-4H-chromen-4-one

[Chemical formula 80]

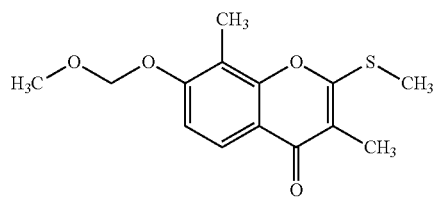

Potassium carbonate (995 mg, 7.20 mmol) and methyl iodide (1.50 mL, 24.0 mmol) were added to a solution of 4-hydroxy-7-(methoxymethoxy)-3,8-dimethyl-2H-chromene-2-thione (1.60 g, 6.00 mmol) obtained in Example 37-1 in acetone (16 mL), and the mixture was refluxed for 45 minutes. After cooling to room temperature, water (15 mL) was added to the reaction solution, followed by extraction with ethyl acetate. The obtained residue was purified by silica gel column chromatography (n-hexane/ethyl acetate=95/5→60/40) to obtain 1.34 g of the title compound (yield: 80%).

$^1$H-NMR (DMSO-D$_6$) δ: 7.83 (1H, d, J=9.2 Hz), 7.22 (1H, d, J=9.2 Hz), 5.37 (2H, s), 3.42 (3H, s), 2.71 (3H, s), 2.31 (3H, s), 1.91 (3H, s).

MS; m/z: 281 (M+H)$^+$.

Example 37-3

7-(Methoxymethoxy)-3,8-dimethyl-2-(methylsulfonyl)-4H-chromen-4-one

[Chemical formula 81]

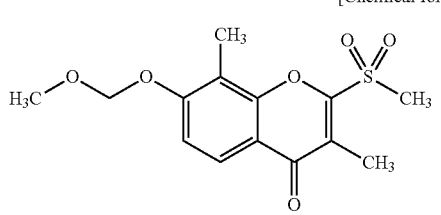

To a solution of 7-(methoxymethoxy)-3,8-dimethyl-2-(methylsulfanyl)-4H-chromen-4-one (1.18 g, 4.21 mmol) obtained in Example 37-2 in dichloromethane (18 mL), m-chloroperbenzoic acid was added under cooling with ice, and the mixture was stirred for 20 minutes and then stirred overnight at room temperature. The reaction solution was concentrated. Then, a diethyl ether/n-hexane (=1/1, 60 mL) solvent was added to the residue, and the mixture was stirred for 1.5 hours under cooling with ice. The crystals were collected by filtration and washed with diethyl ether/n-hexane (=1/1) cooled with ice to obtain 1.31 g of the title compound (yield: 100%).

$^1$H-NMR (DMSO-d$_6$) δ: 7.92 (1H, d, J=9.2 Hz), 7.34 (1H, d, J=9.2 Hz), 5.41 (2H, s), 3.54 (3H, s), 3.42 (3H, s), 2.33 (3H, s), 2.27 (3H, s).

MS; m/z: 313 (M+H)$^+$.

Example 37-4

2-(4-Acetylpiperazin-1-yl)-7-(methoxymethoxy)-3,8-dimethyl-4H-chromen-4-one

[Chemical formula 82]

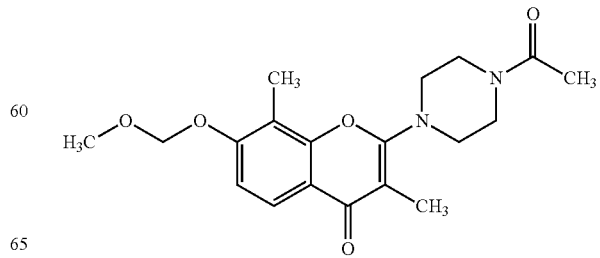

1-Acetylpiperazine (220 mg, 1.70 mmol) and triethylamine (1 mL) were added to a solution of 7-(methoxymethoxy)-3,8-dimethyl-2-(methylsulfonyl)-4H-chromen-4-one (171 mg, 0.55 mmol) obtained in Example 37-3 in dimethyl sulfoxide (5 mL), and the mixture was stirred for 5 hours under cooling with ice. Ethyl acetate was added to the reaction solution. The organic layer was washed with water and then dried over anhydrous sodium sulfate, and then the solvent was distilled off under reduced pressure. The obtained residue was purified by silica gel column chromatography (chloroform/methanol=97/3→93/7) to obtain 60 mg of the title compound (yield: 30%), which was used directly in the next reaction.

MS; m/z: 361 (M+H)$^+$.

Example 37-5

2-(4-Acetylpiperazin-1-yl)-7-hydroxy-3,8-dimethyl-4H-chromen-4-one hydrochloride

[Chemical formula 83]

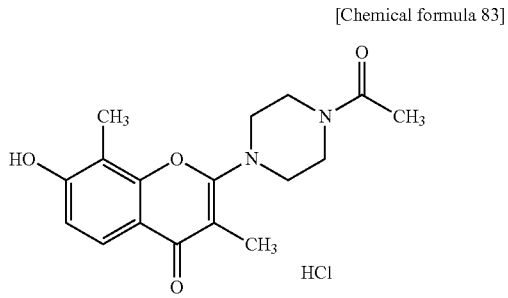 [SMILES: CC(=O)N1CCN(c2oc3c(C)c(O)ccc3c(=O)c2C)CC1 ; Cl]

A 4 N solution of hydrochloric acid in dioxane (1 mL) was added to a solution of 2-(4-acetylpiperazin-1-yl)-7-(methoxymethoxy)-3,8-dimethyl-4H-chromen-4-one (60 mg, 0.17 mmol) obtained in Example 37-4 in dioxane (3 mL), and the mixture was stirred at room temperature for 15 minutes. The deposited crystals were washed with dioxane and isopropyl ether and then collected by filtration to obtain 36 mg of the title compound (yield: 63%).

$^1$H-NMR (DMSO-d$_6$) δ: 10.41 (1H, br s), 7.63 (1H, d, J=8.8 Hz), 6.89 (1H, d, J=8.8 Hz), 5.37 (1H, br s), 3.60-3.56 (4H, m), 3.41-3.37 (2H, br m), 3.34-3.30 (2H, br m), 2.18 (3H, s), 2.03 (3H, s), 1.87 (3H, s).

MS; m/z: 317 (M+H)$^+$.

Example 38

7-Hydroxy-3,8-dimethyl-2-(4-methylpiperazin-1-yl)-4H-chromen-4-one dihydrochloride

[Chemical formula 84]

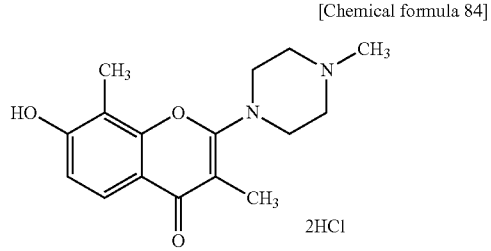 [SMILES: Cc1c(N2CCN(C)CC2)oc2c(C)c(O)ccc2c1=O ; "2HCl"]

The title compound (60 mg, yield: 17%) was obtained by sequentially performing the same reactions as in Examples 37-4 and 37-5 using 7-(methoxymethoxy)-3,8-dimethyl-2-(methylsulfonyl)-4H-chromen-4-one (382 mg, 1.22 mmol) obtained in Example 37-3 and methylpiperazine (367 mg, 3.66 mmol).

$^1$H-NMR (DMSO-d$_6$) δ: 11.07 (1H, br s), 10.45 (1H, br s), 7.64 (1H, d, J=8.8 Hz), 6.91 (1H, d, J=8.8 Hz), 4.92 (1H, br s), 3.85-3.78 (2H, m), 3.52-3.42 (4H, m), 3.25-3.13 (2H, m), 2.80-2.78 (3H, br m), 2.19 (3H, s), 1.86 (3H, s).

MS; m/z: 289 (M+H)$^+$.

Example 39

7-Hydroxy-2-(3-hydroxypiperidin-1-yl)-3,8-dimethyl-4H-chromen-4-one hydrochloride

[Chemical formula 85]

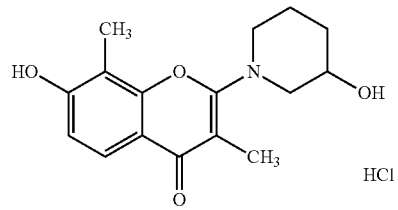

The title compound (137 mg, yield: 66%) was obtained by sequentially performing the same reactions as in Examples 37-4 and 37-5 using 7-(methoxymethoxy)-3,8-dimethyl-2-(methylsulfonyl)-4H-chromen-4-one (200 mg, 0.64 mmol) obtained in Example 37-3 and 3-hydroxypiperidine (194 mg, 1.92 mmol).

$^1$H-NMR (DMSO-d$_6$) δ: 10.43 (1H, br s), 7.69 (1H, br s), 7.66 (1H, d, J=8.5 Hz), 6.91 (1H, d, J=8.5 Hz), 3.68-3.61 (2H, m), 3.54-3.46 (1H, m), 3.20-3.12 (1H, m), 3.01-2.94 (1H, m), 2.48 (1H, br s), 2.19 (3H, s), 1.94-1.78 (2H, m), 1.89 (3H, s), 1.61-1.50 (1H, m), 1.46-1.36 (1H, m).

MS; m/z: 290 (M+H)$^+$.

Example 40

8-Methyl-7-hydroxy-2-[1-(methoxyacetyl)piperidin-4-yl)]-3-methyl-4H-chromen-4-one

Example 40-1

Benzyl 4-(7-hydroxy-8-iodo-3-methyl-4-oxo-4H-chromen-2-yl)piperidine-1-carboxylate

[Chemical formula 86]

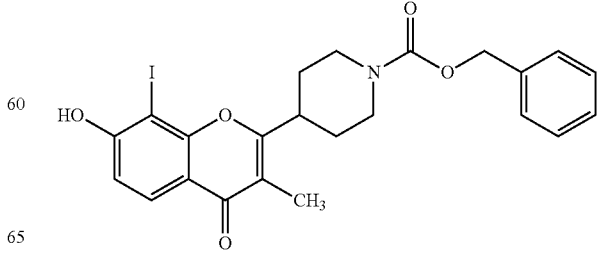

The title compound (31.0 g, yield: 85%) was obtained through the same reaction as in Example 32 using benzyl 4-(7-hydroxy-3-methyl-4-oxo-4H-chromen-2-yl)piperidine-1-carboxylate (27.5 g, 69.9 mmol) obtained in Example 31-1 and N-iodosuccinimide (15.4 g, 68.8 mmol).

¹H-NMR (CDCl₃) δ: 8.10 (1H, d, J=9.0 Hz), 7.46-7.35 (5H, m), 7.06 (1H, d, J=9.0 Hz), 6.44 (1H, s), 5.22 (2H, s), 4.54-4.35 (2H, m), 3.09-2.87 (3H, m), 2.15-2.01 (2H, m), 2.11 (3H, s), 1.93-1.83 (2H, m).

Example 40-2

Benzyl 4-[7-(methoxymethoxy)-3-methyl-4-oxo-8-vinyl-4H-chromen-2-yl]piperidine-1-carboxylate

[Chemical formula 87]

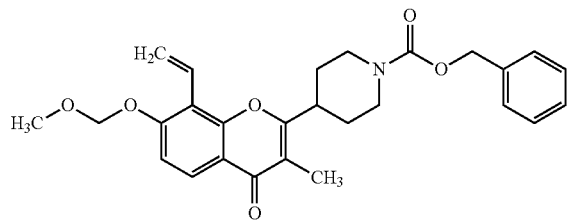

Benzyl 4-[8-iodo-7-(methoxymethoxy)-3-methyl-4-oxo-4H-chromen-2-yl]piperidine-1-carboxylate (10.2 g, yield: 94%) was obtained through the same reaction as in Example 2-1 using benzyl 4-(7-hydroxy-8-iodo-3-methyl-4-oxo-4H-chromen-2-yl)piperidine-1-carboxylate (10.0 g, 19.3 mmol) obtained in Example 40-1 and chloro(methoxy)methane (2.20 mL, 29.0 mmol). Subsequently, the title compound (413 mg, yield: quantitative) was obtained through the same cross-coupling reaction as in Example 33-1 using the obtained compound (500 mg, 0.89 mmol) and 4,4,5,5-tetramethyl-2-vinyl-1,3,2-dioxaborolane (300 μL, 1.75 mmol).

¹H-NMR (CDCl₃) δ: 8.04 (1H, d, J=9.0 Hz), 7.39-7.28 (5H, m), 7.15 (1H, d, J=9.0 Hz), 6.93 (1H, dd, J=18.0, 12.0 Hz), 6.07 (1H, dd, J=18.0, 2.3 Hz), 5.62 (1H, dd, J=12.0, 2.3 Hz), 5.29 (2H, s), 5.15 (2H, s), 4.46-4.27 (2H, m), 3.47 (3H, s), 3.07-2.96 (1H, m), 2.94-2.81 (2H, m), 2.06 (3H, s), 1.97-1.75 (4H, m).

Example 40-3

8-Ethyl-2-[1-(methoxyacetyl)piperidin-4-yl]-7-(methoxymethoxy)-3-methyl-4H-chromen-4-one

[Chemical formula 88]

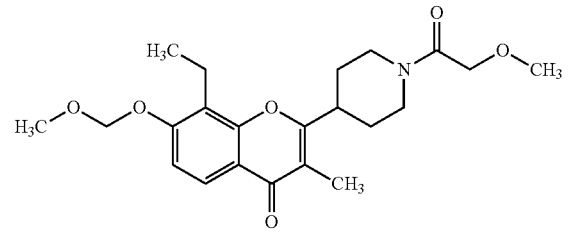

8-Ethyl-7-(methoxymethoxy)-3-methyl-2-(piperidin-4-yl)-4H-chromen-4-one was obtained through the same reaction as in Example 1-3 using benzyl 4-[7-(methoxymethoxy)-3-methyl-4-oxo-8-vinyl-4H-chromen-2-yl]piperidine-1-carboxylate (413 mg, 0.89 mmol) obtained in Example 40-2. Subsequently, the title compound (228 mg, yield: 49%) was obtained through the same reaction as in Example 7-3 using the obtained compound and methoxyacetyl chloride (160 μL, 1.80 mmol).

¹H-NMR (CDCl₃) δ: 8.05 (1H, d, J=8.8 Hz), 7.17 (1H, d, J=8.8 Hz), 5.33 (2H, s), 4.89-4.82 (1H, m), 4.28 (1H, d, J=13.2 Hz), 4.18-4.09 (1H, m), 4.15 (1H, d, J=13.2 Hz), 3.53 (3H, s), 3.51 (3H, s), 3.24-3.13 (2H, m), 2.89 (2H, q, J=7.4 Hz), 2.80-2.70 (1H, m), 2.13 (3H, s), 2.00-1.92 (4H, m), 1.20 (3H, t, J=7.4 Hz).

Example 40-4

8-Ethyl-7-hydroxy-2-[1-(methoxyacetyl)piperidin-4-yl]-3-methyl-4H-chromen-4-one

[Chemical formula 89]

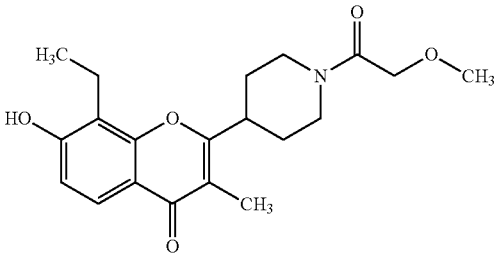

The title compound (155 mg, yield: 79%) was obtained through the same reaction as in Example 37-5 using 8-ethyl-2-[1-(methoxyacetyl)piperidin-4-yl]-7-(methoxymethoxy)-3-methyl-4H-chromen-4-one (220 mg, 0.54 mmol) obtained in Example 40-3.

¹H-NMR (CDCl₃) δ: 8.02 (1H, s), 7.94 (1H, d, J=8.6 Hz), 7.00 (1H, d, J=8.6 Hz), 4.89-4.80 (1H, m), 4.28 (1H, d, J=13.5 Hz), 4.16-4.08 (1H, m), 4.15 (1H, d, J=13.5 Hz), 3.50 (3H, s), 3.24-3.12 (2H, m), 2.88 (2H, q, J=7.4 Hz), 2.81-2.70 (1H, m), 2.14 (3H, s), 2.00-1.90 (4H, m), 1.21 (3H, t, J=7.4 Hz).

MS m/z 360 (M+H)⁺.

Example 41

3-Ethyl-7-hydroxy-2-[1-(methoxyacetyl)piperidin-4-yl]-8-methyl-4H-chromen-4-one

Example 41-1

1-[2-Hydroxy-4-(methoxymethoxy)-3-methylphenyl]butan-1-one

[Chemical formula 90]

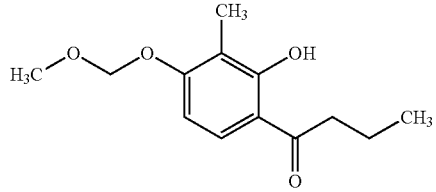

The title compound (10.7 g, yield: 94%) was obtained through the same reaction as in Example 2-1 using 1-(2,4- dihydroxy-3-methylphenyl)butan-1-one (9.30 g, 47.9 mmol) and chloro(methoxy)methane (4.60 mL, 60.0 mmol).

¹H-NMR (CDCl₃) δ: 12.92 (1H, s), 7.57 (1H, d, J=9.0 Hz), 6.61 (1H, d, J=9.0 Hz), 5.23 (2H, s), 3.45 (3H, s), 2.86 (2H, t, J=7.4 Hz), 2.10 (3H, s), 1.78-1.67 (2H, m), 0.97 (3H, t, J=7.4 Hz).

Example 41-2

Benzyl 4-[3-ethyl-7-hydroxy-8-methyl-4-oxo-4H-chromen-2-yl]piperidine-1-carboxylate

[Chemical formula 91]

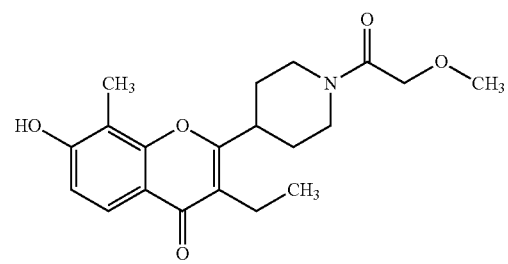

1-Benzyl 4-[6-butanoyl-3-(methoxymethoxy)-2-methylphenyl]piperidine-1,4-dicarboxylate (19.8 g, yield: 91%) was obtained through the same reaction as in Example 1-1 using 1-[2-hydroxy-4-(methoxymethoxy)-3-methylphenyl]butan-1-one (10.7 g, 44.9 mmol) obtained in Example 41-1 and 1-[(benzyloxy)carbonyl]piperidine-4-carboxylic acid (14.0 g, 53.2 mmol). Subsequently, the title compound (12.2 g, yield: 71%) was obtained through the same reaction as in Example 1-2 using the obtained compound (19.8 g, 41.0 mmol).

¹H-NMR (CDCl₃) δ: 7.90 (1H, d, J=8.6 Hz), 7.40-7.28 (5H, m), 6.84 (1H, d, J=8.6 Hz), 5.16 (2H, s), 4.47-4.29 (2H, m), 3.04-2.83 (3H, m), 2.56 (2H, q, J=7.4 Hz), 2.27 (3H, s), 2.01-1.88 (2H, m), 1.85-1.75 (2H, m), 1.10 (3H, t, J=7.4 Hz).

Example 41-3

3-Ethyl-7-(methoxymethoxy)-8-methyl-2-(piperidin-4-yl)-4H-chromen-4-one

[Chemical formula 92]

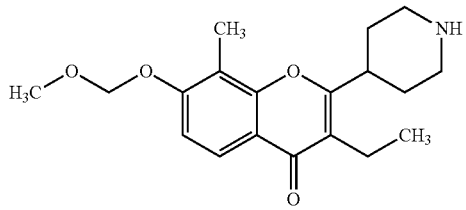

Benzyl 4-[3-ethyl-7-(methoxymethoxy)-8-methyl-4-oxo-4H-chromen-2-yl]piperidine-1-carboxylate (12.1 g, yield: 90%) was obtained through the same reaction as in Example 2-1 using benzyl 4-[3-ethyl-7-hydroxy-8-methyl-4-oxo-4H-chromen-2-yl]piperidine-1-carboxylate (12.2 g, 29.0 mmol) obtained in Example 41-1 and chloro(methoxy)methane (3.30 mL, 43.5 mmol). Subsequently, 3-ethyl-7-(methoxymethoxy)-8-methyl-2-piperidin-4-yl-4H-chromen-4-one (8.61 g, yield: quantitative) was obtained through the same reaction as in Example 1-3 using the obtained compound (12.1 g, 26.0 mmol).

¹H-NMR (CDCl₃) δ: 7.98 (1H, d, J=9.0 Hz), 7.10 (1H, d, J=9.0 Hz), 5.27 (2H, s), 3.47 (3H, s), 3.27-3.19 (2H, m), 3.00-2.90 (1H, m), 2.80-2.71 (2H, m), 2.56 (2H, q, J=7.4 Hz), 2.33 (3H, s), 2.03-1.91 (2H, m), 1.82-1.73 (2H, m), 1.09 (3H, t, J=7.4 Hz).

Example 41-4

3-Ethyl-7-hydroxy-2-[1-(methoxyacetyl)piperidin-4-yl]-8-methyl-4H-chromen-4-one

[Chemical formula 93]

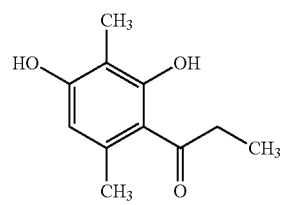

3-Ethyl-2-[1-(methoxyacetyl)piperidin-4-yl]-7-(methoxymethoxy)-8-methyl-4H-chromen-4-one (2.45 g, yield: quantitative) was obtained through the same reaction as in Example 7-3 using 3-ethyl-7-(methoxymethoxy)-8-methyl-2-piperidin-4-yl-4H-chromen-4-one (2.00 g, 6.04 mmol) obtained in Example 41-2 and methoxyacetyl chloride (820 μL, 9.07 mmol). Subsequently, the title compound (1.54 g, yield: 71%) was obtained through the same reaction as in Example 37-5 using the obtained compound (2.45 g, 6.04 mmol).

¹H-NMR (CDCl₃) δ: 7.90 (1H, d, J=8.6 Hz), 7.03 (1H, s), 6.88 (1H, d, J=8.6 Hz), 4.84-4.74 (1H, m), 4.22 (1H, d, J=13.7 Hz), 4.11-4.00 (1H, m), 4.11 (1H, d, J=13.7 Hz), 3.45 (3H, s), 3.20-3.04 (2H, m), 2.76-2.66 (1H, m), 2.58 (2H, q, J=7.4 Hz), 2.27 (3H, s), 2.03-1.83 (4H, m), 1.11 (3H, t, J=7.4 Hz).

MS; m/z: 360 (M+H)⁺.

Example 42

7-Hydroxy-2-[1-(methoxyacetyl)piperidin-4-yl]-3,5,8-trimethyl-4H-chromen-4-one

Example 42-1

1-(2,4-Dihydroxy-3,6-dimethylphenyl)propan-1-one

[Chemical formula 94]

A boron trifluoride-diethyl ether complex (10.0 mL, 78.9 mmol) was added to 2,5-dimethylresorcin (4.50 g, 32.6 mmol), and the mixture was stirred at 70° C. for 2 hours and then at 80° C. for 2 hours. Propionic acid anhydride (4.60 mL, 34.7 mmol) was added thereto under cooling with ice, and the mixture was stirred at 70° C. for 2 hours. Water and ethyl acetate were added thereto under cooling with ice, and the mixture was stirred at room temperature for 1 hour and then separated into aqueous and organic layers. The ethyl acetate layer was washed with water and saturated brine in this order and dried over sodium sulfate, and then the solvent was distilled off under reduced pressure to obtain 6.40 g of the title compound (yield: quantitative).

$^1$H-NMR (CDCl$_3$) δ: 13.63 (1H, s), 6.17 (1H, s), 5.13 (1H, s), 2.90 (2H, q, J=7.2 Hz), 2.51 (3H, s), 2.06 (3H, s), 1.18 (3H, t, J=7.2 Hz).

Example 42-2

1-[2-Hydroxy-4-(methoxymethoxy)-3,6-dimethylphenyl]propan-1-one

[Chemical formula 95]

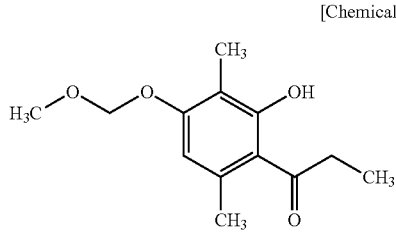

The title compound (6.30 g, yield: 81%) was obtained through the same reaction as in Example 2-1 using 1-(2,4-dihydroxy-3,6-dimethylphenyl)propan-1-one (6.40 g, 32.6 mmol) and chloro(methoxy)methane (3.00 mL, 39.5 mmol).

$^1$H-NMR (CDCl$_3$) δ: 13.24 (1H, s), 6.45 (1H, s), 5.22 (2H, s), 3.47 (3H, s), 2.91 (2H, q, J=7.2 Hz), 2.56 (3H, s), 2.08 (3H, s), 1.19 (3H, t, J=7.2 Hz).

Example 42-3

Benzyl 4-(7-hydroxy-3,5,8-trimethyl-4-oxo-4H-chromen-2-yl)piperidine-1-carboxylate

[Chemical formula 96]

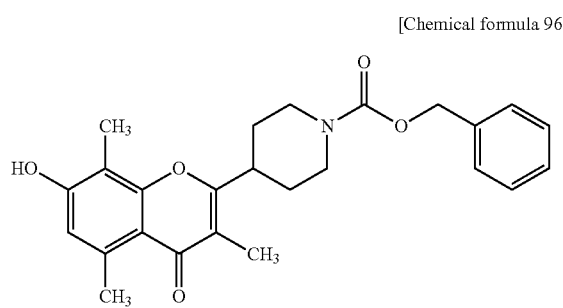

1-Benzyl 4-[3-(methoxymethoxy)-2,5-dimethyl-6-propanoylphenyl]piperidine-1,4-dicarboxylate (11.8 g, yield: 92%) was obtained through the same reaction as in Example 1-1 using 1-[2-hydroxy-4-(methoxymethoxy)-3,6-dimethylphenyl]propan-1-one (6.30 g, 26.4 mmol) obtained in Example 42-2 and 1-[(benzyloxy)carbonyl]piperidine-4-carboxylic acid (7.70 g, 29.2 mmol). Subsequently, the title compound (8.40 g, yield: 82%) was obtained through the same reaction as in Example 1-2 using the obtained compound (11.8 g, 24.4 mmol).

$^1$H-NMR (CDCl$_3$) δ: 7.38-7.27 (5H, m), 6.59 (1H, s), 5.15 (2H, s), 4.44-4.26 (2H, m), 3.02-2.78 (3H, m), 2.74 (3H, s), 2.21 (3H, s), 2.00 (3H, s), 1.95-1.75 (4H, m).

Example 42-4

7-(Methoxymethoxy)-3,5,8-trimethyl-2-(piperidin-4-yl)-4H-chromen-4-one

[Chemical formula 97]

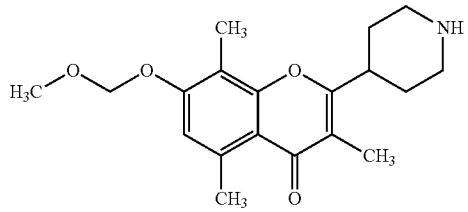

Benzyl 4-[7-(methoxymethoxy)-3,5,8-trimethyl-4-oxo-4H-chromen-2-yl]piperidine-1-carboxylate (9.1 g, yield: 98%) was obtained through the same reaction as in Example 2-1 using benzyl 4-(7-hydroxy-3,5,8-trimethyl-4-oxo-4H-chromen-2-yl)piperidine-1-carboxylate (8.40 g, 19.9 mmol) obtained in Example 42-3 and chloro(methoxy)methane (2.30 mL, 30.3 mmol). Subsequently, the title compound (6.40 g, yield: 98%) was obtained through the same reaction as in Example 1-3 using the obtained compound (8.40 g, 19.9 mmol).

$^1$H-NMR (CDCl$_3$) δ: 6.86 (1H, s), 5.28 (2H, s), 3.50 (3H, s), 3.37-3.30 (2H, m), 3.03-2.94 (1H, m), 2.87-2.78 (2H, m), 2.82 (3H, s), 2.32 (3H, s), 2.11-2.02 (2H, m), 2.03 (3H, s), 1.90-1.82 (2H, m).

Example 42-5

7-Hydroxy-2-[1-(methoxyacetyl)piperidin-4-yl]-3,5,8-trimethyl-4H-chromen-4-one

[Chemical formula 98]

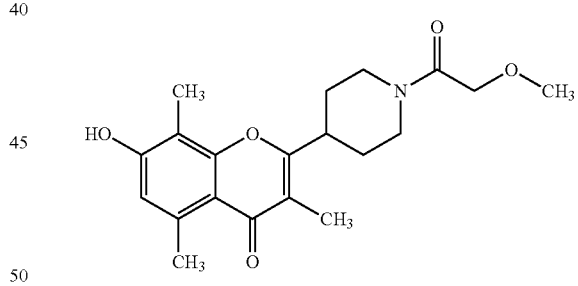

2-[1-(Methoxyacetyl)piperidin-4-yl]-7-(methoxymethoxy)-3,5,8-trimethyl-4H-chromen-4-one (2.30 g, yield: 94%) was obtained through the same reaction as in Example 7-3 using 7-(methoxymethoxy)-3,5,8-trimethyl-2-(piperidin-4-yl)-4H-chromen-4-one (2.00 g, 6.04 mmol) obtained in Example 42-4 and methoxyacetyl chloride (820 μL, 9.07 mmol). Subsequently, the title compound (1.20 g, yield: 59%) was obtained through the same reaction as in Example 37-5 using the obtained compound (2.30 g, 5.70 mmol).

$^1$H-NMR (CDCl$_3$) δ: 6.62 (1H, s), 5.62 (1H, s), 4.88-4.80 (1H, m), 4.26 (3H, d, J=13.2 Hz), 4.16 (1H, d, J=13.2 Hz), 4.13-4.06 (1H, m), 3.50 (3H, s), 3.23-3.08 (2H, m), 2.80 (3H, s), 2.78-2.69 (1H, m), 2.27 (3H, s), 2.08 (3H, s), 2.01-1.90 (4H, m).

MS; m/z: 360 (M+H)$^+$.

Example 43

2-[1-(Ethoxyacetyl)piperidin-4-yl]-7-hydroxy-3,8-dimethyl-4H-chromen-4-one

Example 43-1

Benzyl 4-(7-hydroxy-3,8-dimethyl-4-oxo-4H-chromen-2-yl)piperidine-1-carboxylate

[Chemical formula 99]

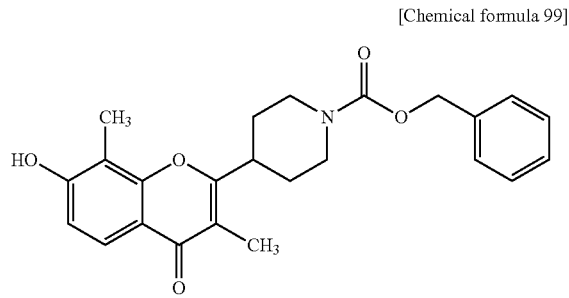 [SMILES: Cc1c(C2CCN(C(=O)OCc3ccccc3)CC2)oc2c(C)c(O)ccc2c1=O]

1-Benzyl 4-[3-(methoxymethoxy)-2-methyl-6-propanoylphenyl]piperidine-1,4-dicarboxylate (2.10 g, yield: quantitative) was obtained through the same reaction as in Example 1-1 using 1-[2-hydroxy-4-(methoxymethoxy)-3-methylphenyl]propan-1-one (1.00 g, 4.46 mmol) obtained in Example 2-1 and 1-[(benzyloxy)carbonyl]piperidine-4-carboxylic acid (1.29 g, 4.91 mmol). Subsequently, the title compound (1.40 g, yield: 60%) was obtained through the same reaction as in Example 1-2 using the obtained compound (2.10 g, 5.70 mmol).
$^1$H-NMR (CDCl$_3$) δ: 7.92 (1H, d, J=8.6 Hz), 7.42-7.31 (5H, m), 7.14 (1H, s), 6.92 (1H, d, J=8.6 Hz), 5.19 (2H, s), 4.48-4.32 (2H, m), 3.10-3.01 (1H, m), 2.99-2.86 (2H, m), 2.31 (3H, s), 2.10 (3H, s), 1.99-1.80 (4H, m).
MS; m/z: 408 (M+H)$^+$

Example 43-2

7-(Methoxymethoxy)-3,8-dimethyl-2-(piperidin-4-yl)-4H-chromen-4-one

[Chemical formula 100]

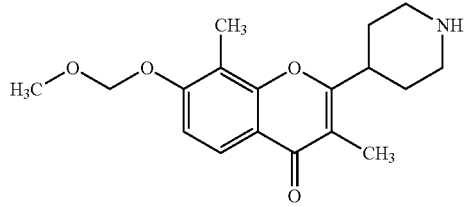

Benzyl 4-[7-(methoxymethoxy)-3,8-dimethyl-4-oxo-4H-chromen-2-yl]piperidine-1-carboxylate (6.53 g, yield: 96%) was obtained through the same reaction as in Example 2-1 using benzyl 4-(7-hydroxy-3,8-dimethyl-4-oxo-4H-chromen-2-yl)piperidine-1-carboxylate (6.11 g, 15.0 mmol) obtained in Example 42-3 and chloro(methoxy)methane (1.71 mL, 22.5 mmol). Subsequently, the title compound (4.60 g, yield: quantitative) was obtained through the same reaction as in Example 1-3 using the obtained compound (6.53 g, 14.5 mmol).

$^1$H-NMR (CDCl$_3$) δ: 8.02 (1H, d, J=9.0 Hz), 7.14 (1H, d, J=9.0 Hz), 5.30 (2H, s), 3.51 (3H, s), 3.28-3.22 (2H, m), 3.05-2.96 (1H, m), 2.83-2.74 (2H, m), 2.36 (3H, s), 2.09 (3H, s), 2.03-1.91 (2H, m), 1.87-1.79 (2H, m).
MS; m/z: 318 (M+H)$^+$.

Example 43-3

2-[1-(Ethoxyacetyl)piperidin-4-yl]-7-hydroxy-3,8-dimethyl-4H-chromen-4-one

[Chemical formula 101]

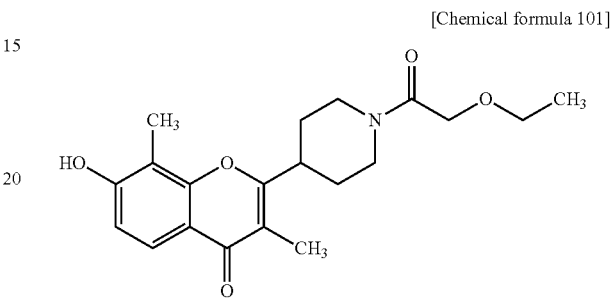

2-[1-(Methoxyacetyl)piperidin-4-yl]-7-(methoxymethoxy)-3,8-dimethyl-4H-chromen-4-one (2.10 g, yield: 83%) was obtained through the same reaction as in Example 7-3 using 7-(methoxymethoxy)-3,8-dimethyl-2-(piperidin-4-yl)-4H-chromen-4-one (2.00 g, 6.30 mmol) obtained in Example 43-2 and ethoxyacetyl chloride (1.16 g, 9.46 mmol). Subsequently, the title compound (1.40 g, yield: 75%) was obtained through the same reaction as in Example 37-5 using the obtained compound (2.10 g, 5.20 mmol).
$^1$H-NMR (CDCl$_3$) δ: 7.93 (1H, d, J=8.6 Hz), 7.35 (1H, s), 6.94 (1H, d, J=8.6 Hz), 4.85-4.78 (1H, m), 4.28 (1H, d, J=13.3 Hz), 4.18-4.11 (1H, m), 4.17 (1H, d, J=13.3 Hz), 3.61 (2H, q, J=7.0 Hz), 3.21-3.10 (2H, m), 2.79-2.68 (1H, m), 2.30 (3H, s), 2.11 (3H, s), 1.98-1.90 (4H, m), 1.27 (3H, t, J=7.0 Hz).
MS; m/z: 360 (M+H)$^+$.

Example 44

7-Hydroxy-3,8-dimethyl-2-{1-[(propan-2-yloxy)acetyl]piperidin-4-yl}-4H-chromen-4-one

[Chemical formula 102]

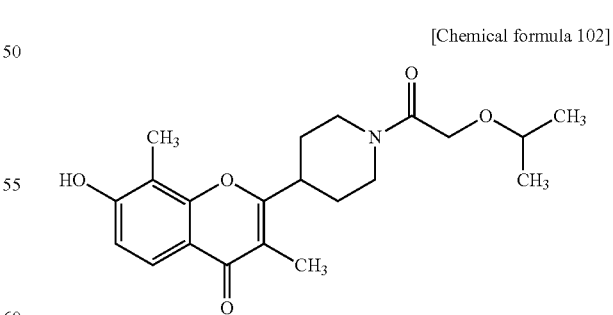

7-(Methoxymethoxy)-3,8-dimethyl-2-{1-[(propan-2-yloxy)acetyl]piperidin-4-yl}-4H-chromen-4-one (2.60 g, yield: 99%) was obtained through the same reaction as in Example 15 using 7-(methoxymethoxy)-3,8-dimethyl-2-(piperidin-4-yl)-4H-chromen-4-one (2.00 g, 6.30 mmol) obtained in Example 43-2 and ethoxyacetyl chloride (1.16 g, 9.46 mmol). Subsequently, the title compound (1.20 g, yield: 59%) was obtained through the same reaction as in Example 37-5 using the obtained compound (2.60 g, 6.20 mmol).
$^1$H-NMR (CDCl$_3$) δ: 7.94 (1H, d, J=8.6 Hz), 6.91 (1H, d, J=8.6 Hz), 6.86 (1H, s), 4.83-4.76 (1H, m), 4.24 (1H, d, J=13.3 Hz), 4.21-4.11 (1H, m), 4.17 (1H, d, J=13.3 Hz), 3.76-3.67 (1H, m), 3.22-3.09 (2H, m), 2.77-2.66 (1H, m), 2.30 (3H, s), 2.11 (3H, s), 2.02-1.87 (4H, m), 1.23 (3H, d, J=6.3 Hz), 1.22 (3H, d, J=6.3 Hz).
MS; m/z: 374 (M+H)$^+$.

The invention claimed is:
1. A compound represented by the general formula (I) or a pharmacologically acceptable salt thereof:

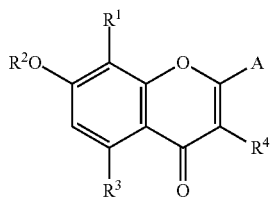

wherein each substituent is defined as follows:
R$^1$ represents
a halogen atom, a cyano group, a vinyl group, an allyl group, a nitro group, an amino group, a C3-C6 cycloalkyl group,
a C1-C6 alkyl group optionally substituted by one or two or more groups selected from substituent group a,
a C1-C6 alkoxy group optionally substituted by one or two or more groups selected from substituent group a,
a C1-C6 alkylamino group optionally substituted by one or two or more groups selected from substituent group a,
a di-C1-C6 alkylamino group optionally substituted by one or two or more groups selected from substituent group a, or
a heterocyclic group optionally substituted by one or two or more groups selected from substituent group a, wherein
the substituent group a consists of a C3-C6 cycloalkyl group, a hydroxyl group, a halogen atom, an oxo group, and a phenyl group;
R$^2$ represents a hydrogen atom or a protective group for the hydroxyl group;
R$^3$ represents a hydrogen atom, a halogen atom, or a C1-C6 alkyl group;
R$^4$ represents a hydrogen atom or a C1-C6 alkyl group optionally substituted by a C1-C6 alkoxy group; and
A represents
a 4 piperidine group substituted by one or two or more groups selected from substituent group c, wherein
the substituent group c consists of
a hydroxyl group, a hydroxy-C1-C6 alkyl group, a C1-C6 alkylsulfonyl group, an aminocarbonyl group, a C1-C6 alkylaminocarbonyl group, a di-C1-C6 alkylaminocarbonyl group,
a C3-C7 cycloalkylaminocarbonyl group, a heterocycle-carbonyl group,
a C1-C6 alkoxy-C1-C6 alkylcarbonyl group, a C1-C6 alkylaminosulfonyl group,
a di-C1-C6 alkylaminosulfonyl group,
a C3-C7 cycloalkylsulfonyl group, a heterocycle-sulfonyl group,
a C1-C6 alkyl group optionally substituted by one or two or more groups selected from substituent group d,
a C1-C6 alkylcarbonyl group optionally substituted by one or two or more groups selected from substituent group d,
a C1-C6 alkoxycarbonyl group optionally substituted by one or two or more groups selected from substituent group d,
a heterocyclic group optionally substituted by one or two or more groups selected from substituent group d,
a benzoyl group optionally substituted by one or two or more groups selected from substituent group d, and
a benzyl group optionally substituted by one or two or more groups selected from substituent group d, wherein
the substituent group d consists of
a halogen atom, a carboxy group, an oxo group, an aminocarbonyl group, a C1-C6 alkoxy group,
a C1-C6 alkoxycarbonyl group, a C1-C6 alkylaminocarbonyl group,
a di-C1-C6 alkylaminocarbonyl group, a heterocycle-carbonyl group, a phenyl group, and
a phenylaminocarbonyl group optionally substituted by one or two or more groups selected from substituent group e, wherein
the substituent group e consists of
a heterocycle-carbonyl group and a heterocycle-C1-C6 alkyl group.

2. The compound or pharmacologically acceptable salt thereof according to claim 1, wherein R$^1$ is a group selected from the following substituents:
a halogen atom, an allyl group, a C3-C6 cycloalkyl group, and a C1-C6 alkyl group optionally substituted by one or two or more groups selected from substituent group a.

3. The compound or pharmacologically acceptable salt thereof according to claim 1, wherein R$^2$ is a hydrogen atom.

4. The compound or pharmacologically acceptable salt thereof according to claim 1, wherein R$^3$ is a hydrogen atom.

5. The compound or pharmacologically acceptable salt thereof according to claim 1, wherein R$^4$ is a hydrogen atom or a methyl group.

6. The compound or pharmacologically acceptable salt thereof according to claim 1, wherein the substituent group c is the following substituent group:
a C1-C6 alkylsulfonyl group, an aminocarbonyl group, a di-C1-C6 alkylaminocarbonyl group,
a di-C1-C6 alkylaminosulfonyl group, a C1-C6 alkoxy-C1-C6 alkylcarbonyl group,
a C1-C6 alkylcarbonyl group optionally substituted by group(s) selected from substituent group d,
a C1-C6 alkoxycarbonyl group optionally substituted by group(s) selected from substituent group d,
a heterocyclic group optionally substituted by group(s) selected from substituent group d,
a benzoyl group optionally substituted by group(s) selected from substituent group d, and
a benzyl group optionally substituted by group(s) selected from substituent group d.

7. A compound selected from the group consisting of the following compounds or a pharmacologically acceptable salt thereof:
ethyl 4-(7-hydroxy-3,8-dimethyl-4-oxo-4H-chromen-2-yl)piperidine-1-carboxylate,
7-hydroxy-3,8-dimethyl-2-[1-(methylsulfonyl)piperidin-4-yl]-4H-chromen-4-one,
N-ethyl-4-(7-hydroxy-3,8-dimethyl-4-oxo-4H-chromen-2-yl)piperidine-1-carboxamide,
4-(7-hydroxy-3,8-dimethyl-4-oxo-4H-chromen-2-yl)-N,N-dimethylpiperidine-1-carboxamide, 7-hydroxy-2-[1-(methoxyacetyl)piperidin-4-yl]-3,8-dimethyl-4H-chromen-4-one,
4-(7-hydroxy-3,8-dimethyl-4-oxo-4H-chromen-2-yl)-N,N-dimethylpiperidine-1-sulfonamide,
2-(1-butyrylpiperidin-4-yl)-7-hydroxy-3,8-dimethyl-4H-chromene-4-one,2-[1-(ethylsulfonyl)piperidin-4-yl]-7-hydroxy-3,8-dimethyl-4H-chromen-4-one,
7-hydroxy-3,8-dimethyl-2-[1-(3,3,3-trifluoropropanoyl)piperidin-4-yl]-4H-chromen-4-one,
7-hydroxy-3,8-dimethyl-2-(1-propanoylpiperidin-4-yl)-4H-chromen-4-one,
2-(1-acetylpiperidin-4-yl)-7-hydroxy-3,8-dimethyl-4H-chromen-4-one,
7-hydroxy-2-(1-isobutyrylpiperidin-4-yl)-3,8-dimethyl-4H-chromen-4-one,
2-(1-benzoylpiperidin-4-yl)-7-hydroxy-3,8-dimethyl-4H-chromen-4-one,
7-hydroxy-3,8-dimethyl-2-[1-(1,3-thiazol-2-yl)piperidin-4-yl]-4H-chromen-4-one,
7-hydroxy-3,8-dimethyl-2-(1-pyridin-2-ylpiperidin-4-yl)-4H-chromen-4-one,
7-hydroxy-3,8-dimethyl-2-(1-pyrazin-2-ylpiperidin-4-yl)-4H-chromen-4-one,
4-{[4-(7-hydroxy-3,8-dimethyl-4-oxo-4H-chromen-2-yl)piperidin-1-yl]methyl}-N-methylbenzamide,
4-{[4-(7-hydroxy-3,8-dimethyl-4-oxo-4H-chromen-2-yl)piperidin-1-yl]methyl}-N,N-dimethylbenzamide,
8-allyl-7-hydroxy-3-methyl-2-(1-propanoylpiperidin-4-yl)-4H-chromen-4-one,
8-bromo-7-hydroxy-3-methyl-2-(1-propanoylpiperidin-4-yl)-4H-chromen-4-one, and
8-cyclopropyl-7-hydroxy-3-methyl-2-(1-propanoylpiperidin-4-yl)-4H-chromen-4-one.

8. A pharmaceutical composition comprising a compound or pharmacologically acceptable salt thereof according to claim 1.

9. A method for promoting osteogenesis in a subject in need thereof, comprising administering to said subject an effective amount of a pharmaceutical composition according to claim 8 to a mammal.

10. A method for treating a disease associated with bone metabolism, comprising administering to a subject in need thereof an effective amount of a pharmaceutical composition according to claim 8 to a mammal.

11. The method of claim 10 wherein the disease is elected from osteoporosis or bone fracture.

12. A method for the treatment of periodontal disease or the stabilization of an artificial tooth root, comprising administering to a subject in need thereof an effective amount of a pharmaceutical composition according to claim 8 to a mammal.

* * * * *